US010945420B2

(12) United States Patent
Shen et al.

(10) Patent No.: US 10,945,420 B2
(45) Date of Patent: Mar. 16, 2021

(54) GENETICALLY MODIFIED NON-HUMAN ANIMAL WITH HUMAN OR CHIMERIC CD3E

(71) Applicants: Biocytogen Pharmaceuticals (Beijing) Co., Ltd., Beijing (CN); Biocytogen JiangSu Co., Ltd., Haimen (CN)

(72) Inventors: Yuelei Shen, Beijing (CN); Yanan Guo, Beijing (CN); Rui Huang, Beijing (CN); Xiaofei Zhou, Beijing (CN); Yang Bai, Beijing (CN); Jiawei Yao, Beijing (CN); Chaoshe Guo, Beijing (CN)

(73) Assignees: BiocytogenPharmaceuticals (Beijing) Co., Ltd., Beijing (CN); Biocytogen JiangSu Co., Ltd., Haimen (CN)

(*) Notice: Subject to any disclaimer, the term of this patent is extended or adjusted under 35 U.S.C. 154(b) by 0 days.

(21) Appl. No.: 16/436,805

(22) Filed: Jun. 10, 2019

(65) Prior Publication Data
US 2019/0373869 A1  Dec. 12, 2019

Related U.S. Application Data

(63) Continuation of application No. PCT/CN2018/120713, filed on Dec. 12, 2018.

(30) Foreign Application Priority Data

Dec. 12, 2017 (CN) .......................... 201711316875.2
May 8, 2018 (CN) .......................... 201810434327.8
Oct. 26, 2018 (CN) .......................... 201811255583.7

(51) Int. Cl.
| | | |
|---|---|---|
| *C12N 5/00* | (2006.01) | |
| *C12N 5/02* | (2006.01) | |
| *A01K 67/027* | (2006.01) | |
| *A61K 49/00* | (2006.01) | |
| *A61K 35/51* | (2015.01) | |

(52) U.S. Cl.
CPC .......... *A01K 67/0278* (2013.01); *A61K 35/51* (2013.01); *A61K 49/0008* (2013.01); *A01K 2207/15* (2013.01); *A01K 2227/105* (2013.01); *A01K 2267/0331* (2013.01)

(58) Field of Classification Search
CPC .................................................... A61K 35/51
See application file for complete search history.

(56) References Cited

U.S. PATENT DOCUMENTS

| | | | |
|---|---|---|---|
| 4,683,195 A | 7/1987 | Mullis et al. | |
| 2006/0275292 A1 | 12/2006 | Delovitch | |
| 2007/0292416 A1 | 12/2007 | Rother et al. | |
| 2015/0106961 A1 | 4/2015 | Rojas et al. | |
| 2017/0164588 A1* | 6/2017 | Olson ................ | A01K 67/0278 |

FOREIGN PATENT DOCUMENTS

| | | |
|---|---|---|
| CN | 1421459 | 6/2003 |
| CN | 107105633 | 8/2017 |
| WO | WO 2011002988 | 1/2011 |
| WO | WO 2017010423 | 1/2017 |
| WO | WO 2017150763 | 9/2017 |
| WO | WO2018001241 | 1/2018 |
| WO | WO2018041118 | 3/2018 |
| WO | WO2018041119 | 3/2018 |
| WO | WO2018041120 | 3/2018 |
| WO | WO2018041121 | 3/2018 |
| WO | WO2018068756 | 4/2018 |
| WO | WO2018086583 | 5/2018 |
| WO | WO2018086594 | 5/2018 |
| WO | WO2018121787 | 7/2018 |
| WO | WO2018177440 | 10/2018 |
| WO | WO2018177441 | 10/2018 |
| WO | WO 2016085889 | 6/2019 |

OTHER PUBLICATIONS

Gobel, J Immunol 2000; 164:879-883.*
Maksimenko et al., 2013 (Acta Naturae, vol. 5, No. 1, p. 33-46).*
Auerbach et al., "Establishment and Chimera Analysis of 129/SvEv- and C57BL/6-derived mouse embryonic stem cell lines," BioTechniques, 2000.
Festing et al., Revise nomenclature for strain 129 mice, Mammalian Genome, 1999, 10:836.
Firtina et al., "NP_000724.1, t-cell surface glycoprotein CD3 epsilon chain precursor [Homo sapiens]," GenBank, 2017, _ pages.
International Search Report and Written Opinion in International Appln. No. PCT/CN2018/120713, dated Jan. 29, 2019, 9 pages.
Ito et al., "NOD/SCID/ ycnull mouse: an excellent recipient mouse model for engraftment of human cells," Blood, 2002, 100(9):3175-3182.
Kuhn et al., "Therapeutic anti-CD3 monoclonal antibodies: from bench to bedside," Immunotherapy, 2016, 8(8):889-906.
Smith-Garvin et al., "T cell activation," Annual review of immunology, 2009, 27:591-619.
Trinquand et al., "Triggering the TCR developmental checkpoint activated a therapeutically targetable tumor suppressive pathway in t-cell leukemia," Cancer Discovery, 2016, 6:972-985.
Ueda et al., "Entire CD3ε, δ, and γ humanized mouse to evaluate human CD3-mediated therapeutics," Scientific Reports, 2017, 7:1-15.
Yin et al., "Delivery technologies for genome editing," Nature Reviews Drug Discovery, 2017, 16(6):387-399.
GenBank Accession No. AAV38740.1, "CD3E antigen, epsilon polypeptide (TiT3 complex), partial [synthetic construct]," Jul. 26, 2016, 1 page.

(Continued)

*Primary Examiner* — Valerie E Bertoglio
(74) *Attorney, Agent, or Firm* — Fish & Richardson P.C.

(57) ABSTRACT

The present disclosure relates to genetically modified non-human animals that express a human or chimeric (e.g., humanized) CD3e (T-cell surface glycoprotein CD3 epsilon chain), and methods of use thereof.

18 Claims, 30 Drawing Sheets

Specification includes a Sequence Listing.

(56) References Cited

OTHER PUBLICATIONS

GenBank Accession No. JN955596.1, "Mus musculus targeted non-conditional, lacZ-tagged mutant allele Cd3e:tm1e(EUCOMM)Hmgu; transgenic," Nov. 5, 2011, 10 pages.
GenBank Accession No. NC_000075.6, "Mus musculus strain C57BL/6J chromosome 9, GRCm38 C57BL/6J," Feb. 23, 2012, 1 page.
GenBank Accession No. NG_007383.1, "*Homo sapiens* CD3e molecule (CD3E), RefSeqGene (LRG_38) on chromosome 11," Oct. 7, 2016, 6 pages.
Liu et al., "Establishment of humanized lung cancer heterotopic mouse model," Journal of Clinical and Pathological Research, 2014, 34(4):364-370.
Wang et al., "Molecular Pharmacology," China Medical Science Press (ISBN-10: 7506743965), 2011, 108 (with English abstract).

\* cited by examiner (A) WT-F/WT-R — 320bp (B) WT-F/Mut-R — 268bp (C) Frt-F/Frt-R — 393bp, 306bp (D) Flp-F2 / Flp-R2 — 325bp

FIG. 30

| Score | Expect | Method | Identities | Positives | Gaps |
|---|---|---|---|---|---|
| 209 bits(531) | 6e-74 | Compositional matrix adjust. | 123/207(59%) | 146/207(70%) | 18/207(8%) |

```
Mouse    1   MRWNTFWGILCLSLLAVGT-CQDDAENI------EYKVSISGTSVELTCPLDSDENLKWE    53
             M+   T W  +L L LL+VG   QD    E  +       YKVSISGT+V LTCP        + W+
Human    1   MQSGTHWRVLGLCLLSVGVWGQDGNEEMGGITQTPYKVSISGTTVILTCPQYPGSEIIWQ    60

Mouse   54   KNGQELPQKHDK--------HLVLQDFSEVEDSGYYVCYTPAS----NKNTYLYLKARVCE   102
             N  +  +     D          HL L++FSE+E SGYYVCY   S    + N YLYL+ARVCE
Human   61   HNDKNIGGDEDDKNIGSDEDHLSLKEFSELEQSGYYVCYPRGSKPEDANFYLYLRARVCE   120

Mouse  103   YCVEVDLTAVAIIIVDICITLGLLMVIYYWSKNRKAKAKPVTRGTGAGSRPRGQNKERP   162
             C+E+D+  +VA  I+IVDICIT  GLL+++YYWSKNRKAKAKPVTRG GAG  R  RGQNKERP
Human  121   NCMEMDVMSVATIVIVDICITGGLLLLVYYWSKNRKAKAKPVTRGAGAGGRQRGQNKERP   180

Mouse  163   PPVPNPDYEPIRKGQRDLYSGLNQRAV   189
             PPVPNPDYEPIRKGQRDLYSGLNQR +
Human  181   PPVPNPDYEPIRKGQRDLYSGLNQRRI   207
``` ated animal models that are suitable for human antibody screening and evaluation will significantly improve the efficiency of new drug development and reduce the cost for drug research and development.

GENETICALLY MODIFIED NON-HUMAN ANIMAL WITH HUMAN OR CHIMERIC CD3E

CLAIM OF PRIORITY

This application is a continuation of and claims priority to international Application No. PCT/CN2018/120713, filed on Dec. 12, 2018, which claims the benefit of Chinese Patent Application No. 201711316875.2, filed on Dec. 12, 2017, Chinese Patent Application No. 201810434327.8, filed on May 8, 2018, and Chinese Patent Application No. 201811255583.7, filed on Oct. 26, 2018. The entire contents of the foregoing are incorporated herein by reference.

TECHNICAL FIELD

This disclosure relates to genetically modified animal expressing human or chimeric (e.g., humanized) CD3e, and methods of use thereof.

BACKGROUND

The immune system has developed multiple mechanisms to prevent deleterious activation of immune cells. One such mechanism is the intricate balance between positive and negative costimulatory signals delivered to immune cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure relates to transgenic non-human animal with human or chimeric (e.g., humanized) CD3e (T-cell surface glycoprotein CD3 epsilon chain; also known as CD3ε or T-Cell Surface Antigen T3/Leu-4 Epsilon Chain), and methods of use thereof.

The animal model can express human CD3e or chimeric CD3e (e.g., humanized CD3e) protein in its body. It can be used in the studies on the function of CD3e gene, and can be used in the screening and evaluation of anti-human CD3e antibodies. In addition, the animal models prepared by the methods described herein can be used in drug screening, pharmacodynamics studies, treatments for immune-related diseases (e.g., autoimmune disease), and cancer therapy for human CD3e target sites; they can also be used to facilitate the development and design of new drugs, and save time and cost. In summary, this disclosure provides a powerful tool for studying the function of CD3e protein and a platform for screening cancer drugs.

In one aspect, the disclosure relates to a genetically-modified, non-human animal whose genome comprises at least one chromosome comprising a sequence encoding a human or chimeric CD3e. In some embodiments, the sequence encoding the human or chimeric CD3e is operably linked to an endogenous regulatory element at the endogenous CD3e gene locus in the at least one chromosome.

In some embodiments, the sequence encoding a human or chimeric CD3e comprises a sequence encoding an amino acid sequence that is at least 50%, 55%, 65%, 70%, 75%, 80%, 85%, 90%, 95%, 99%, or 100% identical to human CD3e (NP 000724.1 (SEQ ID NO: 7)). In some embodiments, the sequence encoding a human or chimeric CD3e comprises a sequence encoding an amino acid sequence that is at least 50%, 55%, 65%, 70%, 75%, 80%, 85%, 90%, 95%, 99%, or 100% identical to SEQ ID NO: 10. In some embodiments, the sequence encoding a human or chimeric CD3e comprises a sequence that is at least 50%, 55%, 65%, 70%, 75%, 80%, 85%, 90%, 95%, 99%, or 100% identical to amino acids 1-126 of SEQ ID NO: 7.

In some embodiments, the animal is a mammal, e.g., a monkey, a rodent or a mouse. In some embodiments, the animal is a mouse.

In some embodiments, the animal does not express endogenous CD3e. In some embodiments, the animal has one or more cells expressing human or chimeric CD3e.

In some embodiments, the animal has one or more cells expressing human or chimeric CD3e, and the expressed human or chimeric CD3e can form a CD3 complex with human CD3 gamma (γ), delta (δ) and zeta (ζ) polypeptides. In some embodiments, the animal has one or more cells expressing human or chimeric CD3e, and the expressed human or chimeric CD3e can form a CD3 complex with endogenous CD3 gamma (γ), delta (δ) and zeta (ζ) polypeptides.

In one aspect, the disclosure relates to a genetically-modified, non-human animal, wherein the genome of the animal comprises a replacement of a sequence encoding a region of endogenous CD3e with a sequence encoding a corresponding region of human CD3e at an endogenous CD3e gene locus.

In some embodiments, the sequence encoding the corresponding region of human CD3e is operably linked to an endogenous regulatory element at the endogenous CD3e locus, and one or more cells of the animal expresses a chimeric CD3e. In some embodiments, the animal does not express endogenous CD3e. In some embodiments, the replaced locus is the extracellular region of CD3e.

In some embodiments, the animal has one or more cells expressing a chimeric CD3e having an extracellular region, a transmembrane region, and a cytoplasmic region In some embodiments, the extracellular region comprises a sequence that is at least 50%, 60%, 70%, 80%, 90%, 95%, or 99% identical to the extracellular region of human CD3e. In some embodiments, the extracellular region of the chimeric CD3e has a sequence that has at least 10, 20, 30, 40, 50, 60, 70, 80, 90, 100, 110, 120, 130, 140, 150, 160, 170, or 180 contiguous amino acids that are identical to a contiguous sequence present in the extracellular region of human CD3e.

In some embodiments, the animal is a mouse, and the sequence encoding the region of endogenous CD3e is exon 2, exon 3, exon 4, exon 5, and/or exon 6 of the endogenous mouse CD3e gene. In some embodiments, the sequence encoding the region of endogenous CD3e is exon 2, exon 3, exon 4, exon 5, exon 6, exon 7, and/or exon 8 of the endogenous mouse CD3e gene.

In some embodiments, the animal is heterozygous with respect to the replacement at the endogenous CD3e gene locus. In some embodiments, the animal is homozygous with respect to the replacement at the endogenous CD3e gene locus.

In one aspect, the disclosure relates to methods for making a genetically-modified, non-human animal. The methods involve replacing in at least one cell of the animal, at an endogenous CD3e gene locus, a sequence encoding a region of an endogenous CD3e with a sequence encoding a corresponding region of human CD3e.

In some embodiments, the sequence encoding the corresponding region of human CD3e comprises exon 2, exon 3, exon 4, exon 5, exon 6, exon 7, exon 8, and/or exon 9, or a part thereof, of a human CD3e gene. In some embodiments, the sequence encoding the corresponding region of CD3e comprises exon 2, exon 3, exon 4, exon 5, exon 6, and/or exon 7, or a part thereof, of a human CD3e gene. In some embodiments, the sequence encoding the corresponding region of human CD3e encodes amino acids 1-126 of SEQ ID NO: 7.

In some embodiments, the region is located within the extracellular region of CD3e.

In some embodiments, the animal is a mouse, and the endogenous CD3e locus is exon 2, exon 3, exon 4, exon 5, and/or exon 6 of the mouse CD3e gene. In some embodiments, the endogenous CD3e locus is exon 2, exon 3, exon 4, exon 5, exon 6, exon 7, and/or exon 8 of the mouse CD3e gene.

In one aspect, the disclosure relates to a non-human animal comprising at least one cell comprising a nucleotide sequence encoding a genetically engineered CD3e polypeptide. In some embodiments, the genetically engineered CD3e polypeptide comprises at least 50 contiguous amino acid residues that are identical to the corresponding contiguous amino acid sequence of a human CD3e. In some embodiments, the animal expresses the genetically engineered CD3e.

In some embodiments, the genetically engineered CD3e polypeptide has at least 50 contiguous amino acid residues that are identical to amino acid sequence of a human CD3e extracellular region.

In some embodiments, the genetically engineered CD3e polypeptide comprises a sequence that is at least 50%, 60%, 70%, 80%, 90%, 95%, or 99% identical to amino acids 1-126 of SEQ ID NO: 7. In some embodiments, the genetically engineered CD3e polypeptide comprises a sequence that is at least 50%, 60%, 70%, 80%, 90%, 95%, or 99% identical to SEQ ID NO: 7.

In some embodiments, the nucleotide sequence is operably linked to an endogenous CD3e regulatory element of the animal.

In some embodiments, the genetically engineered CD3e polypeptide comprises an endogenous CD3e transmembrane region and/or an endogenous CD3e cytoplasmic region.

In some embodiments, the nucleotide sequence is integrated to an endogenous CD3e gene locus of the animal.

In some embodiments, the genetically engineered CD3e has at least one mouse CD3e activity and/or at least one human CD3e activity.

In one aspect, the disclosure relates to methods of making a genetically-modified mouse cell that expresses a human or chimeric CD3e. The methods involve replacing at an endogenous mouse CD3e gene locus, a nucleotide sequence encoding a region of mouse CD3e with a nucleotide sequence encoding a corresponding region of human CD3e, thereby generating a genetically-modified mouse cell that includes a nucleotide sequence that encodes the human or chimeric CD3e. In some embodiments, the mouse cell expresses the human or chimeric CD3e.

In some embodiments, the chimeric CD3e comprises an extracellular region of human CD3e comprising a human signal peptide sequence; and a transmembrane and/or a cytoplasmic region of mouse CD3e.

In some embodiments, the nucleotide sequence encoding the human or chimeric CD3e is operably linked to an endogenous CD3e regulatory region, e.g., promoter.

In some embodiments, the animal further comprises a sequence encoding an additional human or chimeric protein. In some embodiments, the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), TNF Receptor Superfamily Member 4 (OX40), CD3δ, CD3γ, CD40, or CD278.

In one aspect, the disclosure relates to methods of determining effectiveness of an anti-CD3e antibody for the treatment of cancer. The methods involve administering the anti-CD3e antibody to the animal as described herein, wherein the animal has a tumor; and determining the inhibitory effects of the anti-CD3e antibody to the tumor. In some embodiments, the tumor comprises one or more cancer cells that are injected into the animal. In some embodiments, determining the inhibitory effects of the anti-CD3e antibody to the tumor involves measuring the tumor volume in the animal. In some embodiments, the tumor cells are melanoma cells, pancreatic carcinoma cells, mesothelioma cells, or solid tumor cells.

In one aspect, the disclosure relates to methods of determining effectiveness of an anti-CD3e antibody in inhibiting an immune response. The methods involve administering the anti-CD3e antibody to the animal as described herein, wherein the animal has a tumor; and determining the effects of the anti-CD3e antibody on the tumor. In some embodiments, the tumor comprises one or more cancer cells that are injected into the animal. In some embodiments, determining the effects of the anti-CD3e antibody on the tumor involves measuring the tumor volume in the animal.

In one aspect, the disclosure relates to methods of determining effectiveness of an anti-CD3e antibody in inhibiting an immune response. The methods involve administering the anti-CD3e antibody to the animal as described herein; and determining the percentage of T cells in peripheral blood.

In one aspect, the disclosure relates to methods of determining effectiveness of an anti-CD3e antibody in activating T cells. The methods involve administering the anti-CD3e antibody to the animal as described herein; and determining the percentage of CD25+ T cells or CD 69+ T cells in a cell population. In some embodiments, the cell population is derived from the spleen, thymus, inguinal lymph nodes or mesenteric lymph nodes of the animal.

In one aspect, the disclosure relates to methods of determining effectiveness of an anti-CD3e antibody in activating T cells. The methods involve administering the anti-CD3e antibody to the animal as described herein; and determining the expression of CD3 in a cell population. In some embodiments, the cell population is derived from the spleen, thymus, inguinal lymph nodes or mesenteric lymph nodes of the animal.

In one aspect, the disclosure relates to a protein comprising an amino acid sequence, wherein the amino acid sequence is one of the following:
 (a) an amino acid sequence set forth in SEQ ID NO: 10;
 (b) an amino acid sequence that is at least 90% identical to SEQ ID NO: 10;
 (c) an amino acid sequence that is at least 91%, 92%, 93%, 94%, 95%, 96%, 97%, 98%, or 99% identical to SEQ ID NO: 10;
 (d) an amino acid sequence that is different from the amino acid sequence set forth in SEQ ID NO: 10 by no more than 10, 9, 8, 7, 6, 5, 4, 3, 2 or 1 amino acid; and
 (e) an amino acid sequence that comprises a substitution, a deletion and/or insertion of one, two, three, four, five or more amino acids to the amino acid sequence set forth in SEQ ID NO: 10.

In one aspect, the disclosure relates to a nucleic acid comprising a nucleotide sequence, wherein the nucleotide sequence is one of the following:
 (a) a sequence that encodes the protein as described herein;
 (b) SEQ ID NO: 3, SEQ ID NO: 8 or SEQ ID NO: 9;
 (c) SEQ ID NO: 39 or SEQ ID NO: 40;
 (d) a sequence that is at least 90% identical to SEQ ID NO: 3, SEQ ID NO: 8, SEQ ID NO: 9, SEQ ID NO: 39, or SEQ ID NO: 40;
 (e) a sequence that is at least 91%, 92%, 93%, 94%, 95%, 96%, 97%, 98%, or 99% identical to SEQ ID NO: 3, SEQ ID NO: 8, SEQ ID NO: 9, SEQ ID NO: 39, or SEQ ID NO: 40;

In one aspect, the disclosure relates to a cell comprising the protein as described herein and/or the nucleic acid as described herein. In one aspect, the disclosure relates to an animal comprising the protein as described herein and/or the nucleic acid as described herein.

In one aspect, the disclosure relates to methods of determining effectiveness of an anti-CD3e antibody and an additional therapeutic agent for the treatment of a tumor. The methods involve administering the anti-CD3e antibody and the additional therapeutic agent to the animal as described herein, wherein the animal has a tumor; and determining the inhibitory effects on the tumor.

In some embodiments, the animal further comprises a sequence encoding a human or chimeric programmed cell death protein 1 (PD-1). In some embodiments, the animal further comprises a sequence encoding a human or chimeric programmed death-ligand 1 (PD-L1). In some embodiments, the additional therapeutic agent is an anti-PD-1 antibody or an anti-PD-L1 antibody. In some embodiments, the tumor comprises one or more tumor cells that express PD-L1 or PD-L2.

In some embodiments, the tumor is caused by injection of one or more cancer cells into the animal. In some embodiments, determining the inhibitory effects of the treatment involves measuring the tumor volume in the animal.

In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to methods of determining effectiveness of an anti-CD3e antibody for the treatment of various immune-related disorders, e.g., autoimmune diseases.

In another aspect, the disclosure also provides a genetically-modified, non-human animal whose genome comprise a disruption in the animal's endogenous CD3e gene, wherein the disruption of the endogenous CD3e gene comprises deletion of exon 1, exon 2, exon 3, exon 4, exon 5, exon 6, exon 7, and/or exon 8 or part thereof of the endogenous CD3e gene.

In some embodiments, the disruption of the endogenous CD3e gene comprises deletion of one or more exons or part of exons selected from the group consisting of exon 1, exon 2, exon 3, exon 4, exon 5, exon 6, exon 7, and exon 8 of the endogenous CD3e gene.

In some embodiments, the disruption of the endogenous CD3e gene further comprises deletion of one or more introns or part of introns selected from the group consisting of intron 1, intron 2, intron 3, intron 4, intron 5, intron 6, and intron 7 of the endogenous CD3e gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous CD3e gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, and/or exon 8 (e.g., deletion of at least 50 nucleotides of exon 2 or exon 7).

In some embodiments, the mice described in the present disclosure can be mated with the mice containing other human or chimeric genes (e.g., chimeric SIRPα, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In another aspect, the disclosure further provides methods of determining toxicity of an agent (e.g., a CD3 antagonist or agonist, or a TCR antagonist or agonist). The methods involve administering the agent to the animal as described herein; and determining weight change of the animal. In some embodiments, the method further involve performing a blood test (e.g., determining red blood cell count).

In one aspect, the disclosure relates to a targeting vector, including a) a DNA fragment homologous to the 5' end of a region to be altered (5' arm), which is selected from the CD3e gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD3e gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000075.6; c) the DNA fragment homologous to the 3' end of the region to be altered (3' arm/receptor) is selected from the nucleotide sequences that have at least 90% homology to the NCBI accession number NC_000075.6.

In some embodiments, a) the DNA fragment homologous to the 5' end of a region to be altered (5' arm/receptor) is selected from the nucleotides from the position 45014642 to the position 45009397 of the NCBI accession number NC_000075.6; c) the DNA fragment homologous to the 3' end of the region to be altered (3' arm/receptor) is selected from the nucleotides from the position 44998440 to the position 44994894 of the NCBI accession number NC_000075.6.

In some embodiments, a length of the selected genomic nucleotide sequence is more than 3 kb, 3.5 kb, 4 kb, 4.5 kb, 5 kb, 5.5 kb, or 6 kb. In some embodiments, the region to be altered is exon 2, exon 3, exon 4, exon 5, and/or exon 6 of mouse CD3e gene. In some embodiments, the region to be altered is exon 2, exon 3, exon 4, exon 5, exon 6, exon 7, and/or exon 8 of mouse CD3e gene.

In some embodiments, the sequence of the 5' arm is shown in SEQ ID NO: 1. In some embodiments, the sequence of the 3' arm is shown in SEQ ID NO: 2. In some embodiments, the sequence of the 5' arm is shown in SEQ ID NO: 37. In some embodiments, the sequence of the 3' arm is shown in SEQ ID NO: 38.

In some embodiments, the targeting vector further includes a selectable gene marker.

In some embodiments, the target region is derived from human. In some embodiments, the target region is a part or entirety of the nucleotide sequence of a humanized CD3e. In some embodiments, the nucleotide sequence is shown as one or more of exon 2, exon 3, exon 4, exon 5, exon 6, and exon 7 of the human CD3e. In some embodiments, the nucleotide sequence is shown as one or more of exon 2, exon 3, exon 4, exon 5, exon 6, exon 7, exon 8, and exon 9 of the human CD3e.

In some embodiments, the nucleotide sequence of the human CD3e encodes the human CD3e protein with the NCBI accession number NP_000724.1 (SEQ ID NO: 7). In some emboldens, the nucleotide sequence of the human CD3e is selected from the nucleotides from the position 118304953 to the position 118313732 of NC_000011.10 (SEQ ID NO: 3). In some emboldens, the nucleotide sequence of the human CD3e is selected from the nucleotides from the position 118304953 to the position 118315542 of NC_000011.10 (SEQ ID NO: 39).

The disclosure also relates to a cell including the targeting vector as described herein.

The disclosure also relates to a method for establishing a genetically-modified non-human animal expressing two human or chimeric (e.g., humanized) genes. The method includes the steps of
(a) using the method for establishing a CD3e gene humanized animal model to obtain a CD3e gene genetically modified humanized mouse;
(b) mating the CD3e gene genetically modified humanized mouse obtained in step (a) with another humanized mouse, and then screening to obtain a double humanized mouse model.

In some embodiments, in step (b), the CD3e gene genetically modified humanized mouse obtained in step (a) is mated with a PD-1 or PD-L1 humanized mouse to obtain a CD3e and PD-1 double humanized mouse model or a CD3e and PD-L1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized CD3e gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a CD3e amino acid sequence of a humanized mouse, wherein the amino acid sequence is selected from the group consisting of:
a) an amino acid sequence shown in SEQ ID NO: 10;
b) an amino acid sequence having a homology of at least 90% with the amino acid sequence shown in SEQ ID NO: 10;
c) an amino acid sequence encoded by a nucleic acid sequence, wherein the nucleic acid sequence is able to hybridize to a nucleotide sequence encoding the amino acid shown in SEQ ID NO: 10 under a low stringency condition or a strict stringency condition;
d) an amino acid sequence having a homology of at least 90%, 91%, 92%, 93%, 94%, 95%, 96%, 97%, 98%, or at least 99% with the amino acid sequence shown in SEQ ID NO: 10;
e) an amino acid sequence that is different from the amino acid sequence shown in SEQ ID NO: 10 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 10.

The disclosure also relates to a CD3e nucleic acid sequence of a humanized mouse, wherein the nucleic acid sequence is selected from the group consisting of:
a) a nucleic acid sequence that encodes the CD3e amino acid sequence of a humanized mouse;
b) a nucleic acid sequence that is set forth in SEQ ID NO: 3, SEQ ID NO: 8, SEQ ID NO: 9, SEQ ID NO: 39, or SEQ ID NO: 40;
c) a nucleic acid sequence that can hybridize to the nucleotide sequence as shown in SEQ ID NO: 3, SEQ ID NO: 8, SEQ ID NO: 9, SEQ ID NO: 39, or SEQ ID NO: 40 under a low stringency condition or a strict stringency condition;
d) a nucleic acid sequence that has a homology of at least 90%, 91%, 92%, 93%, 94%, 95%, 96%, 97%, 98%, or at least 99% with the nucleotide sequence as shown in SEQ ID NO: 3, SEQ ID NO: 8, SEQ ID NO: 9, SEQ ID NO: 39, or SEQ ID NO: 40;
f) a nucleic acid sequence that encodes an amino acid sequence, wherein the amino acid sequence has a homology of at least 90% with the amino acid sequence shown in SEQ ID NO: 10;
g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 10;

h) a nucleic acid sequence that encodes an amino acid sequence, wherein the amino acid sequence is different from the amino acid sequence shown in SEQ ID NO: 10 by no more than 10, 9, 8, 7, 6, 5, 4, 3, 2 or no more than 1 amino acid; and/or i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 10.

The disclosure further relates to a CD3e genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CD3e gene function, human CD3e antibodies, the drugs or efficacies for human CD3e targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 11A is the result for the unstimulated wildtype C57BL/6 mouse. FIG. 11B is the result for the wildtype C57BL/6 mouse stimulated by anti-mCD3 antibody. FIG. 11C is the result for the wildtype C57BL/6 mouse stimulated by anti-hCD3 antibody. FIG. 11D is the result for the humanized heterozygous mouse (hCD3-part version) stimulated by anti-hCD3 antibody. The cells were stained by APC anti-mouse CD69 antibody (mCD69 APC) and PE anti-mouse CD25 antibody (mCD25 PE).

FIGS. 12A and 12E are the results for the unstimulated wildtype C57BL/6 mouse. FIGS. 12B and 12F are the results for the wildtype C57BL/6 mouse stimulated by anti-mCD3 antibody. FIGS. 12C and 12G are the results for the wildtype C57BL/6 mouse stimulated by anti-hCD3 antibody. FIGS. 12D and 12H are the results for the humanized heterozygous mouse (hCD3-part version) stimulated by anti-hCD3 antibody. The cells were stained by mTcRβ PerCP, PerCP anti-mouse CD3e Antibody (mCD3 PerCP), or PerCP anti-human CD3 Antibody (hCD3 PerCP).

FIG. 13A is the result for the unstimulated wildtype C57BL/6 mouse. FIG. 13B is the result for the wildtype C57BL/6 mouse stimulated by anti-hCD3 antibody. FIG. 13C is the result for the humanized heterozygous mouse (hCD3-full version) stimulated by anti-hCD3 antibody. The cells were stained by APC anti-mouse CD69 antibody (mCD69 APC) and PE anti-mouse CD25 antibody (mCD25 PE).

FIGS. 14A and 14D are the results for the unstimulated wildtype C57BL/6 mouse. FIGS. 14B and 14E are the results for the wildtype C57BL/6 mouse stimulated by anti-hCD3 antibody. FIGS. 14C and 14F are the results for the humanized heterozygous mouse (hCD3-full version) stimulated by anti-hCD3 antibody. The cells were stained by mTcRβ PerCP and PerCP anti-mouse CD3e antibody (mCD3 PerCP), or mTcRβ PerCP and PerCP anti-human CD3 antibody (hCD3 PerCP).

FIGS. 15A and 15D are the results for the wildtype C57BL/6 mouse. FIGS. 15B and 15E are the results for the humanized homozygous mouse (hCD3-full version). FIGS. 15C and 15F are the results for the humanized homozygous mouse (hCD3-part version). In FIGS. 15A-15C, the cells were stained by Brilliant Violet 605™ anti-mouse CD19 Antibody (mCD19) and mTcRβ PerCP. In FIGS. 15D-15F, the cells were stained by PerCP anti-mouse CD3ε Antibody (mCD3) and mTcRβ PerCP.

FIGS. 16A and 16D are the results for the wildtype C57BL/6 mouse. FIGS. 16B and 16E are the results for the humanized homozygous mouse (hCD3-full version). FIGS. 16C and 16F are the results for the humanized homozygous mouse (hCD3-part version). In FIGS. 16A-16C, the cells were stained by APC anti-human CD3 Antibody (hCD3) and mTcRβ PerCP. In FIGS. 16D-16F, the cells were stained by Brilliant Violet 510™ anti-mouse CD8a (mCD8) antibody and Brilliant Violet 421™ anti-mouse CD4 antibody (mCD4).

FIGS. 17A and 17D are the results for the wildtype C57BL/6 mouse. FIGS. 17B and 17E are the results for the humanized homozygous mouse (hCD3-full version). FIGS. 17C and 17F are the results for the humanized homozygous mouse (hCD3-part version). In FIGS. 17A-17C, the cells were stained by Brilliant Violet 605™ anti-mouse CD19 Antibody (mCD19) and mTcRβ PerCP. In FIGS. 17D-17F, the cells were stained by PerCP anti-mouse CD3ε Antibody (mCD3) and mTcRβ PerCP.

FIGS. 18A and 18D are the results for the wildtype C57BL/6 mouse. FIGS. 18B and 18E are the results for the humanized homozygous mouse (hCD3-full version). FIGS. 18C and 18F are the results for the humanized homozygous mouse (hCD3-part version). In FIGS. 18A-18C, the cells were stained by APC anti-human CD3 Antibody (hCD3) and mTcRβ PerCP. In FIGS. 18D-18F, the cells were stained by Brilliant Violet 510™ anti-mouse CD8a (mCD8) antibody and Brilliant Violet 421™ anti-mouse CD4 antibody (mCD4).

FIGS. 19A and 19D are the results for the wildtype C57BL/6 mouse. FIGS. 19B and 19E are the results for the humanized homozygous mouse (hCD3-full version). FIGS. 19C and 19F are the results for the humanized homozygous mouse (hCD3-part version). In FIGS. 19A-19C, the cells were stained by Brilliant Violet 605™ anti-mouse CD19 Antibody (mCD19) and mTcRβ PerCP. In FIGS. 19D-19F, the cells were stained by PerCP anti-mouse CD3ε Antibody (mCD3) and mTcRβ PerCP.

FIGS. 20A and 20D are the results for the wildtype C57BL/6 mouse. FIGS. 20B and 20E are the results for the humanized homozygous mouse (hCD3-full version). FIGS. 20C and 20F are the results for the humanized homozygous mouse (hCD3-part version). In FIGS. 20A-20C, the cells were stained by APC anti-human CD3 Antibody (hCD3) and mTcRβ PerCP. In FIGS. 20D-20F, the cells were stained by Brilliant Violet 510™ anti-mouse CD8a (mCD8) antibody and Brilliant Violet 421™ anti-mouse CD4 antibody (mCD4).

FIGS. 21A and 21D are the results for the wildtype C57BL/6 mouse. FIGS. 21B and 21E are the results for the humanized homozygous mouse (hCD3-full version). FIGS. 21C and 21F are the results for the humanized homozygous mouse (hCD3-part version). In FIGS. 21A-21C, the cells were stained by Brilliant Violet 605™ anti-mouse CD19 Antibody (mCD19) and mTcRβ PerCP. In FIGS. 21D-21F, the cells were stained by PerCP anti-mouse CD3ε Antibody (mCD3) and mTcRβ PerCP.

FIGS. 22A and 22D are the results for the wildtype C57BL/6 mouse. FIGS. 22B and 22E are the results for the humanized homozygous mouse (hCD3-full version). FIGS. 22C and 22F are the results for the humanized homozygous mouse (hCD3-part version). In FIGS. 22A-22C, the cells were stained by APC anti-human CD3 Antibody (hCD3) and mTcRβ PerCP. In FIGS. 22D-22F, the cells were stained by Brilliant Violet 510™ anti-mouse CD8a (mCD8) antibody and Brilliant Violet 421™ anti-mouse CD4 antibody (mCD4).

FIGS. 23A and 23D are the results for the wildtype C57BL/6 mouse. FIGS. 23B and 23E are the results for the humanized homozygous mouse (hCD3-full version). FIGS. 23C and 23F are the results for the humanized homozygous mouse (hCD3-part version). In FIGS. 23A-23C, the cells were stained by Brilliant Violet 605™ anti-mouse CD19 Antibody (mCD19) and mTcRβ PerCP. In FIGS. 23D-23F, the cells were stained by PerCP anti-mouse CD3ε Antibody (mCD3) and mTcRβ PerCP.

FIGS. 24A and 24D are the results for the wildtype C57BL/6 mouse. FIGS. 24B and 24E are the results for the humanized homozygous mouse (hCD3-full version). FIGS. 24C and 24F are the results for the humanized homozygous mouse (hCD3-part version). In FIGS. 24A-24C, the cells were stained by APC anti-human CD3 Antibody (hCD3) and mTcRβ PerCP. In FIGS. 24D-24F, the cells were stained by Brilliant Violet 510™ anti-mouse CD8a (mCD8) antibody and Brilliant Violet 421™ anti-mouse CD4 antibody (mCD4).

FIG. 30 shows the alignment between mouse CD3e amino acid sequence (NP_031674.1; SEQ ID NO: 5) and human CD3e amino acid sequence (NP_000724.1; SEQ ID NO: 7).

DETAILED DESCRIPTION

Figure 1:
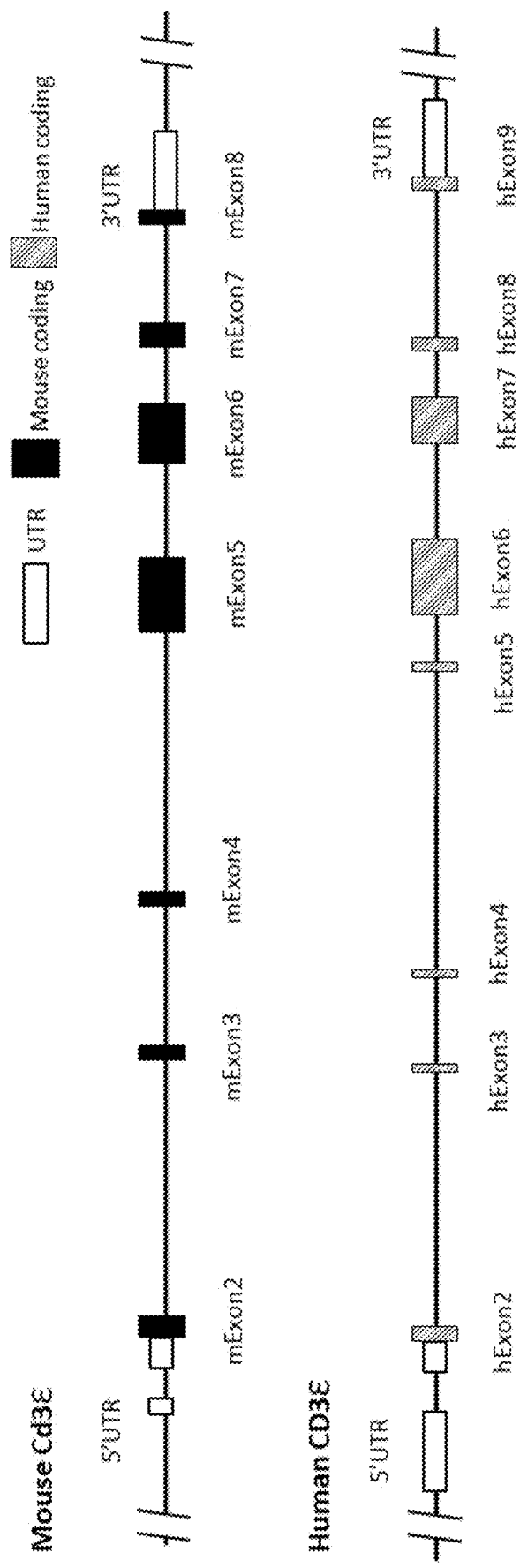
FIG. 1 is a schematic diagram showing mouse CD3e gene and human CD3e gene.

Autoimmune processes are related to defects in immunologic tolerance, a state of immune system unresponsiveness to an antigen. Tolerance is maintained by multiple mechanisms including deletion, anergy, and active cellular regulation and strategies to induce immune tolerance are being developed for the treatment of autoimmunity.

CD3 (cluster of differentiation 3) is a T cell co-receptor that is involved in activating both the cytotoxic T cell (CD8+ naive T cells) and also T helper cells (CD4+ naive T cells). Depending on the conditions used, antibodies against CD3 can either stimulate T cells to divide or inhibit the development of effector functions such as cytotoxicity. Anti-CD3 antibody therapy has a demonstrated potential in the context of treating autoimmune diseases. However, the efficacy of anti-CD3 therapy has been limited by in vivo toxicities. A well-known anti-CD3 antibody, OKT3, is used routinely in clinical therapy of transplant rejection but is known to mediate dramatic cytokine release in vivo, leading to a "flu-like" syndrome. This effect has been identified with a humoral response against the OKT3 molecule as well as a release of pro-inflammatory cytokines such as TNF-α. These physiological toxicities restrict the dosage regimens available to patients with anti-CD3 therapy and limit the overall efficacy of anti-CD3 treatment of autoimmune disease.

Experimental animal models are an indispensable research tool for studying the effects of these CD3 targeting therapies (e.g., anti-CD3e antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullis et al U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

CD3 and CD3e

Cluster of differentiation 3 (CD3) is a multimeric protein complex, known historically as the T3 complex, and is composed of four distinct polypeptide chains; epsilon (ε), gamma (γ), delta (δ) and zeta (ζ), that assemble and function as three pairs of dimers (εγ, εδ, ζζ). The CD3 complex serves as a T cell co-receptor that associates noncovalently with the T cell receptor (TCR). The CD3 protein complex is a defining feature of the T cell lineage, therefore anti-CD3 antibodies can be used effectively as T cell markers.

Ligation of the TCR/CD3 results in activation of src and syk family PTKs associated with the intracellular CD3 domains that then activate PLC and Ras-dependent pathways. However, signaling via the TCR complex is not a linear event starting at the receptor and ending in the nucleus. Instead, there appears to be complex feedback and feedforward regulation at each step.

Because CD3 is required for T cell activation, drugs (often monoclonal antibodies) that target it are being investigated as immunosuppressant therapies (e.g., otelixizumab) for graft vs host disease, and various autoimmune diseases (e.g., arthritis, type 1 diabetes). CD3e (or CD3ε) is a non-glycosylated polypeptide chain of 20 kDa. The existence of an epitope on the ε polypeptide that is conserved among many species has made it as a preferable target for antibodies that target CD3.

Therapeutic anti-CD3e antibodies bind to the epsilon chain of the CD3/TCR complex that characterizes T lymphocytes. Several nonmutually exclusive mechanisms have been proposed to explain the therapeutic effect of anti-CD3e antibodies. After a short lasting capping of the CD3 complex, the CD3/T-cell receptor complex disappears from the cell surface by internalization or shedding, a process called antigenic modulation that renders T cells temporarily blind to their cognate antigens. Anti-CD3e antibody-induced signaling can also preferentially induce anergy or apoptosis in activated T cells while sparing Tregs. Heterogeneity of TCR expression by different T-cell subsets might explain the differential effect of anti-CD3e antibody on effector versus regulatory or naïve T cells.

The tolerogenic function of anti-CD3e antibody is independent of effector functions that are linked to the Fc region of the antibody, such as complement-dependent cytotoxicity (CDC), antibody-dependent cellular cytotoxicity (ADCC)

and antibody-dependent cell phagocytosis (ADCP), as F(ab')2 fragments are sufficient for tolerance induction. It has been shown that T cells become rapidly activated in response to intravenous anti-CD3e antibody as measured by increased expression of CD69 and CD25 and serum concentrations of TGF-β and IFN-γ briefly after injection, even when using nonmitogenic anti-CD3e antibody. The direct effects of anti-CD3e antibody on T cells (capping, antigenic modulation, induction of apoptosis and anergy) are all short-term and are gone after clearance of the antibody from the circulation. Yet, the pharmacological effects mediated by anti-CD3e antibody therapy can be long lasting, indicating that additional and more durable mechanisms are involved in anti-CD3e antibody mediated tolerance. Evidence suggests a link between anti-CD3e antibody-induced apoptosis, phagocytosis of the resulting apoptotic bodies by macrophages and a subsequent increase of TGF-β. TGF-β plays an essential role in regulating immune responses and the production of TGF-β is crucial for the therapeutic effect of anti-CD3e antibody. TGF-β has pleiotropic effects on the adaptive immunity, including induction of adaptive FoxP3+ Tregs, inhibition of T-cell activation and proliferation and blocking dendritic cell maturation, and all these outcomes are observed after anti-CD3e antibody mediated tolerance induction. Indeed, it has been demonstrated that anti-CD3e antibody therapy increases TGF-β dependent Tregs, renders effector T cells more susceptible to TGF-β mediated regulation and confers a tolerogenic phenotype to dendritic cells.

A detailed description of CD3e, and the use of anti-CD3e antibodies to treat various diseases are described, e.g., in Smith-Garvin, et al. "T cell activation." Annual review of immunology 27 (2009): 591-619; Kuhn, et al. "Therapeutic anti-CD3 monoclonal antibodies: from bench to bedside." Immunotherapy 8.8 (2016): 889-906; US 20060275292; and US 20070292416; each of which is incorporated by reference in its entirety.

Figures 3A, 3B:
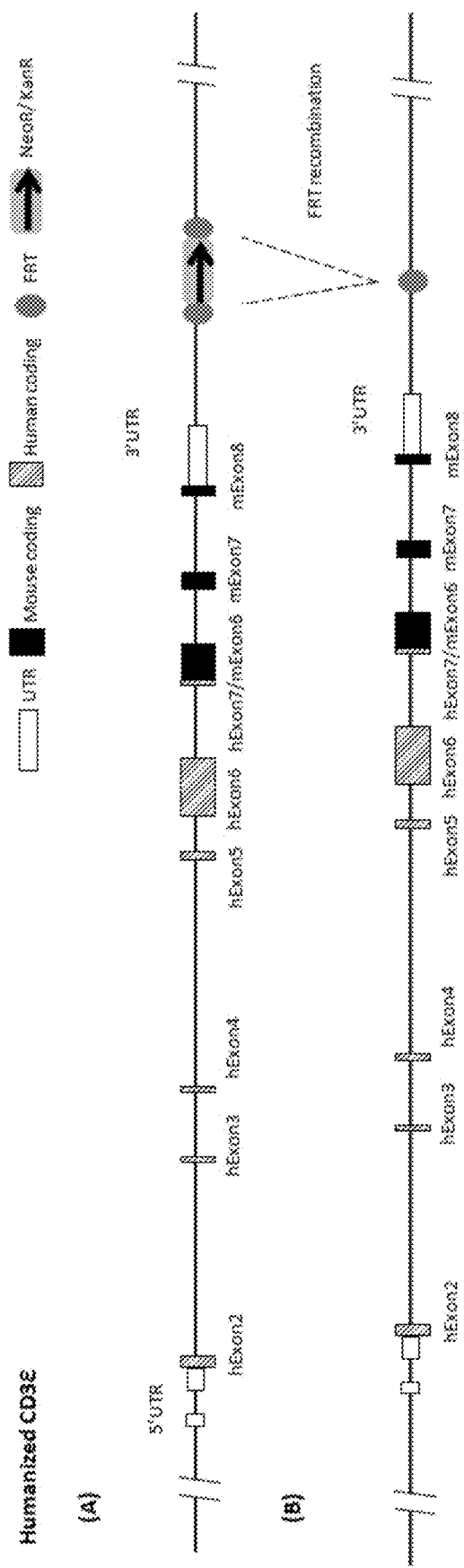
FIGS. 3A-3B show a map of humanized CD3e gene in mouse and the FRT recombination process.

In human genomes, CD3e gene (Gene ID: 916) locus has nine exons, exon 1, exon 2, exon 3, exon 4, exon 5, exon 6, exon 7, exon 8, and exon 9 (FIG. 3). The CD3e protein also has an extracellular region, a transmembrane region, and a cytoplasmic region, and the signal peptide is located at the extracellular region of CD3e. The nucleotide sequence for human CD3e mRNA is NM 000733.3 (SEQ ID NO: 6), and the amino acid sequence for human CD3e is NP_000724.1 (SEQ ID NO: 7). The location for each exon and each region in human CD3e nucleotide sequence and amino acid sequence is listed below:

TABLE 1

| Human CD3e (approximate location) | NM_000733.3 1534 bp (SEQ ID NO: 6) | NP_000724.1 207aa (SEQ ID NO: 7) |
|---|---|---|
| Exon 1 | 1-197 (Non-coding) | Non-coding |
| Exon 2 | 198-305 | 1-16 |
| Exon 3 | 306-326 | 17-23 |
| Exon 4 | 327-341 | 24-28 |
| Exon 5 | 342-359 | 29-34 |
| Exon 6 | 360-608 | 35-117 |
| Exon 7 | 609-776 | 118-173 |
| Exon 8 | 777-823 | 174-189 |
| Exon 9 | 824-1513 | 190-207 |
| Signal peptide | 257-322 | 1-22 |
| Extracellular region (excluding signal peptide region) | 323-634 | 23-126 |
| Transmembrane region | 635-712 | 127-152 |
| Cytoplasmic region | 713-877 | 152-207 |
| Donor region in Example (partial replacement; hCD3-part version) | 257-634 | 1-126 |
| Donor region in Example (full length replacement; hCD3-full version) | 257-880 | 1-207 |

In mice, CD3e gene locus has eight exons, exon 1, exon 2, exon 3, exon 4, exon 5, exon 6, exon 7, and exon 8 (FIG. 1). The mouse CD3e protein also has an extracellular region, a transmembrane region, and a cytoplasmic region, and the signal peptide is located at the extracellular region of CD3e. The nucleotide sequence for mouse CD3e cDNA is NM_007648.4 (SEQ ID NO: 4), the amino acid sequence for mouse CD3e is NP_031674.1 (SEQ ID NO: 5). The location for each exon and each region in the mouse CD3e nucleotide sequence and amino acid sequence is listed below:

TABLE 2

| Mouse CD3e (approximate location) | NM_007648.4 1436 bp (SEQ ID NO: 4) | NP_031674.1 189 aa (SEQ ID NO: 5) |
|---|---|---|
| Exon 1 | 1-25(Non-coding) | Non-coding |
| Exon 2 | 26-127 | 1-16 |
| Exon 3 | 128-145 | 17-22 |
| Exon 4 | 146-160 | 23-27 |
| Exon 5 | 161-376 | 28-99 |
| Exon 6 | 377-544 | 100-155 |
| Exon 7 | 545-591 | 156-171 |
| Exon 8 | 592-1436 | 172-189 |
| Signal peptide | 79-141 | 1-21 |
| Extracellular region (excluding signal peptide region) | 145-402 | 23-108 |
| Transmembrane region | 403-480 | 109-134 |
| Cytoplasmic region | 481-645 | 135-189 |
| Replaced region in Example (partial replacement; hCD3-part version) | 79-402 | 1-108 |
| Replaced region in Example (full length replacement; hCD3-full version) | 79-648 | 1-189 |

The mouse CD3e gene (Gene ID: 12501) is located in Chromosome 9 of the mouse genome, which is located from 44998735 to 45009664, of NC_000075.6 GRCm38.p4 (GCF_000001635.24). The 5'-UTR is from 45,009,613 to 45,009,566 and 45,009,449 to 45,009,398, exon 1 is from 45,009,613 to 45,009,566, the first intron is from 45,009,565 to 45,009,450, exon 2 is from 45,009,449 to 45,009,348, the second intron is from 45,009,347 to 45,007,194, exon 3 is from 45,007,193 to 45,007,176, the third intron is from 45,007,175 to 45,005,527, exon 4 is from 45,005,526 to 45,005,512, the fourth intron is from 145,005,511 to 45,002,354, exon 5 is from 45,002,353 to 45,002,138, the fifth intron is from 45,002,137 to 45,001,147, exon 6 is from 45,001,1476 to 45,000,979, the sixth intron is from 45,000,978 to 45,000,482, exon 7 is from 45,000,481 to 45,000,435, the seventh intron is from 45,000,434 to 44,999,588, exon 8 is from 44,999,587 to 44,998,740, and the 3'-UTR is from 44,999,530 to 44,998,740, based on transcript NM_007648.4. All relevant information for mouse CD3e locus can be found in the NCBI website with Gene ID: 12501, which is incorporated by reference herein in its entirety.

FIG. 30 shows the alignment between mouse CD3e amino acid sequence (NP_031674.1; SEQ ID NO: 5) and human CD3e amino acid sequence (NP_000724.1; SEQ ID NO: 7). Thus, the corresponding amino acid residue or region between human and mouse CD3e can be found in FIG. 30.

CD3e genes, proteins, and locus of the other species are also known in the art. For example, the gene ID for CD3e in *Rattus norvegicus* is 315609, the gene ID for CD3e in *Macaca mulatta* (Rhesus monkey) is 699467, the gene ID for CD3e in *Canis lupus familiaris* (dog) is 442981, and the gene ID for CD3e in *Sus scrofa* (pig) is 397455. The relevant information for these genes (e.g., intron sequences, exon sequences, amino acid residues of these proteins) can be found, e.g., in NCBI database, which is incorporated by reference herein in its entirety.

The present disclosure provides human or chimeric (e.g., humanized) CD3e nucleotide sequence and/or amino acid sequences. In some embodiments, the entire sequence of mouse exon 1, exon 2, exon 3, exon 4, exon 5, exon 6, exon 7, exon 8, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, exon 8, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 500, or 600 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, signal peptide, extracellular region, transmembrane region, or cytoplasmic region. In some embodiments, a region, a portion, or the entire sequence of mouse exon 1, exon 2, exon 3, exon 4, exon 5, exon 6, exon 7, and/or exon 8 (e.g., exon 2, exon 3, exon 4, exon 5, exon 6) are replaced by the human exon 1, exon 2, exon 3, exon 4, exon 5, exon 6, exon 7, exon 8, and/or exon 9 (e.g., exon 2, exon 3, exon 4, exon 5, exon 6, exon 7) sequence.

In some embodiments, the present disclosure also provides a chimeric (e.g., humanized) CD3e nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CD3e mRNA sequence (e.g., SEQ ID NO: 4), mouse CD3e amino acid sequence (e.g., SEQ ID NO: 5), or a portion thereof (e.g., exon 2, exon 3, exon 4, exon 5, exon 6, exon 7, exon 8); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CD3e mRNA sequence (e.g., SEQ ID NO: 6), human CD3e amino acid sequence (e.g., SEQ ID NO: 7), or a portion thereof (e.g., exon 2, exon 3, exon 4, exon 5, exon 6, exon 7, exon 8, exon 9).

In some embodiments, the sequence encoding amino acids 1-108 of mouse CD3e (SEQ ID NO: 5) is replaced. In some embodiments, the sequence is replaced by a sequence encoding a corresponding region of human CD3e (e.g., amino acids 1-126 of human CD3e (SEQ ID NO: 7)).

In some embodiments, the nucleic acids as described herein are operably linked to a promotor or regulatory element, e.g., an endogenous mouse CD3e promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CD3e nucleotide sequence (e.g., exon 2, exon 3, exon 4, exon 5, exon 6 or NM_007648.4 (SEQ ID NO: 4)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CD3e nucleotide sequence (e.g., exon 1, exon 2, exon 6, exon 7, exon 8, or NM_007648.4 (SEQ ID NO: 4)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CD3e nucleotide sequence (e.g., exon 1, exon 2, exon 7, exon 8, exon 9 or NM_000733.3 (SEQ ID NO: 6)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CD3e nucleotide sequence (e.g., exon 2, exon 3, exon 4, exon 5, exon 6, exon 7, or NM_000733.3 (SEQ ID NO: 6)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CD3e amino acid sequence (e.g., exon 2, exon 3, exon 4, exon 5, exon 6 or NP_031674.1 (SEQ ID NO: 5)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CD3e amino acid sequence (e.g., exon 1, exon 2, exon 6, exon 7, exon 8, or NP_031674.1 (SEQ ID NO: 5)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CD3e amino acid sequence (e.g., exon 1, exon 2, exon 7, exon 8, exon 9 or NP_000724.1 (SEQ ID NO: 7)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CD3e amino acid sequence (e.g., exon 2, exon 3, exon 4, exon 5, exon 6, exon 7, or NP_000724.1 (SEQ ID NO: 7)).

The present disclosure also provides a humanized CD3e mouse amino acid sequence, wherein the amino acid sequence is selected from the group consisting of:

a) an amino acid sequence shown in SEQ ID NO: 10;

b) an amino acid sequence having a homology of at least 90% with or at least 90% identical to the amino acid sequence shown in SEQ ID NO: 10;

c) an amino acid sequence encoded by a nucleic acid sequence, wherein the nucleic acid sequence is able to hybridize to a nucleotide sequence encoding the amino acid shown in SEQ ID NO: 10 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 10;

e) an amino acid sequence that is different from the amino acid sequence shown in SEQ ID NO: 10 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 10.

The present disclosure also relates to a CD3e nucleic acid (e.g., DNA or RNA) sequence, wherein the nucleic acid sequence can be selected from the group consisting of:

a) a nucleic acid sequence encoding a homologous CD3e amino acid sequence of a humanized mouse;

b) a nucleic acid sequence that is shown in SEQ ID NO: 3, SEQ ID NO: 8, SEQ ID NO: 9, SEQ ID NO: 39, or SEQ ID NO: 40;

c) a nucleic acid sequence that is able to hybridize to the nucleotide sequence as shown in SEQ ID NO: 3, SEQ ID NO: 8, SEQ ID NO: 9, SEQ ID NO: 39, or SEQ ID NO: 40 under a low stringency condition or a strict stringency condition;

d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 3, SEQ ID NO: 8, SEQ ID NO: 9, SEQ ID NO: 39, or SEQ ID NO: 40;

e) a nucleic acid sequence that encodes an amino acid sequence, wherein the amino acid sequence has a homology of at least 90% with or at least 90% identical to the amino acid sequence shown in SEQ ID NO: 10;

f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 10;

g) a nucleic acid sequence that encodes an amino acid sequence, wherein the amino acid sequence is different from the amino acid sequence shown in SEQ ID NO: 10 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 10.

The present disclosure further relates to a CD3e genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 3, SEQ ID NO: 8, SEQ ID NO: 9, SEQ ID NO: 39, or SEQ ID NO: 40.

The disclosure also provides an amino acid sequence that has a homology of at least 90% with, or at least 90% identical to the sequence shown in SEQ ID NO: 10, and has protein activity. In some embodiments, the homology with the sequence shown in SEQ ID NO: 10 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 10 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 3, SEQ ID NO: 8, SEQ ID NO: 9, SEQ ID NO: 39, or SEQ ID NO: 40, and encodes a polypeptide that has protein activity. In some embodiments, the homology with the sequence shown in SEQ ID NO: 3, SEQ ID NO: 8, SEQ ID NO: 9, SEQ ID NO: 39, or SEQ ID NO: 40 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) CD3e from an endogenous non-human CD3e locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous CD3e locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized CD3e gene or a humanized CD3e nucleic acid. In some embodiments, at least one or more portions of the gene or the nucleic acid is from the human CD3e gene, at least one or more portions of the gene or the nucleic acid is from a non-human CD3e gene. In some embodiments, the gene or the nucleic acid comprises a sequence that encodes a CD3e protein. The encoded CD3e protein is functional or has at least one activity of the human CD3e protein or the non-human CD3e protein, e.g., associate with human or endogenous CD3 gamma ($\gamma$), delta ($\delta$) and/or zeta ($\zeta$) polypeptide, form a T cell co-receptor, or associate with human or endogenous T cell receptor, activating T cell (e.g., inducing T cell division), increasing CD3 expression, increasing expression of CD69 and/or CD25, increasing production of proinflammatory cytokines, inducing activation and proliferation of immune cells, increasing the production of cytokines (e.g., TGF-$\beta$ and IFN-$\gamma$), and/or upregulating the immune response.

In some embodiments, the chimeric protein or the chimeric polypeptide is a humanized CD3e protein or a humanized CD3e polypeptide. In some embodiments, at least one or more portions of the amino acid sequence of the protein or the polypeptide is from a human CD3e protein, and at least one or more portions of the amino acid sequence of the protein or the polypeptide is from a non-human CD3e protein. The humanized CD3e protein or the humanized CD3e polypeptide is functional or has at least one activity of the human CD3e protein or the non-human CD3e protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized CD3e animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human CD3e locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature CD3e coding sequence with human mature CD3e coding sequence.

Genetically modified non-human animals that comprise a modification of an endogenous non-human CD3e locus. In some embodiments, the modification can comprise a human nucleic acid sequence encoding at least a portion of a mature CD3e protein (e.g., at least 10%, 20%, 30%, 40%, 50%, 60%, 70%, 80%, 90%, 95%, 96%, 97%, 98%, or 99% identical to the mature CD3e protein sequence). Although genetically modified cells are also provided that can comprise the modifications described herein (e.g., ES cells, somatic cells), in many embodiments, the genetically modified non-human animals comprise the modification of the endogenous CD3e locus in the germline of the animal.

Genetically modified animals can express a human CD3e and/or a chimeric (e.g., humanized) CD3e from endogenous mouse loci, wherein the endogenous mouse CD3e gene has been replaced with a human CD3e gene and/or a nucleotide sequence that encodes a region of human CD3e sequence or an amino acid sequence that is at least 10%, 20%, 30%, 40%, 50%, 60%, 70%, 80%, 90%, 95%, 96%, 97%, 98%, or 99% identical to the human CD3e sequence. In various embodiments, an endogenous non-human CD3e locus is modified in whole or in part to comprise human nucleic acid sequence encoding at least one protein-coding sequence of a mature CD3e protein.

In some embodiments, the genetically modified mice express the human CD3e and/or chimeric CD3e (e.g., humanized CD3e) from endogenous loci that are under control of mouse promoters and/or mouse regulatory elements. The replacement(s) at the endogenous mouse loci provide non-human animals that express human CD3e or chimeric CD3e (e.g., humanized CD3e) in appropriate cell types and in a manner that does not result in the potential pathologies observed in some other transgenic mice known in the art. The human CD3e or the chimeric CD3e (e.g., humanized CD3e) expressed in animal can maintain one or more functions of the wildtype mouse or human CD3e in the animal. For example, human or non-human CD3e can form T cell co-receptor, and then interact with T cell receptor. Upon binding with antigens presented by major histocompatibility complex I (MHC I) or MHCII, the T cell receptor with its co-receptor can upregulate immune response, e.g., upregulate immune response by at least 10%, 20%, 30%, 40%, or 50%. Furthermore, in some embodiments, the animal does not express endogenous CD3e. As used herein, the term "endogenous CD3e" refers to CD3e protein that is expressed from an endogenous CD3e nucleotide sequence of the non-human animal (e.g., mouse) before any genetic modification.

The genome of the animal can comprise a sequence encoding an amino acid sequence that is at least 50%, 60%, 70%, 75%, 80%, 85%, 90%, 95%, 99%, or 100% identical to human CD3e (NP_000724.1) (SEQ ID NO: 7). In some embodiments, the genome comprises a sequence encoding an amino acid sequence that is at least 50%, 60%, 70%, 75%, 80%, 85%, 90%, 95%, 99%, or 100% identical to SEQ ID NO: 10.

The genome of the genetically modified animal can comprise a replacement at an endogenous CD3e gene locus of a sequence encoding a region of endogenous CD3e with a sequence encoding a corresponding region of human CD3e. In some embodiments, the sequence that is replaced is any sequence within the endogenous CD3e gene locus, e.g., exon 1, exon 2, exon 3, exon 4, exon 5, exon 6, exon 7, exon 8, 5'-UTR, 3'-UTR, the first intron, the second intron, and the third intron, the fourth intron, the fifth intron, the sixth intron, the seventh intron, etc. In some embodiments, the sequence that is replaced is within the regulatory region of the endogenous CD3e gene. In some embodiments, the sequence that is replaced is exon 2, exon 3, exon 4, exon 5, exon 6 or part thereof, of an endogenous mouse CD3e gene locus.

The genetically modified animal can have one or more cells expressing a human or chimeric CD3e (e.g., humanized CD3e) having an extracellular region and a cytoplasmic region, wherein the extracellular region comprises a sequence that is at least 50%, 60%, 70%, 80%, 90%, 95%, 99% identical to the extracellular region of human CD3e. In some embodiments, the extracellular region of the humanized CD3e has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human CD3e. Because human CD3e and non-human CD3e (e.g., mouse CD3e) sequences, in many cases, are different, antibodies that bind to human CD3e will not necessarily have the same binding affinity with non-human CD3e or have the same effects to non-human CD3e. Therefore, the genetically modified animal having a human or a humanized extracellular region can be used to better evaluate the effects of anti-human CD3e antibodies in an animal model. In some embodiments, the genome of the genetically modified animal comprises a sequence encoding an amino acid sequence that corresponds to part or the entire sequence of exon 2, exon 3, exon 4, exon 5, exon 6, and/or exon 7 of human CD3e, part or the entire sequence of extracellular region of human CD3e (with or without signal peptide), or part or the entire sequence of amino acids 1-126 of SEQ ID NO: 7.

In some embodiments, the non-human animal can have, at an endogenous CD3e gene locus, a nucleotide sequence encoding a human CD3e or a chimeric human/non-human CD3e polypeptide, wherein a human portion of the chimeric human/non-human CD3e polypeptide comprises a portion of human CD3e extracellular domain, and wherein the animal expresses a functional CD3e on a surface of a cell of the animal. The human portion of the chimeric human/non-human CD3e polypeptide can comprise a portion of exon 2, exon 3, exon 4, exon 5, exon 6, and/or exon 7 of human CD3e. In some embodiments, the human portion of the chimeric human/non-human CD3e polypeptide can comprise a sequence that is at least 80%, 85%, 90%, 95%, or 99% identical to amino acids 1-126 of SEQ ID NO: 7.

In some embodiments, the non-human portion of the chimeric human/non-human CD3e polypeptide comprises transmembrane and/or cytoplasmic regions of an endogenous non-human CD3e polypeptide. There may be several advantages that are associated with the transmembrane and/or cytoplasmic regions of an endogenous non-human CD3e polypeptide. For example, once CD3e forms a CD3 co-receptor complex, it can properly transmit extracellular signals into the cells and initiate the downstream pathway. A human or humanized transmembrane and/or cytoplasmic regions may not function properly in non-human animal cells. In some embodiments, a few extracellular amino acids that are close to the transmembrane region of CD3e are also derived from endogenous sequence. These amino acids can also be important for transmembrane signal transmission. In some embodiments, the chimeric human/non-human CD3e is functional. In some embodiments, the non-human animal with chimeric human/non-human CD3e is healthy (e.g., without any obvious change in body weight or size of organs, such as thymus).

Furthermore, the genetically modified animal can be heterozygous with respect to the replacement at the endogenous CD3e locus, or homozygous with respect to the replacement at the endogenous CD3e locus.

In some embodiments, the humanized CD3e locus lacks a human CD3e 5'-UTR. In some embodiment, the humanized CD3e locus comprises a rodent (e.g., mouse) 5'-UTR. In some embodiments, the humanization comprises a human 3'-UTR. In appropriate cases, it may be reasonable to presume that the mouse and human CD3e genes appear to be similarly regulated based on the similarity of their 5'-flanking sequence. As shown in the present disclosure, humanized CD3e mice that comprise a replacement at an endogenous mouse CD3e locus, which retain mouse regulatory elements but comprise a humanization of CD3e encoding sequence, do not exhibit obvious pathologies. Both genetically modified mice that are heterozygous or homozygous for humanized CD3e are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized CD3e gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized CD3e in the genome of the animal.

Figure 2:
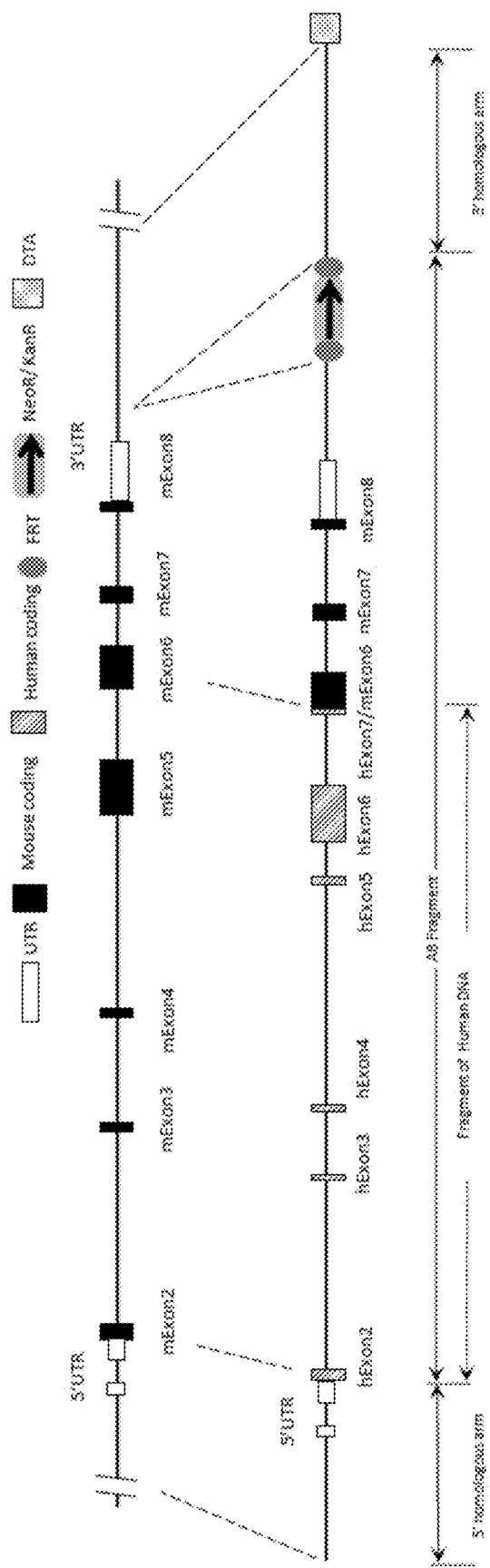
FIG. 2 is a schematic diagram showing a gene targeting strategy to replace part of mouse CD3e coding sequence with human CD3e coding sequence.
Figure 7:
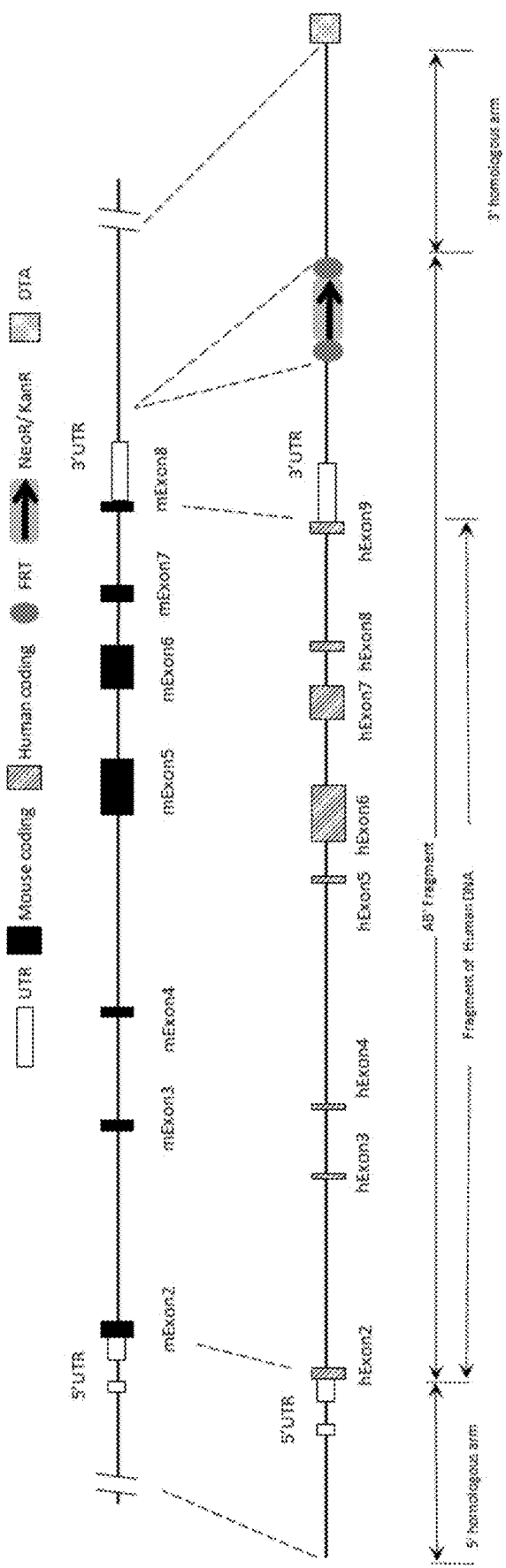
FIG. 7 is a schematic diagram showing a gene targeting strategy to replace the entire mouse CD3e coding sequence with human CD3e coding sequence.

In some embodiments, the non-human mammal comprises the genetic construct as described herein (e.g., gene construct as shown in FIG. 2 or FIG. 7). In some embodiments, a non-human mammal expressing human or humanized CD3e is provided. In some embodiments, the tissue-specific expression of human or humanized CD3e protein is provided.

In some embodiments, the expression of human or humanized CD3e in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human CD3e protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized CD3e protein.

Vectors

The present disclosure relates to a targeting vector, comprising: a) a DNA fragment homologous to the 5' end of a region to be altered (5' arm), which is selected from the CD3e gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD3e gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000075.6; c) the DNA fragment homologous to the 3' end of the region to be altered (3' arm) is selected from the nucleotide sequences that have at least 90% homology to the NCBI accession number NC_000075.6.

In some embodiments, a) the DNA fragment homologous to the 5' end of a region to be altered (5' arm) is selected from the nucleotides from the position 45014642 to the position 45009397 of the NCBI accession number NC_000075.6; c) the DNA fragment homologous to the 3' end of the region to be altered (3' arm) is selected from the nucleotides from the position 44998440 to the position 44994894 of the NCBI accession number NC_000075.6.

In some embodiments, the length of the selected genomic nucleotide sequence in the targeting vector can be more than about 3 kb, about 3.5 kb, about 4 kb, about 4.5 kb, about 5 kb, about 5.5 kb, or about 6 kb.

In some embodiments, the region to be altered is exon 1, exon 2, exon 3, exon 4, exon 5, exon 6, exon 7, and/or exon8 of CD3e gene (e.g., exon 2, exon 3, exon 4, exon 5, and/or exon 6 of mouse CD3e gene).

The targeting vector can further include a selected gene marker.

In some embodiments, the sequence of the 5' arm is shown in SEQ ID NO: 1; and the sequence of the 3' arm is shown in SEQ ID NO: 2. In some embodiments, the sequence of the 5' arm is shown in SEQ ID NO: 37. In some embodiments, the sequence of the 3' arm is shown in SEQ ID NO: 38.

In some embodiments, the sequence is derived from human (e.g., 118304953-118313732 of NC_000011.10 (SEQ ID NO: 3) or 118304953-118315542 of NC_000011.10 (SEQ ID NO: 39)). For example, the target region in the targeting vector is a part or entirety of the nucleotide sequence of a human CD3e, preferably exon 2, exon 3, exon 4, exon 5, exon 6, and/or exon 7 of the human CD3e. In some embodiments, the nucleotide sequence of the humanized CD3e encodes the entire or the part of human CD3e protein with the NCBI accession number NP_000724.1 (SEQ ID NO: 7).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous CD3e gene locus, a sequence encoding a region of an endogenous CD3e with a sequence encoding a corresponding region of human or chimeric CD3e. In some embodiments, the replacement occurs in a germ cell, a somatic cell, a blastocyst, or a fibroblast, etc. The nucleus of a somatic cell or the fibroblast can be inserted into an enucleated oocyte.

FIGS. 2 and 7 show humanization strategies for a mouse CD3e locus. In FIGS. 2 and 7, the targeting strategy involves a vector comprising the 5' end homologous arm, human CD3e gene fragment, 3' homologous arm. The process can involve replacing endogenous CD3e sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous CD3e sequence with human CD3e sequence.

Thus, in some embodiments, the methods for making a genetically modified, humanized animal, can include the step of replacing at an endogenous CD3e locus (or site), a nucleic acid encoding a sequence encoding a region of endogenous CD3e with a sequence encoding a corresponding region of human CD3e. The sequence can include a region (e.g., a part or the entire region) of exon 1, exon 2, exon 3, exon 4, exon 5, exon 6, exon 7, exon 8, and/or exon 9 of a human CD3e gene. In some embodiments, the sequence includes a region of exon 2, exon 3, exon 4, exon 5, exon 6, and exon 7 of a human CD3e gene (e.g., amino acids 1-126 of SEQ ID NO: 7). In some embodiments, the sequence includes a region of exon 2, exon 3, exon 4, exon 5, exon 6, exon 7, exon 8, and exon 9 of a human CD3e gene. In some embodiments, the region is located within the extracellular region of CD3e. In some embodiments, the endogenous CD3e locus is exon 2, exon 3, exon 4, exon 5, and/or exon 6 of mouse CD3e.

In some embodiments, the methods of modifying a CD3e locus of a mouse to express a chimeric human/mouse CD3e peptide can include the steps of replacing at the endogenous mouse CD3e locus a nucleotide sequence encoding a mouse CD3e with a nucleotide sequence encoding a human CD3e, thereby generating a sequence encoding a chimeric human/mouse CD3e.

In some embodiments, the nucleotide sequence encoding the chimeric human/mouse CD3e can include a first nucleotide sequence encoding an extracellular region of mouse CD3e (with or without the mouse or human signal peptide sequence); a second nucleotide sequence encoding an extracellular region of human CD3e; a third nucleotide sequence encoding a transmembrane and a cytoplasmic region of a mouse CD3e.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a CD3e gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized CD3e protein, e.g., in a physiologically appropriate manner, provide a variety of uses that include, but are not limited to, developing therapeutics for human diseases and disorders, and assessing the toxicity and/or the efficacy of these human therapeutics in the animal models.

In various aspects, genetically modified animals are provided that express human or humanized CD3e, which are useful for testing agents that can decrease or block the interaction between T cell receptor and/or co-receptor with its ligands, testing the interaction between CD3e (or CD3) and anti-human CD3e antibodies, testing whether an agent can increase or decrease the immune response, and/or determining whether an agent is an CD3 (or T cell receptor and/or co-receptor) agonist or antagonist. The genetically modified animals can be, e.g., an animal model of a human disease, e.g., the disease is induced genetically (a knock-in or knock-out). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-CD3e antibody for the treatment of cancer. The methods involve administering the anti-CD3e antibody (e.g., anti-human CD3e antibody) to the animal as described herein, wherein the animal has a tumor; and determining the inhibitory effects of the anti-CD3e antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-CD3e antibody prevents antigens presented by MHC from binding to T cell receptors (TCR). In some embodiments, the anti-CD3e antibody does not prevent antigens presented by MHC from binding to T cell receptors.

In some embodiments, the genetically modified animals can be used for determining whether an anti-CD3e antibody is a CD3 (or TCR) agonist or antagonist. In some embodiments, the methods as described herein are also designed to determine the effects of the agent (e.g., anti-CD3e antibodies) on CD3 (or TCR), e.g., whether the agent can stimulate immune cells or inhibit immune cells (e.g., T cells), whether the agent can increase or decrease the production of cytokines, whether the agent can activate or deactivate immune cells (e.g., T cells), whether the agent can upregulate the immune response or downregulate immune response, whether the agent can cause activation induced cell death (AICD), and/or whether the agent can induce complement mediated cytotoxicity (CMC) or antibody dependent cellular cytotoxicity (ADCC). In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups. In some embodiments, the $TGI_{TV}$ value is negative, which means that the tested agent decreases immune response, and/or promotes tumor growth.

In some embodiments, the anti-CD3e antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-CD3e antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-CD3e antibody is designed for treating hepatocellular, ovarian, colon, or cervical carcinomas. In some embodiments, the anti-CD3e antibody is designed for treating advanced breast cancer, advanced ovarian cancer, and/or advanced refractory solid tumor. In some embodiments, the anti-CD3e antibody is designed for treating metastatic solid tumors, NSCLC, melanoma, non-Hodgkin lymphoma, colorectal cancer, and multiple myeloma. In some embodiments, the anti-CD3e antibody is designed for treating melanoma, pancreatic carcinoma, mesothelioma, hematological malignancies (e.g., Non-Hodgkin's lymphoma, lymphoma, chronic lymphocytic leukemia), or solid tumors (e.g., advanced solid tumors). In some embodiments, the anti-CD3e antibody is designed for treating carcinomas (e.g., nasopharynx carcinoma, bladder carcinoma, cervix carcinoma, kidney carcinoma or ovary carcinoma).

In some embodiments, the anti-CD3e antibody is designed for treating, preventing, or reducing the risk of developing disorders associated with an abnormal or unwanted immune response, e.g., an autoimmune disorder, e.g., by affecting the functional properties of the circulating CD3+ T cells (e.g., reducing their proliferative capacity) or by inducing regulatory cells. These autoimmune disorders include, but are not limited to, Alopecia areata, lupus, ankylosing spondylitis, Meniere's disease, antiphospholipid syndrome, mixed connective tissue disease, autoimmune Addison's disease, multiple sclerosis, autoimmune hemolytic anemia, myasthenia gravis, autoimmune hepatitis, pemphigus vulgaris, Behcet's disease, pernicious anemia, bullous pemphigoid, polyarthritis nodosa, cardiomyopathy, polychondritis, celiac sprue-dermatitis, polyglandular syndromes, chronic fatigue syndrome (CFIDS), polymyalgia rheumatica, chronic inflammatory demyelinating, polymyositis and dermatomyositis, chronic inflammatory polyneuropathy, primary agammaglobulinemia, Churg-Strauss syndrome, primary biliary cirrhosis, cicatricial pemphigoid, psoriasis, CREST syndrome, Raynaud's phenomenon, cold agglutinin disease, Reiter's syndrome, Crohn's disease, Rheumatic fever, discoid lupus, rheumatoid arthritis, Cryoglobulinemia sarcoidosis, fibromyalgia, scleroderma, Grave's disease, Sjögren's syndrome, Guillain-Barre, stiffman syndrome, Hashimoto's thyroiditis, Takayasu arteritis, idiopathic pulmonary fibrosis, temporal arteritis/giant cell arteritis, idiopathic thrombocytopenia purpura (ITP), ulcerative colitis, IgA nephropathy, uveitis, diabetes (e.g., Type I), vasculitis, lichen planus, and vitiligo. The anti-CD3e antibodies or antigen-binding fragments thereof can also be administered to a subject to treat, prevent, or reduce the risk of developing disorders associated with an abnormal or unwanted immune response associated with cell, tissue or organ transplantation, e.g., renal, hepatic, and cardiac transplantation, e.g., graft versus host disease (GVHD), or to prevent allograft rejection. In some embodiments, the subject has Crohn's disease, ulcerative colitis or type 1 diabetes. Thus, the methods as described herein can be used to determine the effectiveness of an anti-CD3e antibody in inhibiting immune response, and the animals can be used as models for testing agents for treating these autoimmune diseases.

The present disclosure also provides methods of determining toxicity of an antibody (e.g., anti-CD3e antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the CD3e gene function, human CD3e antibodies, drugs for human CD3e targeting sites, the drugs or efficacies for human CD3e targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric CD3e gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), TNF Receptor Superfamily Member 4 (TNFRSF4 or OX40), CD3δ, CD3γ, CD40, Inducible T-cell COStimulator (ICOS or CD278) or Signal regulatory protein a (SIRPα).

The methods of generating genetically modified animal model with two or more human or chimeric genes (e.g., humanized genes) can include the following steps:

(a) using the methods of introducing human CD3e gene or chimeric CD3e gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, CD47, CD137, CD154, TIGIT, TIM-3, GITR, SIRPα, OX40, CD3δ, CD3γ, CD40, or CD278. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/120388, PCT/CN2018/081628, PCT/CN2018/081629; each of which is incorporated herein by reference in its entirety.

In some embodiments, the CD3e humanization is directly performed on a genetically modified animal having a human or chimeric PD-1, CTLA-4, BTLA, PD-L1, CD27, CD28, CD47, CD137, CD154, TIGIT, TIM-3, GITR, OX40, SIRPα, CD3δ, CD3γ, CD40, or CD278 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-CD3e antibody and an additional therapeutic agent for the treatment of cancer. The methods include administering the anti-CD3e antibody and the additional therapeutic agent to the animal, wherein the animal has a tumor; and determining the inhibitory effects of the combined treatment to the tumor. In some embodiments, the additional therapeutic agent is an antibody that specifically binds to PD-1, CTLA-4, BTLA, PD-L1, CD27, CD28, CD47, CD137, CD154, TIGIT, TIM-3, GITR, OX40, CD3δ, CD3γ, CD40, SIRPα or CD278. In some embodiments, the additional therapeutic agent is an anti-CTLA4 antibody (e.g., ipilimumab), an anti-PD-1 antibody (e.g., nivolumab), or an anti-PD-L1 antibody.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various autoimmune diseases as described herein.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.
Materials and Methods The following materials were used in the following examples.

C57BL/6 mice and Flp recombinase transgenic mice were purchased from the China Food and Drugs Research Institute National Rodent Experimental Animal Center.

BALB/c mice were obtained from Beijing Vital River Laboratory Animal Technology Co., Ltd.

BAC clones were purchased from Invitrogen (Catalog number: RPCI23.0 (Clone ID: 140I1) and RPCI11.0 (Clone ID: 414G21)).

Reverse Transcription Kit was obtained from Takara (Catalog number: 6110A).

AIO kit was obtained from Beijing Biocytogen Co., Ltd. (Catalog number: BCG-DX-004).

*E. coli* TOP10 competent cells were purchased from the Tiangen Biotech (Beijing) Co. (Catalog number: CB104-02).

BamHI, HindIII, XhoI, EcoRI, EcoRV, NotI, NdeI, SalI, ScaI, and SwaI restriction enzymes were purchased from NEB (Catalog numbers: R3136M, R3104M, R0146S, R3101M, R0195S, R3189M, R0111S, R3138M, R3122M, and R0604S).

APC anti-mouse CD69 antibody (mCD69 APC) was purchased from Biolegend (Catalog number: 104514).

PE anti-mouse CD25 antibody (mCD25 PE) was purchased from Biolegend (Catalog number: 102008).

APC anti-mouse CD3e (145-2C11) antibody was purchased from TonBo Biosciences (Catalog number: 20-0031-U025).

OKT3 huCD3 Mouse/IgG2a (OKT-3) was purchased from BioXcell (Catalog number: BE0001-2).

PerCP anti-mouse CD3e Antibody (mCD3 PerCP) was purchased from Biolegend (Catalog number: 100326).

PerCP/Cy55 anti-mouse TCR beta chain antibody (mTcRβ PerCP) was obtained from Biolegend (Catalog number: 109228).

PerCP anti-human CD3 Antibody (hCD3 PerCP) was obtained from Biolegend (Catalog number: 300428).

BV711 hamster anti-mouse CD3e (mCD3) was obtained from BD Biosciences (Catalog number: 563123).

G418 medium was obtained from Thermo Fisher (Catalog number: 11811023).

Brilliant Violet 421™ anti-mouse CD4 antibody was obtained from Biolegend (Catalog number: 100438).

Brilliant Violet 510™ anti-mouse CD8a antibody was obtained from Biolegend (Catalog number: 100751).

Brilliant Violet 605™ anti-mouse CD19 antibody was obtained from Biolegend (Catalog number: 115540).

APC anti-human CD3 Antibody (mCD3e) was obtained from Biolegend (Catalog number: 300312).

FITC anti-mouse TCR β chain antibody was obtained from Biolegend (Catalog number: 109205).

InVivoMAb anti-mouse PD-1 (CD279) was obtained from BioXCell (Catalog number: BE0146).

Human IgG was obtained from Beijing Dingguo Changsheng Biotechnology Co., Ltd. (Catalog number: AG-0012).

Example 1: Vector Design

The targeting strategy of the partial sequence replacement of the CD3e gene is shown in FIG. 2. The targeting vector comprises a 5' homology arm (SEQ ID NO: 1), a 3' homology arm (SEQ ID NO: 2) and a human DNA fragment (SEQ ID NO: 3). The neomycin-resistance (neo) gene and/or Kanamycin resistance gene (KanR) was added to the vector and is flanked by two FLP recombinase target (FRT) sequences or LoxP sequences.

A negative selection marker, such as Diphtheria toxin A (DTA), was also added to the downstream of the 3' homologous arm of the recombinant vector. FIG. 3 is a schematic representation of the humanized mouse CD3e gene and the FRT recombination process. Mouse CD3e (based on the transcript of NM_007648.4→NP_031674.1, the mRNA sequence is shown in SEQ ID NO: 4, and the corresponding protein sequence is shown in SEQ ID NO: 5) has 8 exons. Exon 1 does not encode any amino acid sequence and part of exon 2 encodes some amino acid sequences. In this example, portions of mouse exons 2-6 were replaced by the corresponding human CD3e gene sequence (portions of exons 2-7). The human CD3e gene sequence is based on the transcript of NM_000733.3→NP_000724.1. The mRNA sequence of human CD3e is shown in SEQ ID NO: 6, and the corresponding protein sequence is shown in SEQ ID: NO: 7.

The CDS sequence, the mRNA sequence and the encoded amino acid sequence of the humanized mouse CD3e gene are shown in SEQ ID NO: 8, SEQ ID NO: 9, and SEQ ID NO: 10, respectively.

Example 2: Primers and PCR Amplification

Primers for amplifying 7 homologous recombination fragments (A1, A2-1, A2-2, A3, B, C1, C2) were designed and the primer sequences are shown in the table below.

TABLE 3

| Fragments | Length (bp) | Primer sequence (5'-3') |
|---|---|---|
| A1 | 514 bp | F: cgatctcgagagtactgagtgcttcaacgtcttc (SEQ ID NO: 11) R: gtgcccgactgcatcctctcagaatgctctctacc (SEQ ID NO: 12) |

TABLE 3-continued

| Fragments | Length (bp) | Primer sequence (5'-3') |
|---|---|---|
| A2-1 | 508 bp | F: gcattctgagaggatgcagtcgggcactcactg (SEQ ID NO: 13)<br>R: gcttatgccatttaaattacgaggcgttttatggtctca (SEQ ID NO: 14) |
| A2-2 | 514 bp | F: gcctcgtaatttaaatggcataagctaaggtataataat (SEQ ID NO: 15)<br>R: ctactgctgtcagatccatctccatgcagttctc (SEQ ID NO: 16) |
| A3 | 2701 bp | F: tggagatggatctgacagcagtagccataatcatc (SEQ ID NO: 17)<br>R: cgataagcttcctggcagctgatggaaaccag (SEQ ID NO: 18) |
| B | 536 bp | F: cgatggatccagaattcaagtgctgctgaacagagccag (SEQ ID NO: 19)<br>R: cgatgcggccgcagtactcattttaacataagcatcgatgcc (SEQ ID NO: 20) |
| C1 | 525 bp | F: gctggtaccggcgcgcctcgagctcagatgttcctgcaatcatg (SEQ ID NO: 21)<br>R: gctgaatgctgatatcatgtgaggcctttaaatgtg (SEQ ID NO: 22) |
| C2 | 525 bp | F: aggcctcacatgatatcagcattcagcaagtccag (SEQ ID NO: 23)<br>R: tcctcttcagacctggcggccgcacaagaaatgtttcagatgcctttc (SEQ ID NO: 24) |

KOD-plus DNA polymerase was used to amplify the seven homologous recombination fragments. Among them, BAC clones with mouse CD3e (Catalog number: RP23-140I1; "mouse BAC clones") were used as a template for A1, A3, B, C1, C2 homologous recombination fragments, and BAC clones with human CD3e (Catalog number: RP11-414G21; "human BAC clones") were used as a template for A2-1 and A2-2 homologous recombination fragments. The conditions for the PCR amplification were shown in the tables below.

TABLE 4

| The PCR reaction system (20 μL) | |
|---|---|
| Composition | Amount |
| 10 × buffer for KOD-plus DNA polymerase | 2 μL |
| dNTP (2 mM) | 2 μL |
| MgSO$_4$ (25 mM) | 0.8 μL |
| Upstream primer F (10 μM) | 0.6 μL |
| Downstream primer R (10 μM) | 0.6 μL |
| BAC DNA templates | 50 ng |
| KOD-Plus DNA polymerase (1 U/μL) | 0.6 μL |
| H$_2$O | Add to 20 μL |

TABLE 5

| The PCR reaction conditions | | |
|---|---|---|
| Temperature | Time | Cycles |
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 57° C. | 30 sec | |
| 68° C. | 1 kb/min | |

TABLE 5-continued

| The PCR reaction conditions | | |
|---|---|---|
| Temperature | Time | Cycles |
| 68° C. | 10 min | 1 |
| 4° C. | 10 min | 1 |

The PCR products (DNA fragments) A1, A2-1, A2-2, A3, B, C1 and C2 were collected and were used to construct targeting vectors.

Example 3. Construction of Homologous Recombination Targeting Vector

The mouse CD3e gene and human CD3e gene are shown in FIG. 1. The targeting strategy is shown in FIG. 2.

Targeting Vector Construction

The targeting vector was obtained by the following steps:

(1). pBs-Neo-B plasmid was obtained by ligating fragment B and pBs-Neo vector by BamHI/NotI restriction enzymes. The sequence of pBs-Neo-B plasmid was then verified by sequencing.

(2). Fragment A1 and fragment A2-1 were ligated by overlap extension PCR (Phusion DNA Polymerases); Fragment A2-2 and fragment A3 were also ligated by overlap extension PCR (reaction system and conditions are shown in the tables below). The sequences of the products were verified by sequencing. The ligated fragments were further inserted into the pBs-Neo-B plasmid (HindIII/SwaI/XhoI) to obtain the pBs-Neo-(A1+A2-1+A2-2+A3+B) plasmid.

(3). pBs-Neo-(A1+A2-1+A2-2+A3+B) plasmids were introduced into human BAC clones by electroporation. pBs-Neo-(AB) plasmids, which contains AB fragment, were obtained by homologous recombination. The AB fragment was shown in FIG. 2, and has human DNA fragment SEQ ID NO: 3.

(4). pBs-Neo-(AB) plasmids were introduced into mouse BAC clones by electroporation. Mouse BAC clones with AB fragments were obtained by homologous recombination.

(5). pDTA-down-C plasmids were obtained by ligating fragments C1 and C2 to pDTA-down plasmids (AIO kits). The sequences of the plasmids were further verified by sequencing.

(6). pDTA-down-C plasmids were introduced into mouse BAC clones containing AB fragments. pDTA-down-hCD3-part plasmids containing 5'-homologous arm, AB fragments, and 3'-homologous arm were obtained by homologous recombination (FIG. 2).

TABLE 6

The PCR reaction system (20 µL)

| Composition | Amount |
| --- | --- |
| 5 × Phusion HF Buffer | 4 µL |
| dNTP (10 mM) | 0.4 µL |
| Primer F (10 µM) | 1 µL |
| Primer R (10 µM) | 1 µL |
| DNA template | 5 ng |
| Phusion DNA polymerase(2 U/µL) | 0.2 µL |
| $H_2O$ | Add to 20 µL |

TABLE 7

The PCR reaction conditions
PCR Conditions

| Temperature | Time | Cycles |
| --- | --- | --- |
| 98° C. | 30 sec | 1 |
| 98° C. | 10 sec | 35 |
| 58° C. | 25 sec | |
| 72° C. | 30 sec/kb | |
| 72° C. | 5-10 min | 1 |
| 4° C. | 10 min | 1 |

In step (2), when fragments A1 and A2-1 were ligated, Primer F in Table 6 was SEQ ID NO: 11, Primer R was SEQ ID NO: 14, and template DNA was the recovered PCR amplification product of A1 fragment and A2-1 fragment. When fragments A2-2 and A3 were ligated, Primer F was SEQ ID NO: 15, primer R was SEQ ID NO: 18, and template DNA was the recovered PCR amplification product of A2-2 fragment and A3 fragment. The electroporation process is described in detail below.

Electroporation

The BAC clones were added into LB liquid medium (5 mL) with appropriate antibiotics as shown in the table below. The bacteria were cultured at 30° C. for 12-16 hours at 250 rpm. The next day, the corresponding antibiotics (1:50) as shown in the table below were added into the LB liquid medium, and the bacteria were further cultured at 30° C., 250 rpm for 2-3 hours. When the OD value reached 0.15~0.2, 30 mL of culture medium was collected. 1.2 mL of arabinose (0.4%) was added. After 45-60 min of induction, the culture was kept on ice for 30 min. The culture was then aliquoted into 50 mL centrifuge tubes, centrifuged at 5000 rpm for 10 min at −1° C. The supernatant was discarded. ddH$_2$O (10 mL) was then added, and the solution was then centrifuged at 5000 rpm for 10 min at −1° C. The supernatant was discarded. After being washed for one more time, the bacteria were kept on ice.

15 µL of plasmids (0.2-0.3 ng/µL) was added into a 1.5 mL Eppendorf tube, and kept on ice. 85 µL of competent cells were then added, and were carefully mixed with the plasmids. The mixture was then transferred to cuvettes. The setting for the electroporator (BTX, ECM-630) was 1.3 kV, 50 g, and 125n. Immediately after electroporation, 800 µL of LB liquid medium was added. After culturing the bacteria at 150 rpm for 1 h at 30° C., the bacteria were plated on petri dishes with appropriate antibiotics as shown in the table below, and were then cultured for at least 30 hours.

TABLE 8

| Steps | Antibiotics for LB medium | Antibiotics for petri dishes |
| --- | --- | --- |
| Step (3) (Human BAC) | Chloramphenicol (Chl) | Carbenicillin (CBC) + Kanamycin (Kan) |
| Step (4) (Mouse BAC) | Chl | Chl + Kan |
| Step (6) (BAC containing AB fragments) | Chl + Kan | CBC + Kan | pBs-Neo Plasmids

Figure 4:
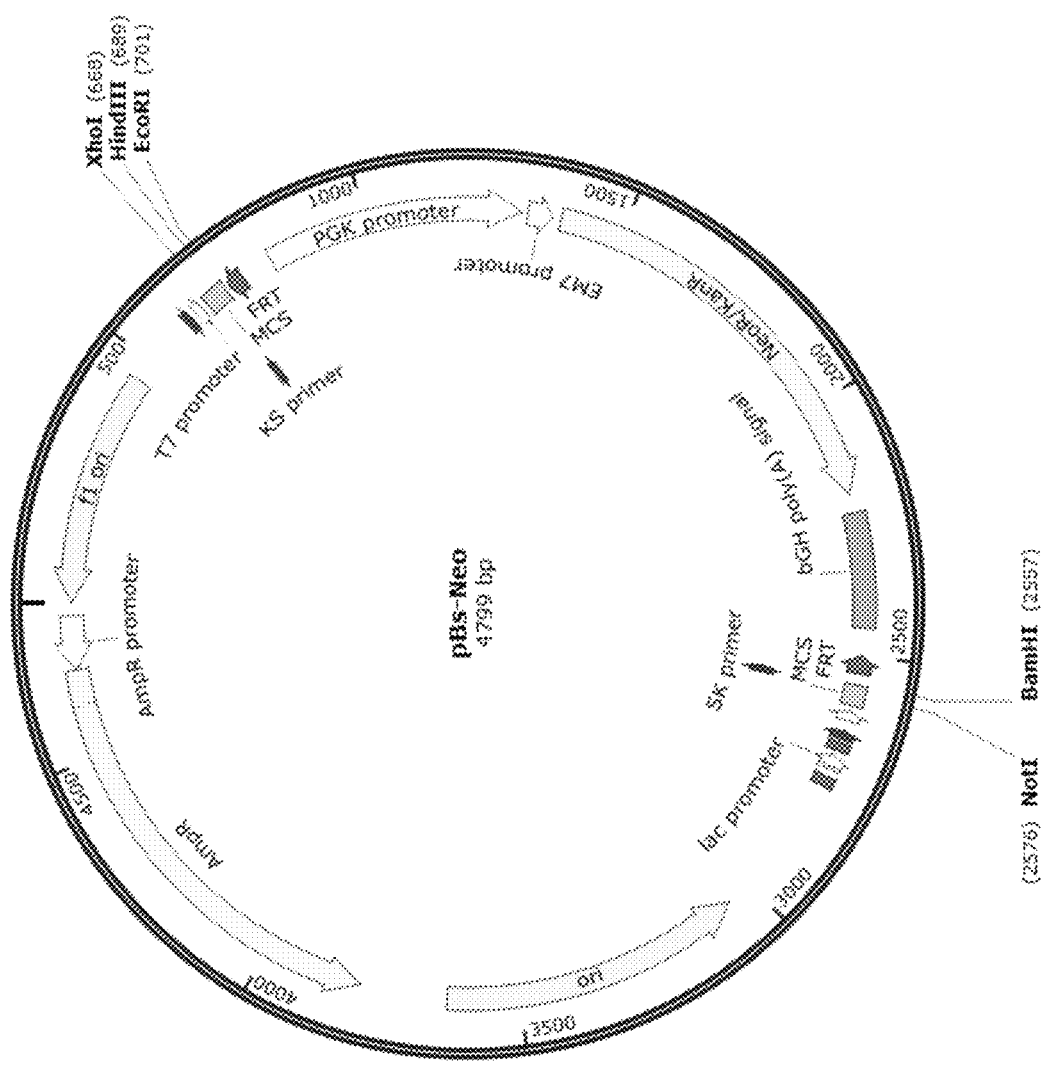
FIG. 4 is a schematic diagram showing the structure of pBs-Neo plasmid.

FIG. 4 shows pBs-Neo vector map. The plasmid backbone was obtained from Agilent (Cat. No. 212205). DNA fragment containing frt and neo gene (neomycin-resistance) (SEQ ID NO: 25) was synthesized and ligated to the vector backbone by restriction enzyme digestion (EcoRI/BamHI). The sequences of the plasmids were further verified by sequencing.

Example 4. Verification of pDTA-Down-hCD3-Part Vector

Figure 5A:
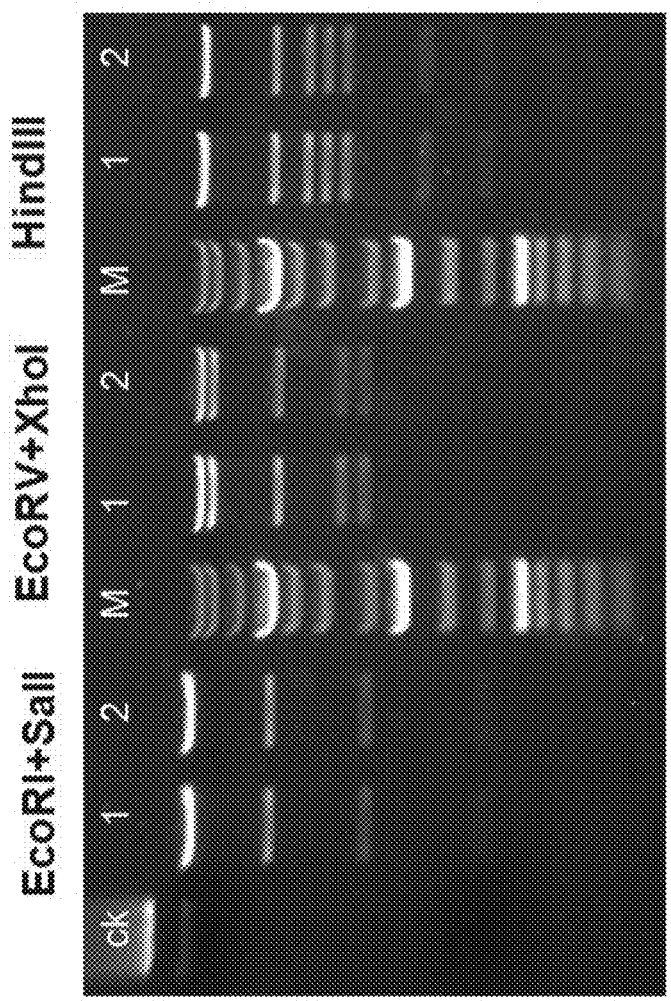
FIG. 5A shows the restriction enzymes digestion results of the targeting plasmid pDTA-down-hCD3-part by three sets of restriction enzymes. Among them, M indicates molecular-weight size markers; ck indicates undigested plasmids.
Figure 5B:
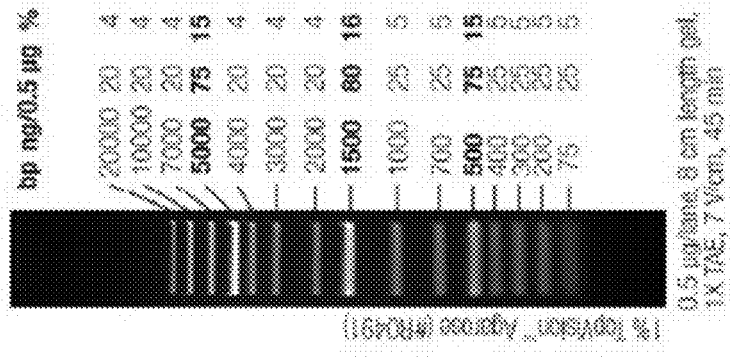
FIG. 5B shows molecular-weight size markers.
Figure 6A:
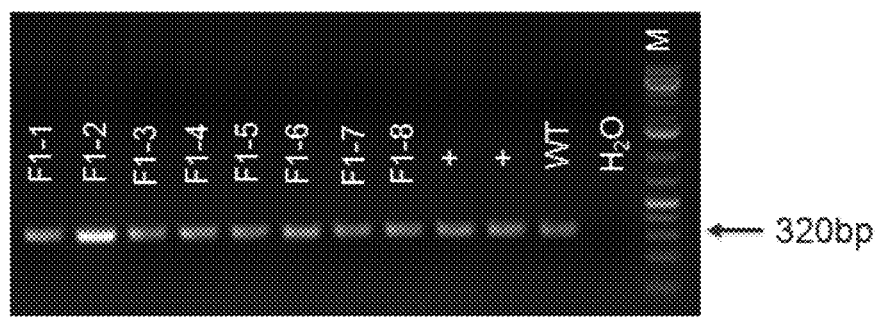
FIGS. 6A-6D show PCR identification results of samples collected from tails of F1 generation mice (hCD3-part version). WT is wildtype; + is positive control.
Figure 6B:
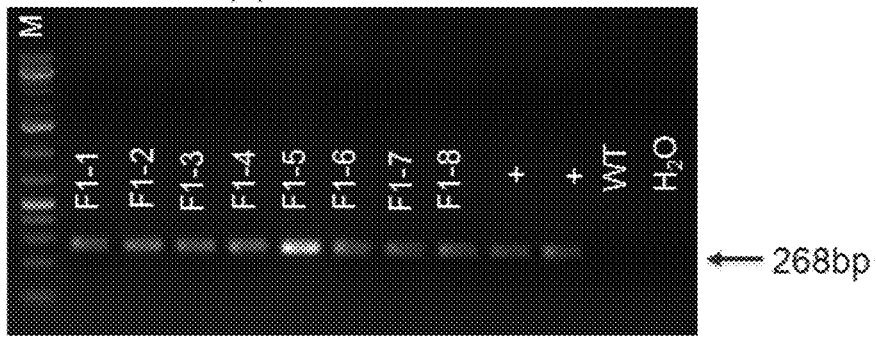
Figure 6C:
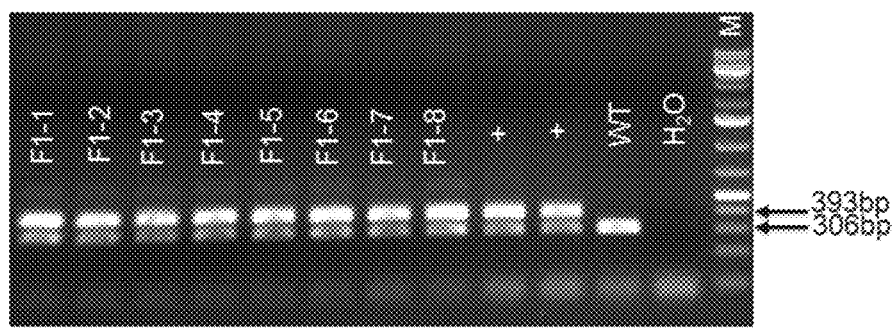
Figure 6D:
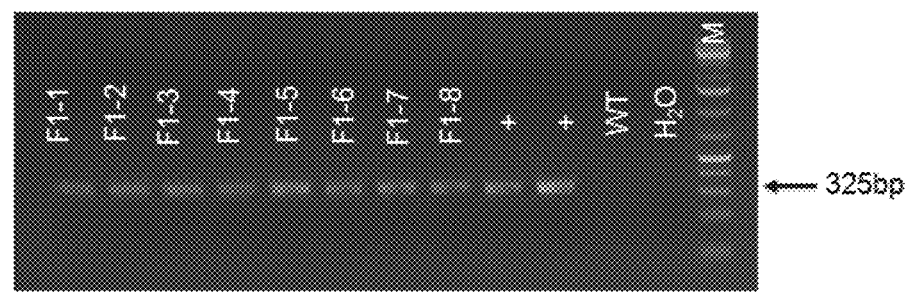

Two pDTA-down-hCD3-part clones were randomly selected and tested by three sets of restriction enzymes. Among them, EcoRI+SalI should generate 693 bp+1863 bp+4538 bp+20530 bp fragments; EcoRV+XhoI should generate 1890 bp+2318 bp+4152 bp+8358 bp+10906 bp fragments; HindIII should generate 15 bp+687 bp+1178 bp+2342 bp+2816 bp+3310 bp+4586 bp+12690 bp fragments. The results for Plasmids 1 and 2 were in line with the expectations (FIGS. 5A-5B). The sequences of Plasmids 1 and 2 were further confirmed by sequencing.

Example 5. C57BL/6 Mouse Embryonic Stem Cell Culture, Transfection and Clone Screening Embryonic Stem Cell Culture C57BL/6 embryonic stem cells were cultured in petri dishes with feeder cells, and were incubated in an incubator at 37° C., 5% $CO_2$ with saturated humidity. The composition of the culture medium is shown in the table below.

TABLE 9

| Medium composition | Volume |
| --- | --- |
| Knockout DMEM | 500 ml |
| FBS (Fetal bovine serum) | 90 ml |
| MEM NEAA (MEM Non-Essential Amino Acids Solution) | 6 ml |
| L-Glutamine | 6 ml |
| ESGRO LiF (Leukemia Inhibitory Factor) | 60 µL |
| β-Mercaptoethanol | 600 µL |

Transfection by Electroporation

C57BL/6 embryonic stem cells were confirmed to be in good condition prior to electroporation.

The petri dishes with embryonic stem cells were retrieved from the incubator. The medium was removed. 5 ml phosphate buffered solution (PBS) was added, and the petri dishes were washed twice. 1.5 ml 0.25% trypsin was added to each petri dish, and was incubated in 37° C. incubator for 3 minutes. 3.5 ml of ES medium per dish was then added to stop the digestion. The cells were then transferred to 50 ml centrifuge tubes to count cells. 1.2×10⁷ cells were added into a new 50 ml centrifuge tube. The cells were centrifuged at 1200 rpm for 5 min at 4° C. The supernatant was then removed. An appropriate amount of RPMI medium (without phenol red) was added. The cells were then suspended and transfected with pDTA-down-hCD3-part vector. The mixture was kept in ice water bath for 5 minutes, and was then transferred to cuvettes. The setting for electroporation was 280V, 500 g, and 10 ms. The cuvettes were kept in ice water bath for 5 min, and then kept at room temperature for 5 minutes. The cells were then transferred into a 50 ml centrifuge tube containing 40 ml of embryonic stem cell culture medium. The mixture was then divided, and added into four 100 mm petri dishes containing MMC feeder cells. These cells were then incubated at 37° C. in a 5% $CO_2$ incubator. After incubating these cells for 20 hours, the medium was replaced by G418 medium.

Clone Selection

After 20 hours of culturing, the medium was replaced by G418 medium for positive selection and negative selection. The cell colonies were then picked and transferred into 96-well plates. After the cells grew for a sufficient period of time, the cells were then transferred to 48-well, 6-well plates and 60-mm petri dishes, and the DNA of the cells was collected. PCR and Southern blotting were used to select the positive clones.

Example 6. Microinjection and Embryo Transfer

The positive embryonic stem cells in Example 5 were injected into BALB/c mouse blastocysts. The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected blastocysts were then transferred to a culture medium and were cultured for a short time period, and then was transplanted into the oviduct of the recipient mouse to produce the chimeric mice (F0 generation). The chimeric mouse was then mated with Flp recombinase transgenic mice (FIG. 3), generating F1 generation (black or gray color). Black mice were selected. Genomic DNA from the tails of black mice were collected and tested by PCR to determine whether the mouse is a humanized CD3e gene heterozygote. The primers for PCR are shown in the table below.

TABLE 10

| Primer | Sequence | Product length |
| --- | --- | --- |
| WT-F | 5'-ATGGCAACCAATGATCCAGGGT-3' (SEQ ID NO: 26) | WT: 320 bp |
| WT-R | 5'-CTGAGTCCCCAGCCCTTGTC-3' (SEQ ID NO: 27) | |
| WT-F | 5'-ATGGCAACCAATGATCCAGGGT-3' (SEQ ID NO: 26) | Mut: 268 bp |
| Mut-R | 5'-ATGAGGCTCCTTGGTGCCACT-3' (SEQ ID NO: 28) | |

TABLE 10-continued

| Primer | Sequence | Product length |
| --- | --- | --- |
| Frt-F | 5'-CATGTATCGCAACATCAAAGGTGCAG-3' (SEQ ID NO: 29) | Mut: 393 bp |
| Frt-R | 5'-CATCCTGCTGTATAACCACTACTGC-3' (SEQ ID NO: 30) | WT: 306 bp |
| Flp-F2 | 5'-GACAAGCGTTAGTAGGCACATATAC-3' (SEQ ID NO: 31) | Mut: 325 bp |
| Flp-R2 | 5'-GCTCCAATTTCCCACAACATTAGT-3' (SEQ ID NO: 32) | |

TABLE 11

| The PCR reaction system (20 μL) | |
| --- | --- |
| Composition | Amount |
| 2 × PCR Buffer | 10 μL |
| dNTP (2 μM) | 4 μL |
| Upstream primer (10 μM) | 0.6 μL |
| Downstream primer (10 μM) | 0.6 μL |
| DNA template | 100 ng |
| KOD-FX (1 U/μL) | 0.4 μL |
| $H_2O$ | Add to 20 μL |

The PCR conditions were
94° C. 2 min;
98° C. 10 sec, 62° C. 30 sec, 68° C. 30 sec, 30 cycles in total;
68° C. 10 min;
16° C. 10 min.

PCR was performed to determine whether the recombinant fragment was inserted at the correct genomic site. The primer pair WT-F and WT-R was used to amplify exon 2 of CD3e gene of wild-type mice. The primer pair WT-F and Mut-R was used to amplify the humanized exon 2 fragment.

The primer pair Frt-F and Frt-R was used to amplify neo fragments to determine whether the neo gene was removed. The primer pair Flp-F2 and Flp-R2 was used to confirm the presence of Flp fragments.

The PCR results were shown in FIGS. 6A-6D. All tested mice (F1-1, F1-2, F1-3, F1-4, F1-5, F1-6, F1-7, F1-8) were heterozygous humanized mice.

Example 7: Humanized CD3e Mice (Full Sequence Replacement)

Figure 8:
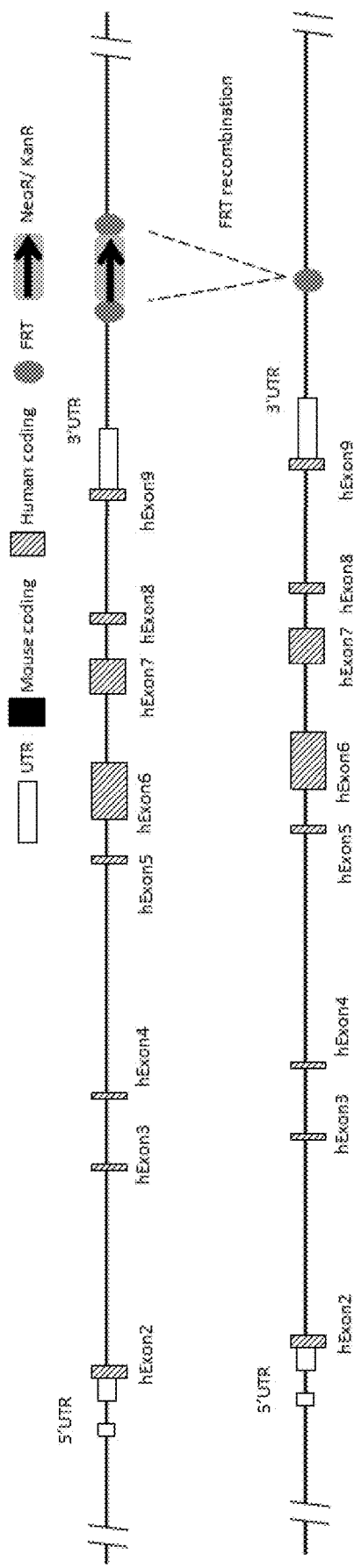
FIG. 8 shows a map of humanized CD3e gene in mouse and the FRT recombination process, wherein the entire mouse CD3e coding sequence is replaced by human CD3e sequence.

In this example, mouse exons 2-8 were replaced by the corresponding human CD3e gene sequence (exons 2-9). The humanized mice can express the full length of human CD3e (SEQ ID NO: 7). The targeting strategy of the full coding sequence replacement of the CD3e gene is shown in FIG. 7. The targeting vector comprises a 5' homology arm (SEQ ID NO: 37), a 3' homology arm (SEQ ID NO: 38) and a human DNA fragment (SEQ ID NO: 39). The schematic presentation of the humanized CD3e gene and FRT recombination is shown in FIG. 8. The mRNA sequence of the humanized mouse CD3e gene is shown in SEQ ID NO: 40.

Similar to Examples 2-4, primers for amplifying 7 homologous recombination fragments (A1, A2-1', A2-2', A3', B, C1, C2) were designed and the primer sequences are shown in the table below. The fragments were amplified, and pDTA-down-hCD3-full vectors were constructed.

Figure 9A:
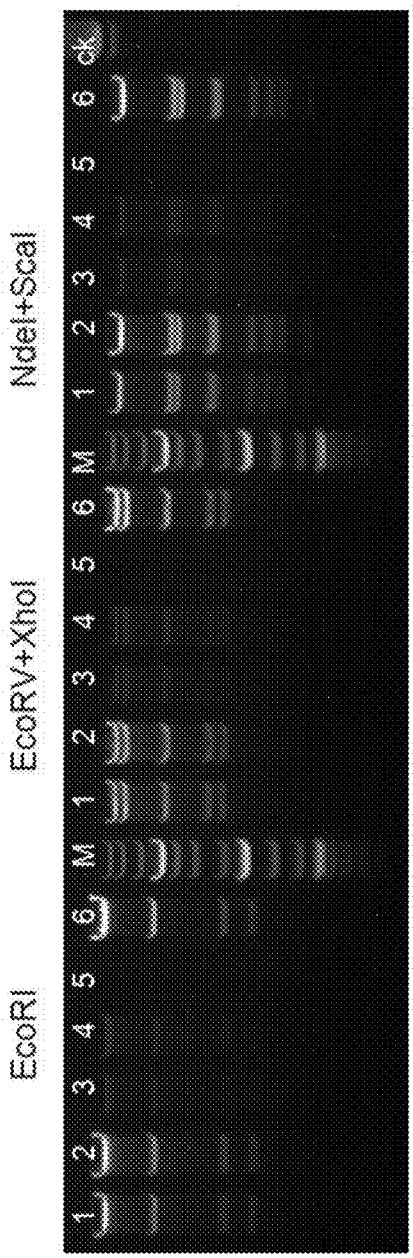
FIG. 9A shows the restriction enzymes digestion results of the targeting plasmid pDTA-down-hCD3-full by three sets of restriction enzymes. Among them, M indicates molecular-weight size markers; ck indicates undigested plasmids.
Figure 9B:
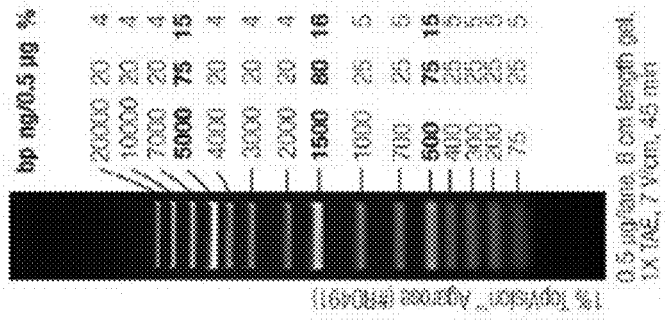
FIG. 9B shows molecular-weight size markers.
Figures 10A, 10B, 10C, 10D:
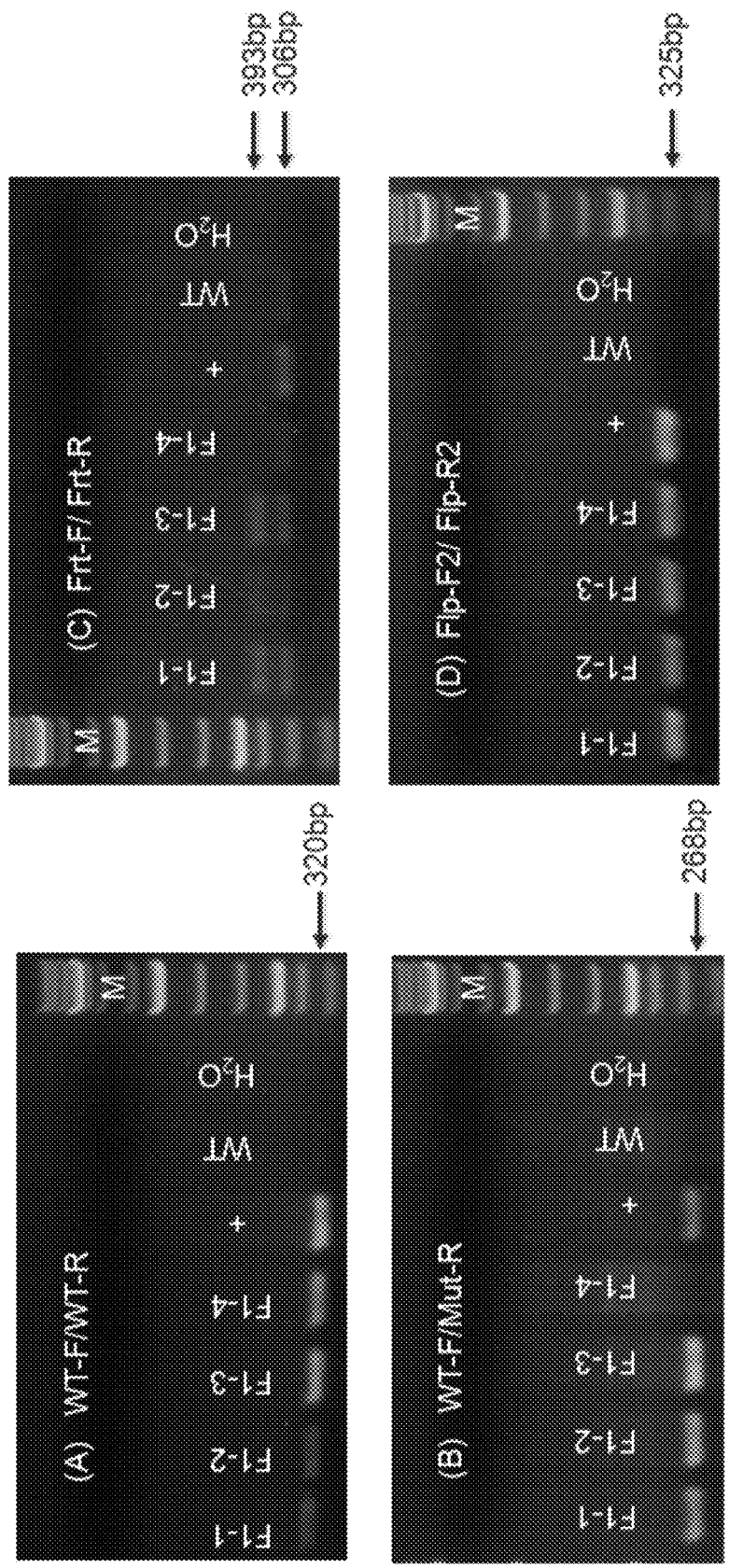
FIGS. 10A-10D show PCR identification results of samples collected from tails of F1 generation mice (hCD3-full version). WT is wildtype; + is positive control.

Six pDTA-down-hCD3-full clones were randomly selected and tested by three sets of restriction enzymes. Among them, EcoRI should generate 19461 bp+5231 bp+1863 bp+1289 bp fragments; EcoRV+XhoI should generate 10904 bp+8568 bp+4372 bp+2320 bp+1890 bp fragments; NdeI+ScaI should generate 10790 bp+4459 bp+3899 bp+2366 bp+2217 bp+1349 bp+1090 bp+902 bp+622 bp+150 bp fragments. The results for Plasmids 1, 2, 3, 4, and 6 were in line with the expectations (FIGS. 9A-9B). The sequences of Plasmids 2 and 6 were further confirmed by sequencing and used in the subsequent experiments.

C57BL/6 mouse embryonic stem cell culture, transfection and clone screening were performed based on the methods as described in Examples 5-6. PCR was performed to determine whether the recombinant fragment was inserted at the correct genomic site. The results were shown in FIGS. 10A-10D. Among the tested mice, F1-1, F1-2, and F1-3 were humanized CD3e heterozygous mice.

TABLE 12

| Fragments | Length (bp) | Primer sequence (5'-3') |
| --- | --- | --- |
| A1 | 514 bp | F: cgatctcgagagtactgagtgcttcaacgtcttc (SEQ ID NO: 11)<br>R: gtgcccgactgcatcctctcagaatgctctctacc (SEQ ID NO: 12) |
| A2-1' | 508 bp | F: gcattctgagaggatgcagtcgggcactcactg (SEQ ID NO: 13)<br>R: gtttggggctatttaaattacgaggcgttttatggtctc (SEQ ID NO: 33) |
| A2-2' | 656 bp | F: cgcctcgtaatttaaatagcccaaactttgctcac (SEQ ID NO: 34)<br>R: ctctcctatctgtcagatgcgtctctgattcaggc (SEQ ID NO: 35) |
| A3' | 1109 bp | F: cgcatctgacagataggagagacatcgccttc (SEQ ID NO: 36)<br>R: cgataagcttcctggcagctgatggaaaccag (SEQ ID NO: 18) |
| B | 536 bp | F: cgatggatccagaattcaagtgctgctgaacagagccag (SEQ ID NO: 19)<br>R: cgatgcggccgcagtactcattttaacataagcatcgatgcc (SEQ ID NO: 20) |
| C1 | 525 bp | F: gctggtaccggcgcgcctcgagctcagatgttcctgcaatcatg (SEQ ID NO: 21)<br>R: gctgaatgctgatatcatgtgaggcctttaaatgtg (SEQ ID NO: 22) |
| C2 | 525 bp | F: aggcctcacatgatatcagcattcagcaagtccag (SEQ ID NO: 23)<br>R: tcctcttcagacctggcggccgcacaagaaatgtttcagatgcctttc (SEQ ID NO: 24) |

Example 8. Verification of Genetically Modified Humanized Mouse Model

Verification of Humanized Heterozygous F1 Generation Mouse (hCD3-Part Version)

A humanized heterozygous F1 generation mouse (hCD3-part version; partial sequence replacement) was selected (4-6 weeks). Three wildtype C57BL/6 mice were used as the control. These mice were treated with anti-CD3 antibodies as show in the table below.

TABLE 13

| Mouse | Treatment |
| --- | --- |
| C57BL/6 | PBS (control) |
| C57BL/6 | 7.5 µg of anti-mCD3 antibody 145-2C11 (i.p.) |

TABLE 13-continued

| Mouse | Treatment |
| --- | --- |
| C57BL/6 | 7.5 µg of anti-hCD3 antibody OKT-3 (i.p.) |
| Humanized CD3e heterozygous mouse | 7.5 µg of anti-hCD3 antibody OKT-3 (i.p.) |

The spleens were collected 24 hours after the injection, and the spleen samples were grinded. The samples were then passed through 70 µm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and were separated to two groups for further experiments.

Figures 11A, 11B, 11C, 11D:
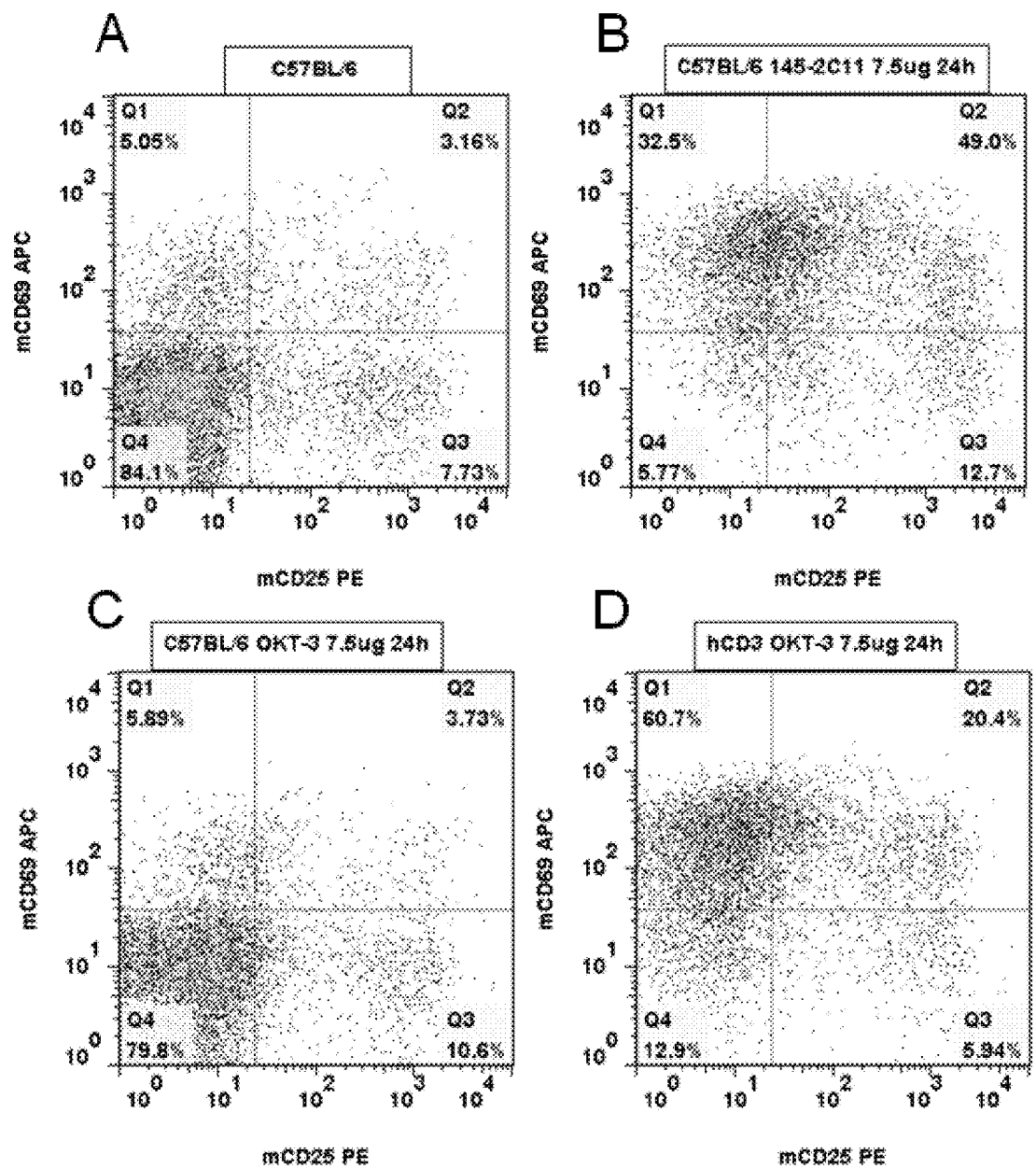
FIGS. 11A-11D are flow cytometry results for wildtype mice and heterozygous humanized CD3e mice.

In the first group, extracellular proteins were stained with APC anti-mouse CD69 antibody (mCD69 APC) and PE anti-mouse CD25 antibody (mCD25 PE), and cells were washed once with PBS before flow cytometry analysis. The results of the flow cytometry analysis (FIGS. 11A-11D) showed that T cells of C57BL/6 mice were activated with anti-mCD3 antibody 145-2C11 (FIG. 11B) and did not respond to anti-hCD3 antibody OKT-3 (FIG. 11C). OKT-3, however, can activate T cells of the humanized CD3e heterozygous mouse (FIG. 11D), indicating that anti-hCD3 antibody can bind to and activate T cells in the humanized mouse.

Figures 12A, 12B, 12C, 12D, 12E, 12F, 12G, 12H:
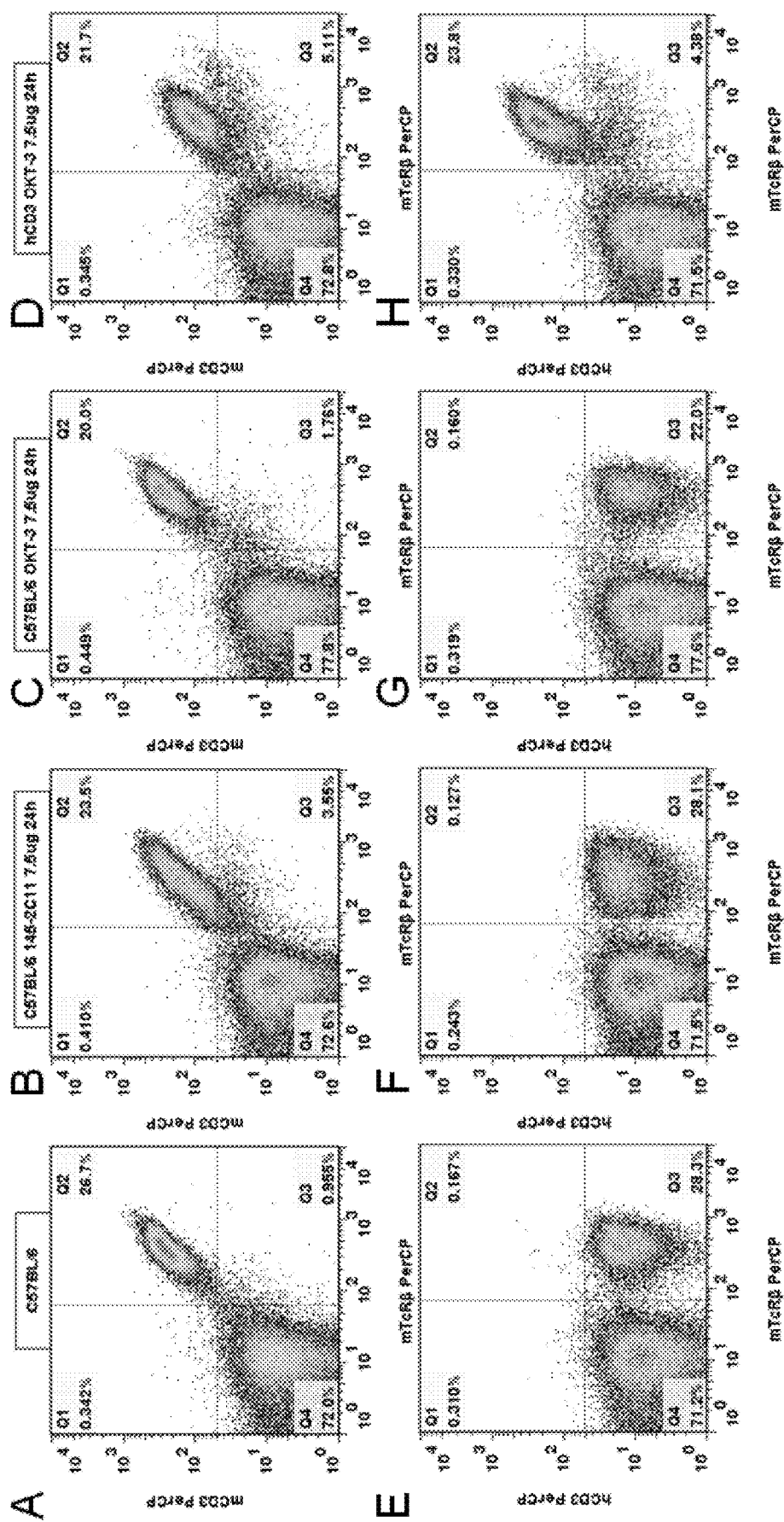
FIGS. 12A-12H are flow cytometry results for wildtype mice and heterozygous humanized CD3e mice.

In the second group, extracellular proteins were stained with (1) mTcRβ PerCP and PerCP anti-mCD3e antibody (mCD3 PerCP) or (2) mTcRβ PerCP and PerCP anti-hCD3 antibody (hCD3 PerCP). Cells were washed once with PBS before flow cytometry analysis. The results of the flow cytometry analysis (FIGS. 12A-12D) showed that mCD3 can be detected in the wildtype C57BL/6 mice and the humanized mice. However, humanized CD3 was only detected in the humanized mouse (FIG. 12H)

Verification of Humanized Heterozygous F1 Generation Mouse (hCD3-Full Version)

A humanized heterozygous F1 generation mouse (hCD3-full version; full coding sequence replacement) was selected (7 weeks). Two wildtype C57BL/6 mice were used as the control. One wildtype C57BL/6 mouse and the humanized mice were injected with anti-hCD3 antibody OKT-3, and one wildtype C57BL/6 mouse was injected with PBS.

The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and were separated to two groups for further experiments.

Figures 13A, 13B, 13C:
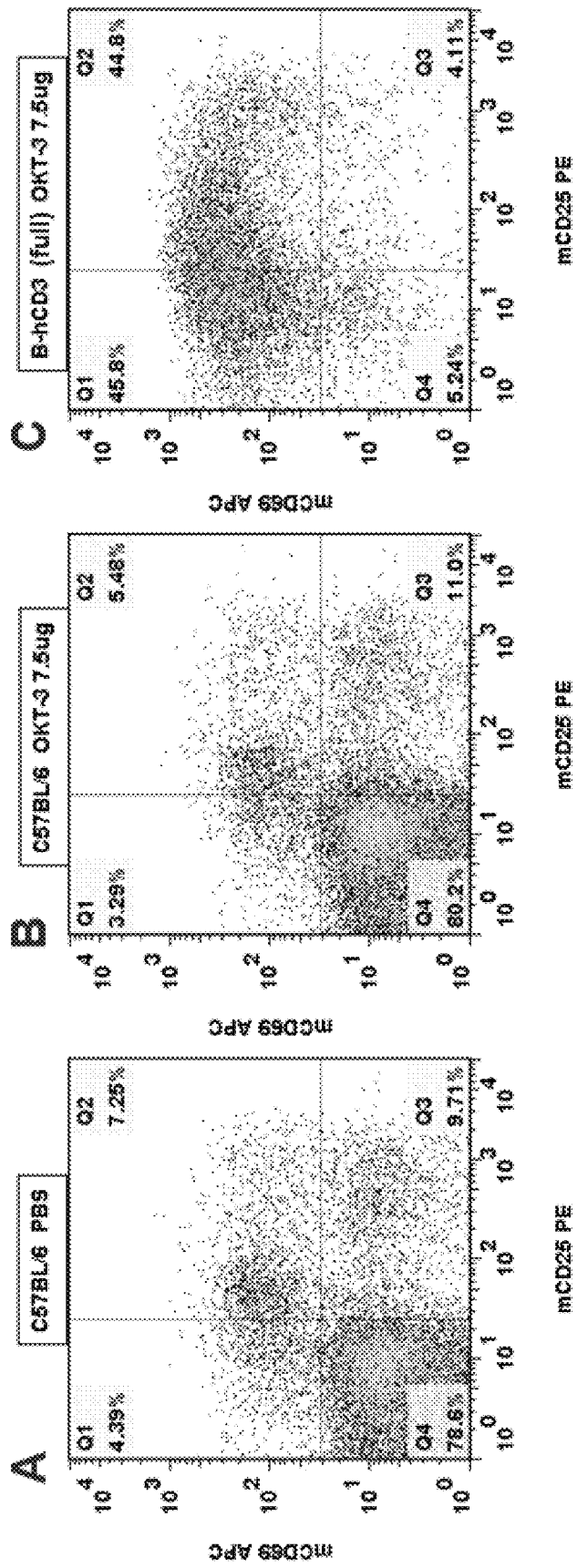
FIGS. 13A-13C are flow cytometry results for wildtype mice and heterozygous humanized CD3e mice.

In the first group, extracellular proteins were stained with mCD69 APC and mCD25 PE. Cells were washed once with PBS before flow cytometry analysis. The results of the flow cytometry analysis (FIGS. 13A-13C) showed that OKT-3 can activate T cells of the humanized CD3e heterozygous mouse, but is not effective in activating T cells of the wildtype mouse.

Figures 14A, 14B, 14C, 14D, 14E, 14F:
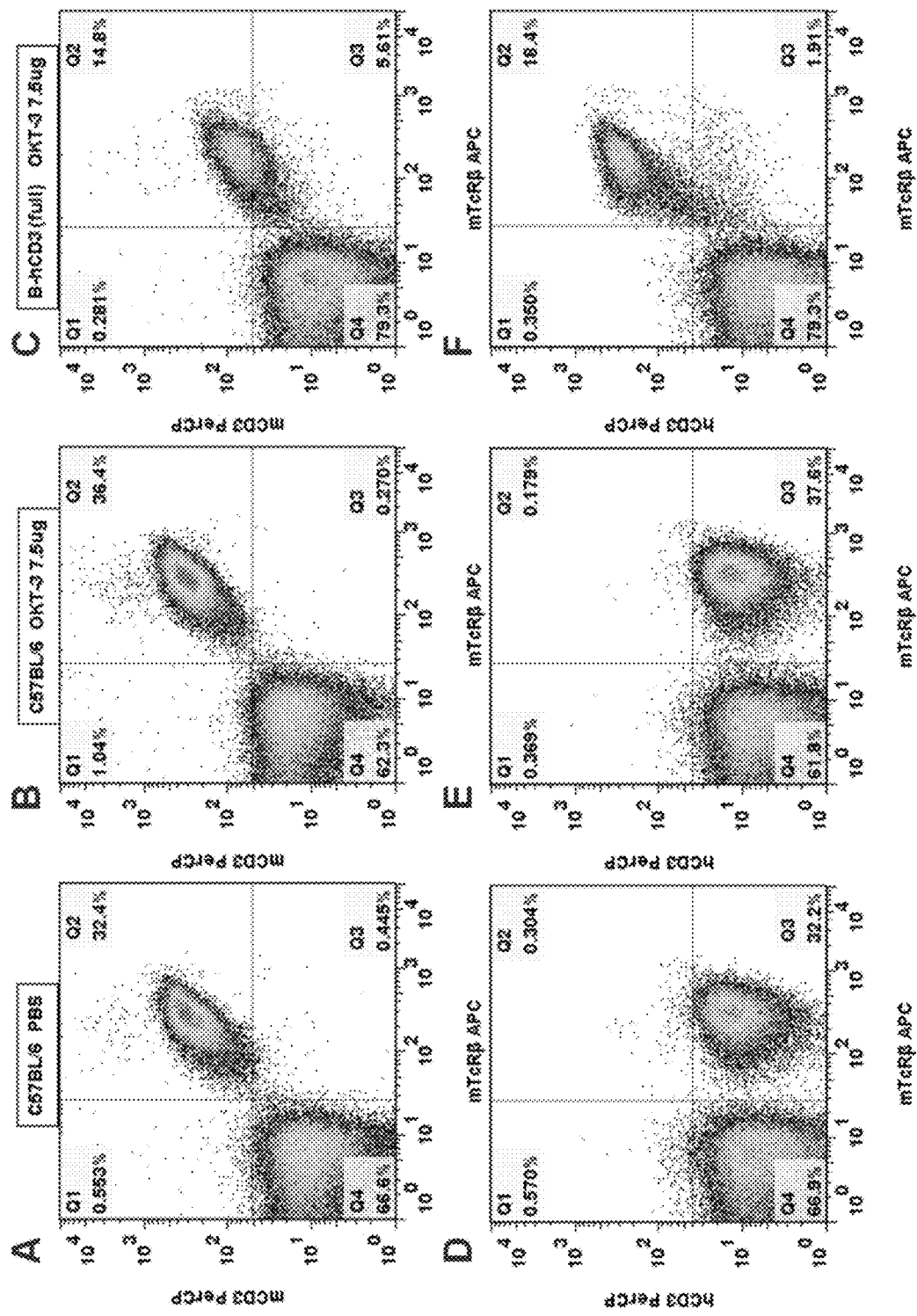
FIGS. 14A-14F are flow cytometry results for wildtype mice and heterozygous humanized CD3e mice.
Figures 15A, 15B, 15C, 15D, 15E, 15F:
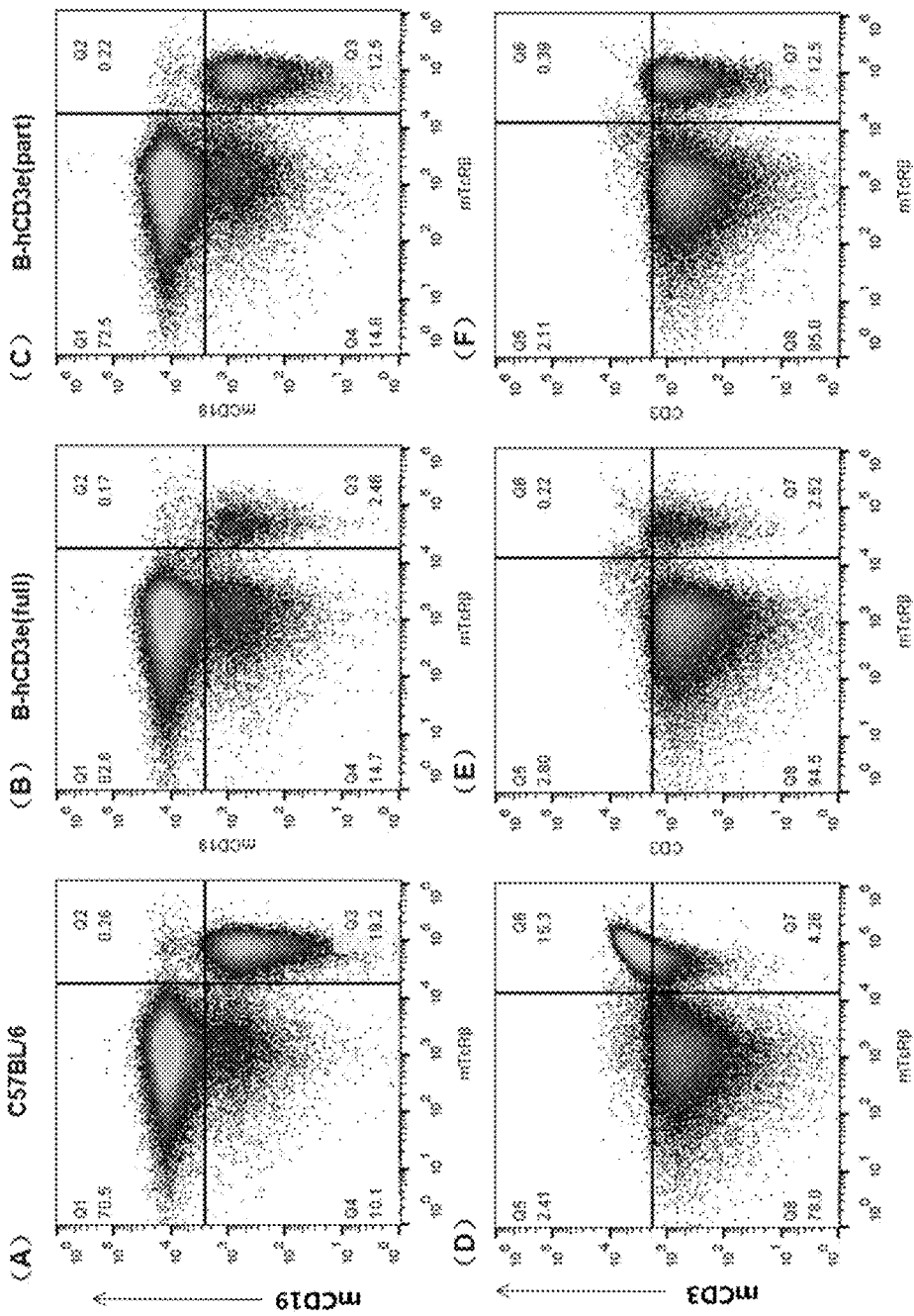
FIGS. 15A-15F are flow cytometry results for spleen cells.
Figures 16A, 16B, 16C, 16D, 16E, 16F:
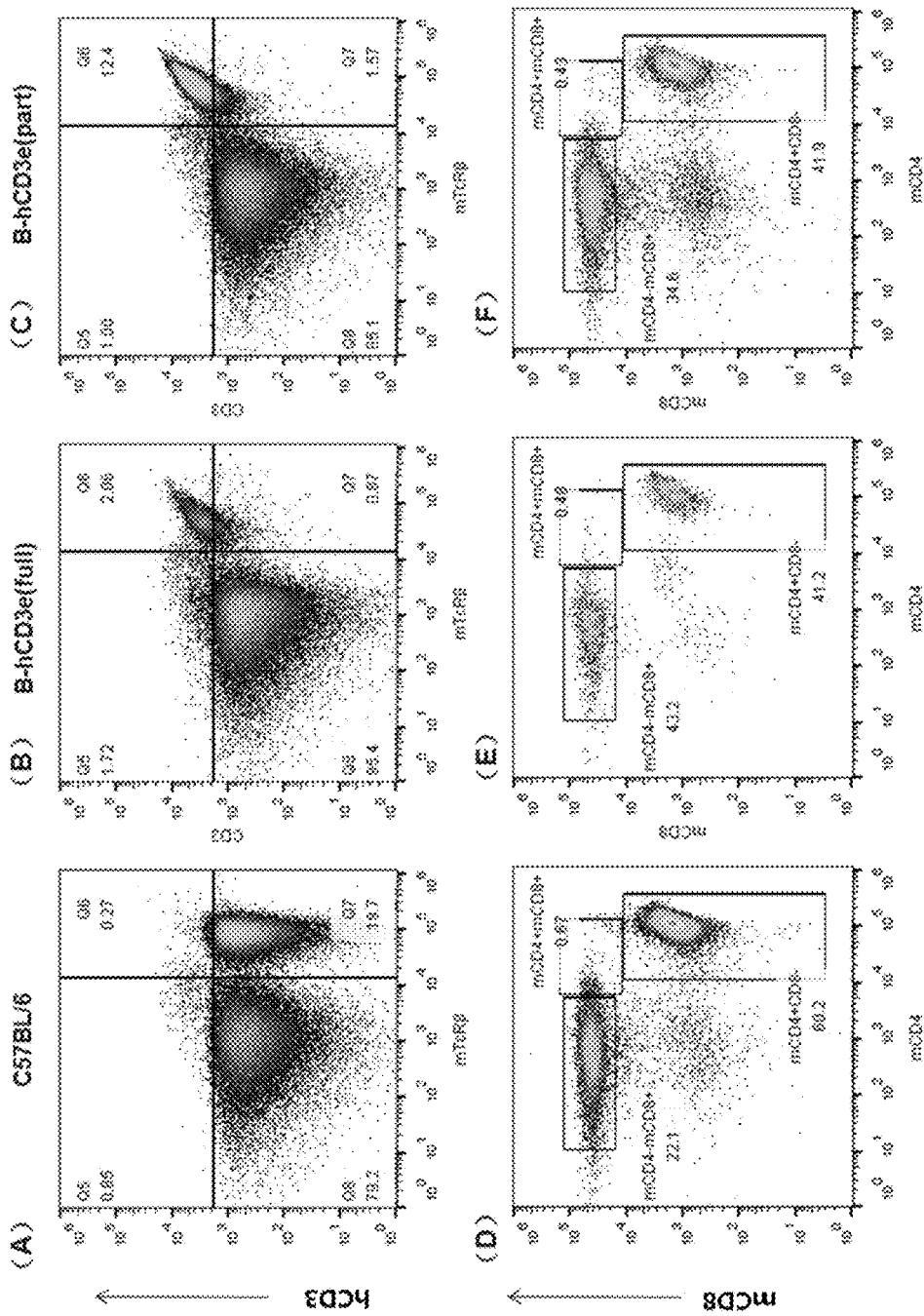
FIGS. 16A-16F are flow cytometry results for spleen cells.
Figures 17A, 17B, 17C, 17D, 17E, 17F:
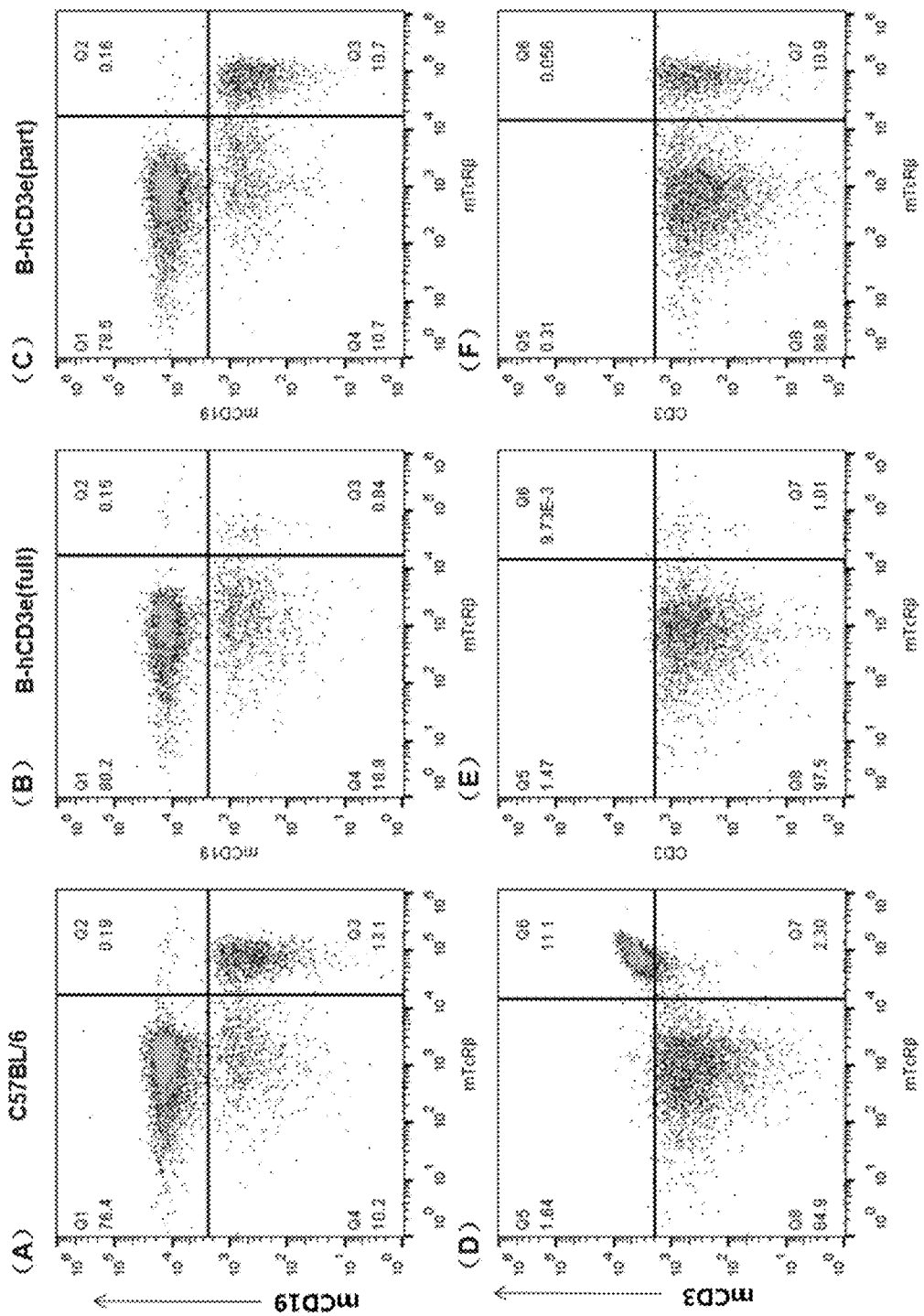
FIGS. 17A-17F are cell flow cytometry results for peripheral blood.
Figures 18A, 18B, 18C, 18D, 18E, 18F:
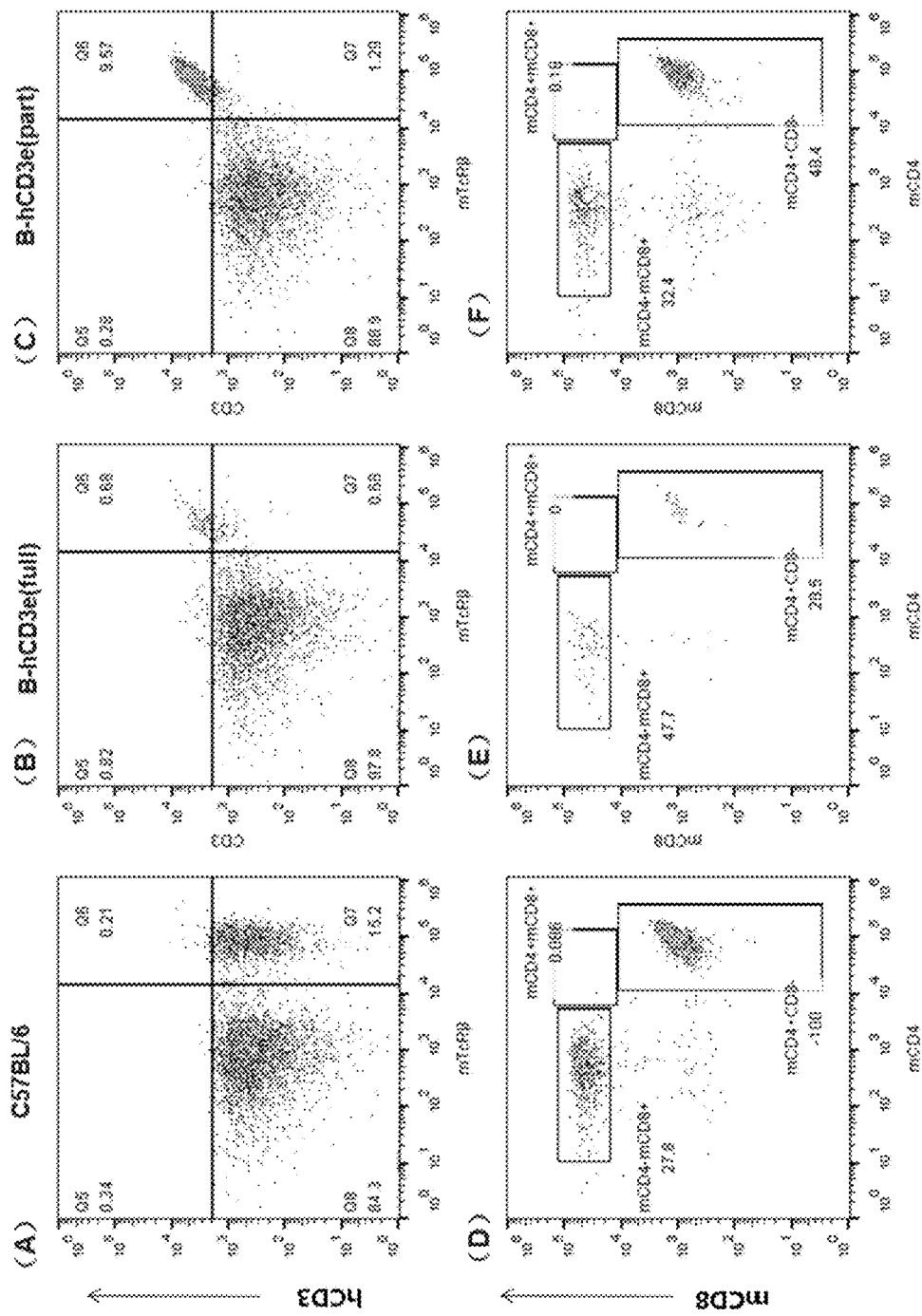
FIGS. 18A-18F are cell flow cytometry results for peripheral blood.
Figures 19A, 19B, 19C, 19D, 19E, 19F:
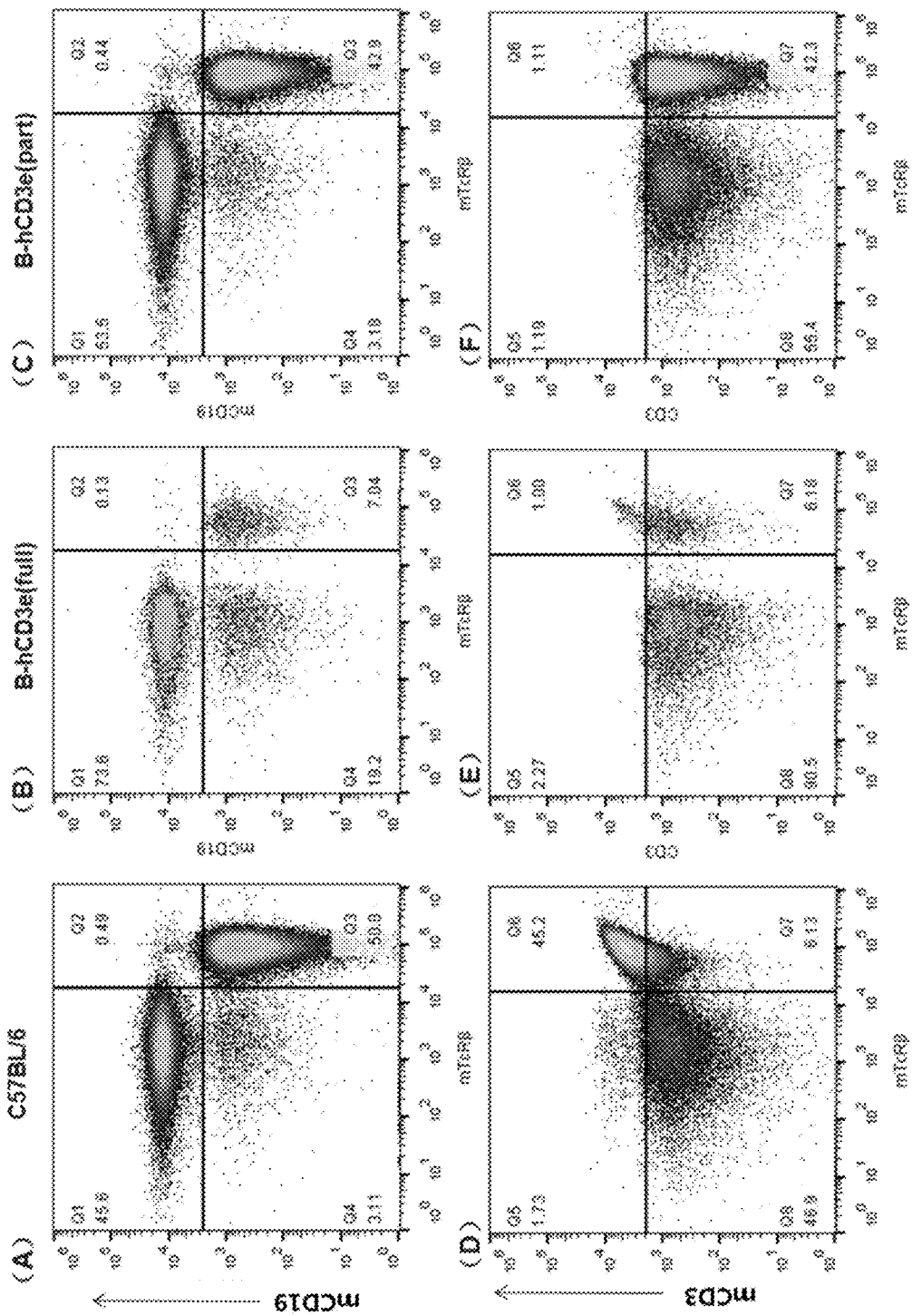
FIGS. 19A-19F are cell flow cytometry results for inguinal lymph nodes.
Figures 20A, 20B, 20C, 20D, 20E, 20F:
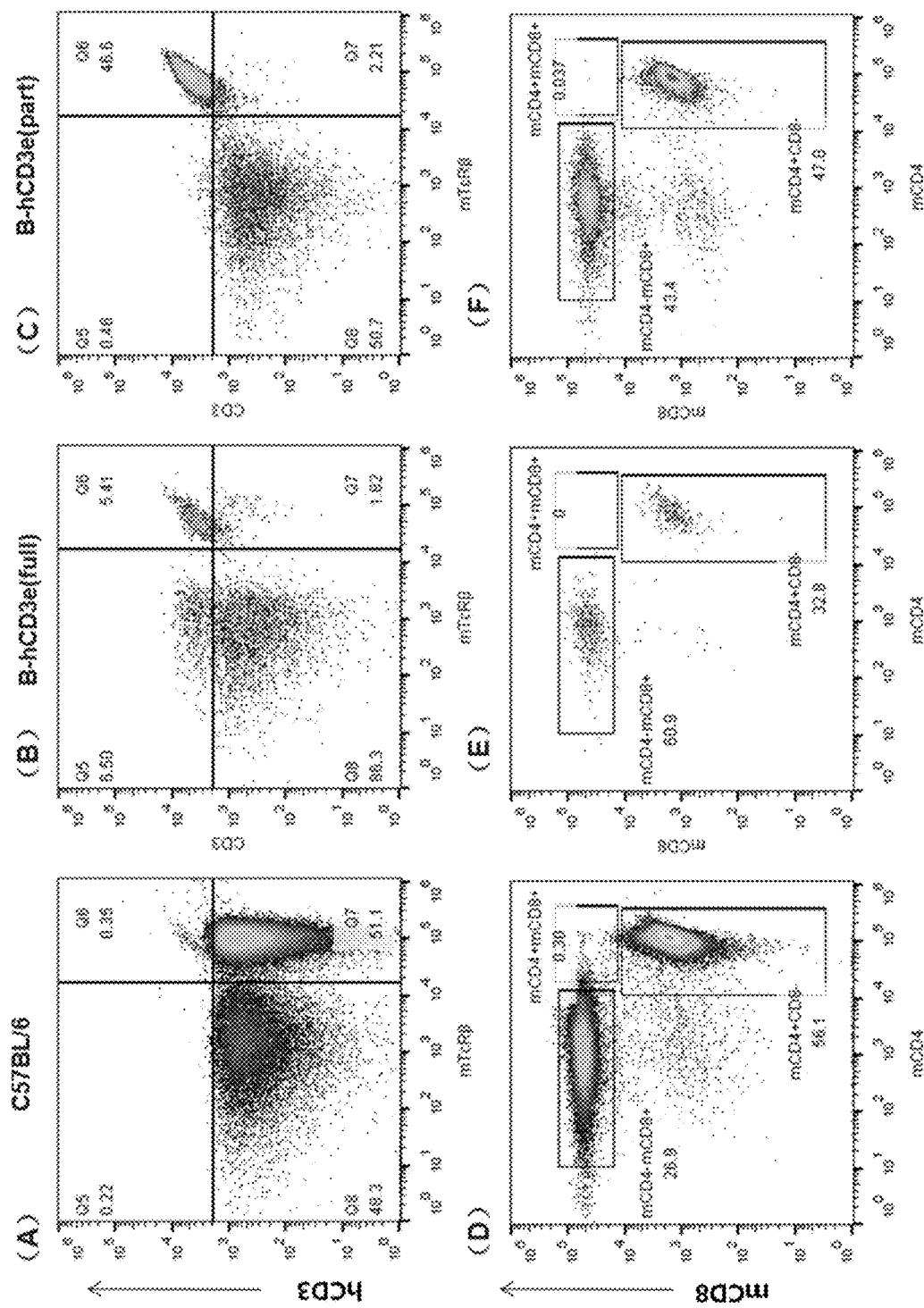
FIGS. 20A-20F are cell flow cytometry results for inguinal lymph nodes.
Figures 21A, 21B, 21C, 21D, 21E, 21F:
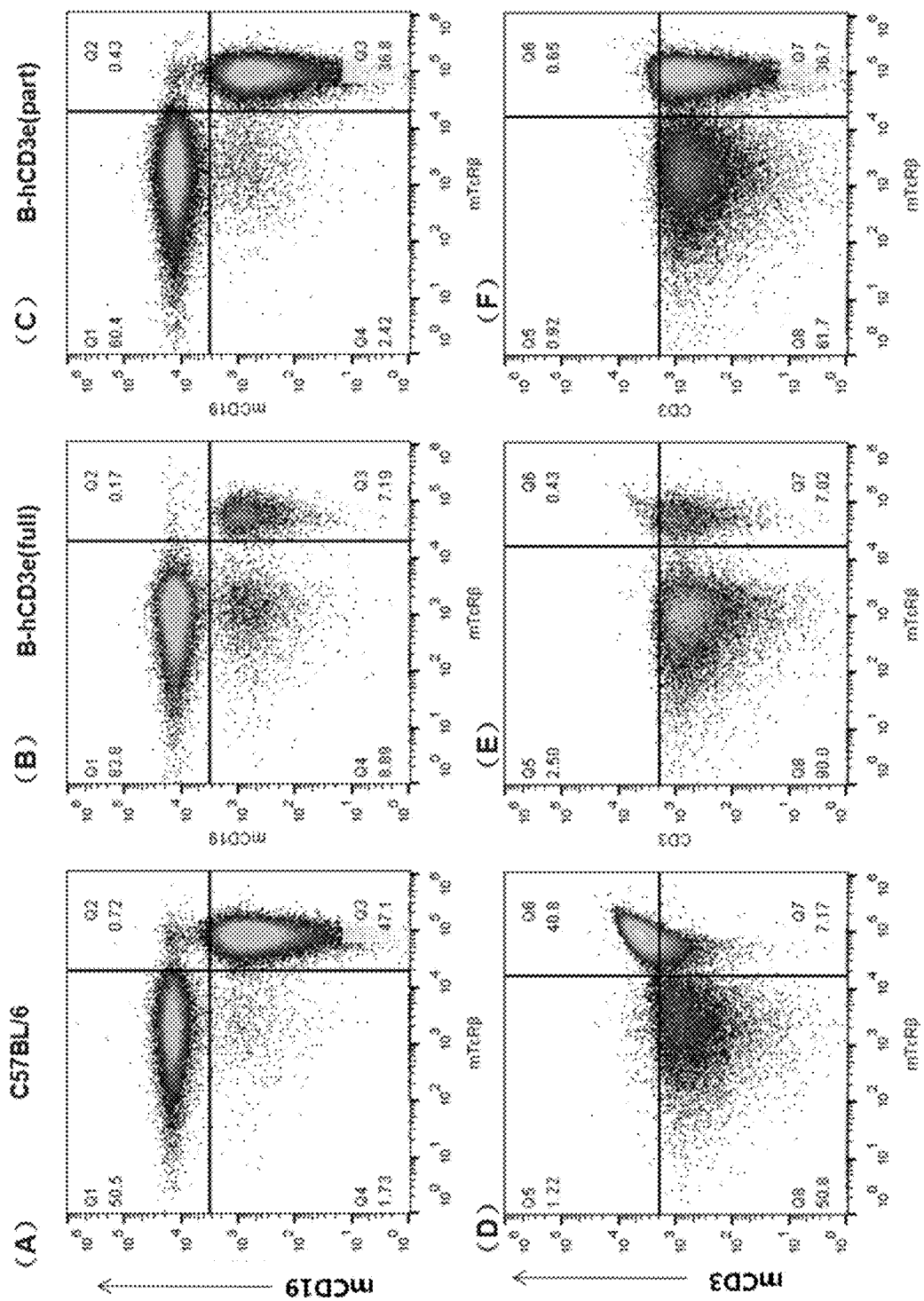
FIGS. 21A-21F are cell flow cytometry results for mesenteric lymph nodes.
Figures 22A, 22B, 22C, 22D, 22E, 22F:
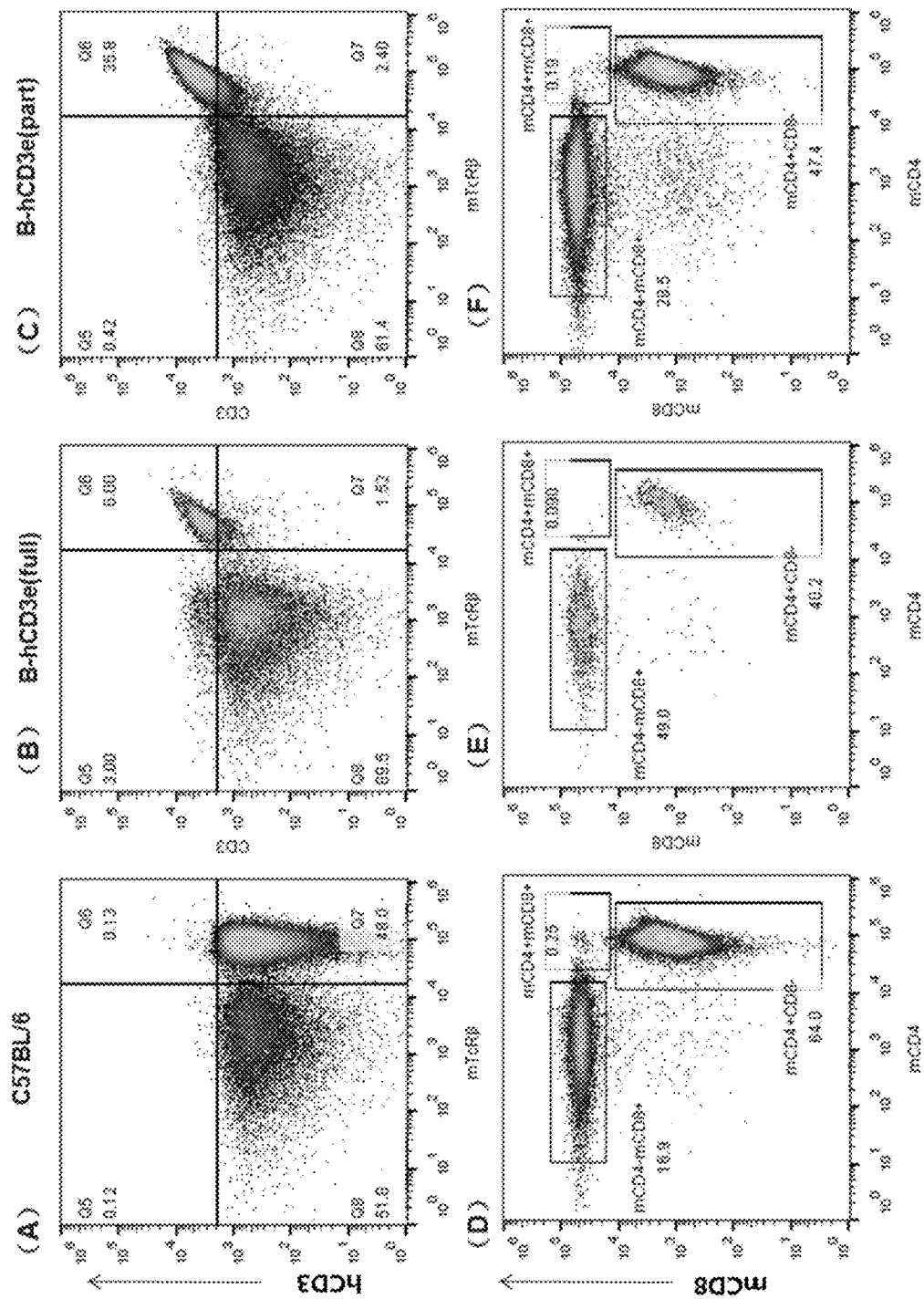
FIGS. 22A-22F are cell flow cytometry results for mesenteric lymph nodes.
Figures 23A, 23B, 23C, 23D, 23E, 23F:
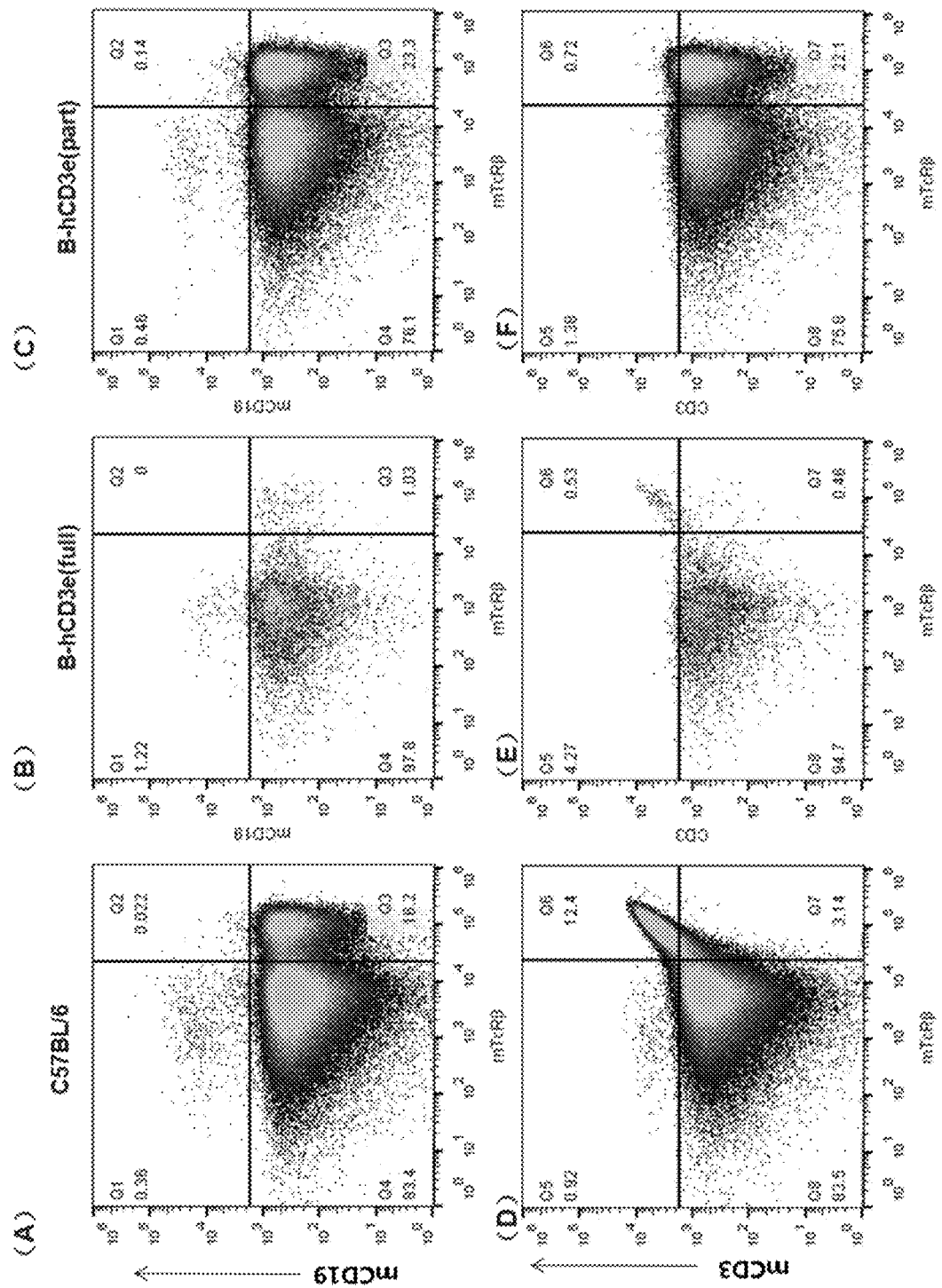
FIGS. 23A-23F are cell flow cytometry results for the thymus.
Figures 24A, 24B, 24C, 24D, 24E, 24F:
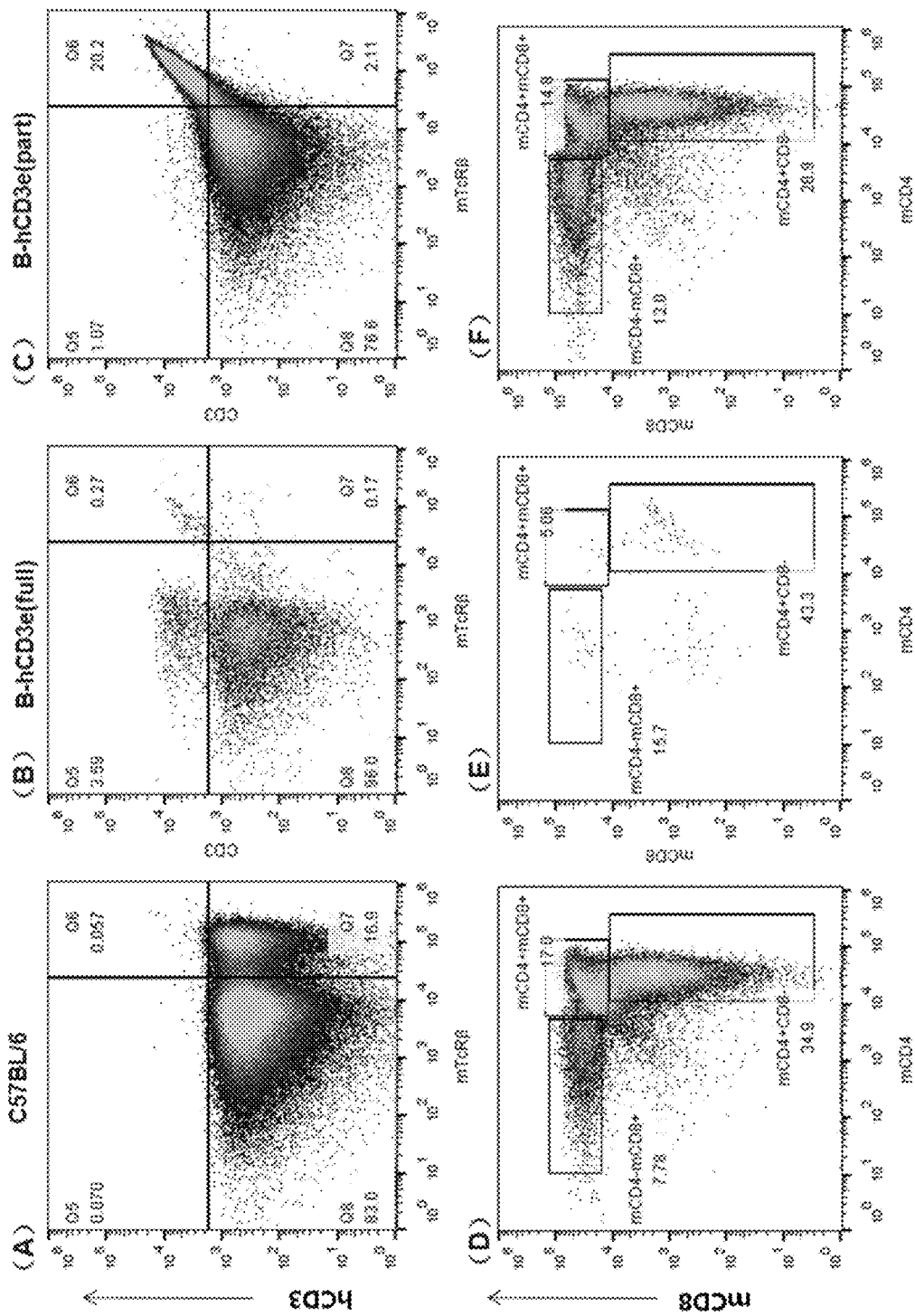
FIGS. 24A-24F are cell flow cytometry results for the thymus.

In the second group, extracellular proteins were stained with (1) mTcRβ PerCP and mCD3 PerCP or (2) mTcRβ PerCP and hCD3 PerCP. Cells were washed once with PBS before flow cytometry analysis. The results of the flow cytometry analysis (FIGS. 14A-14C) showed that mCD3 can be detected in the wildtype C57BL/6 mice and the humanized mice. However, humanized CD3 were only detected in the humanized mouse (FIG. 14F).

Humanized Homozygous Mice

The F1 heterozygous mice were further mated to each other to obtain F2 generation homozygous mice. Experiments were performed to analyze the thymus, spleen and lymph node cell subpopulations. One humanized homozygous mouse (hCD3-part version; partial sequence replacement) and one humanized homozygous mouse (hCD3-full version; full sequence replacement) were selected, and one wild type C57BL/6 mouse (3-4 weeks old) was selected as a control. Whole blood (with an anticoagulant) was collected. The mice were then euthanized and the spleen, thymus, inguinal lymph nodes and mesenteric lymph nodes were collected. Flow cytometry was performed. The results are shown in FIGS. 15-24. The results again confirmed that the expression of humanized CD3e in both humanized mice, indicating that the genetic modification was successful. In addition, it was found that the thymus of humanized CD3e (hCD3-full version) mouse was smaller than that of wildtype mouse, whereas the thymus of humanized CD3e (hCD3-part version) mouse was similar to that of wildtype mouse.

Example 9. Pharmacological Test of Humanized CD3e Animal Model

T Cell Activation

Figures 25A, 25B, 25C, 25D:
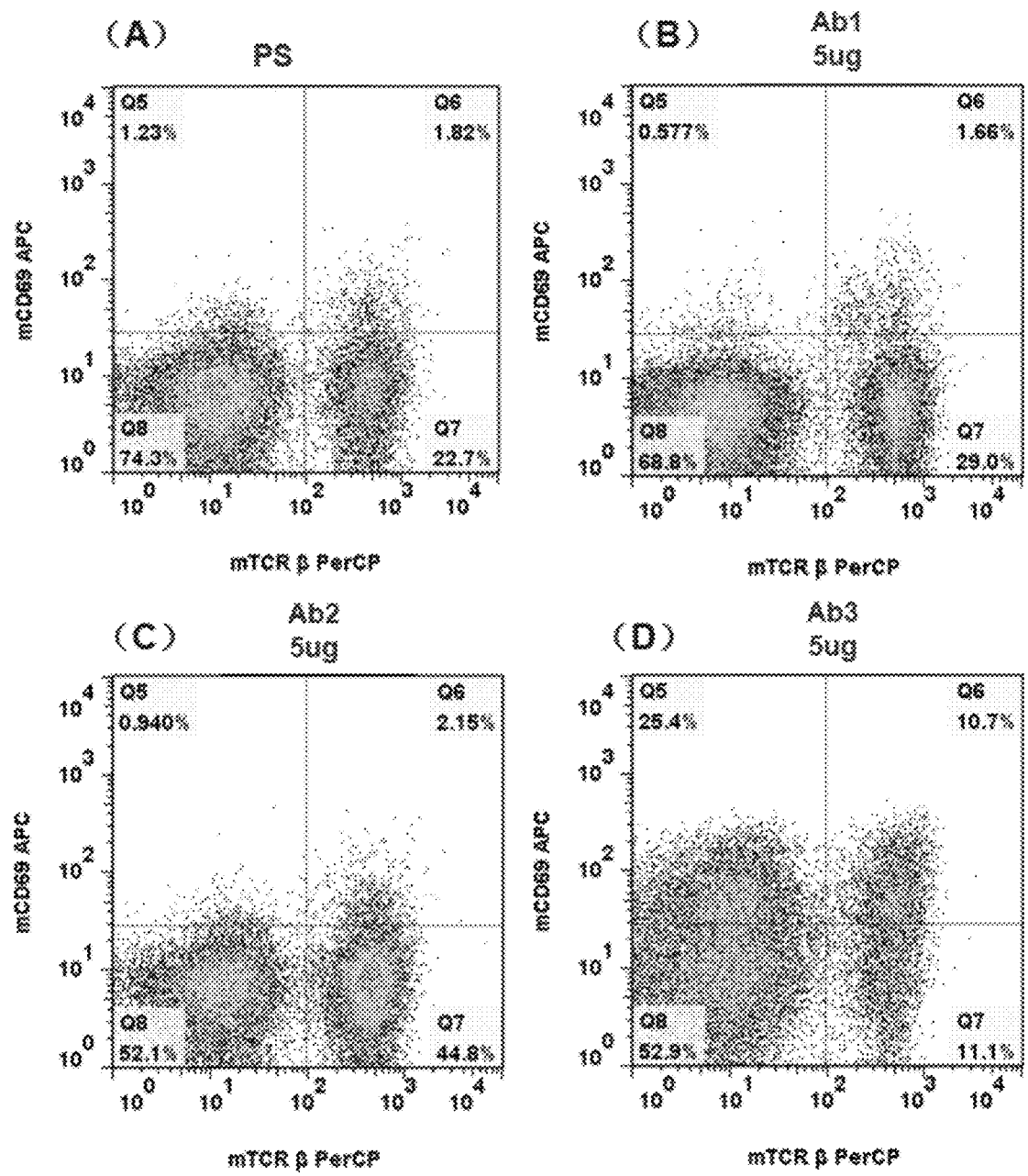
FIGS. 25A-25D are flow cytometry results for spleen cells of humanized CD3e heterozygous mouse (hCD3-part version) stimulated by anti-hCD3e antibody (Ab1, Ab2, or Ab3). The spleen cells were stained by mCD69 APC and mTcRβ PerCP.
Figures 26A, 26B, 26C, 26D:
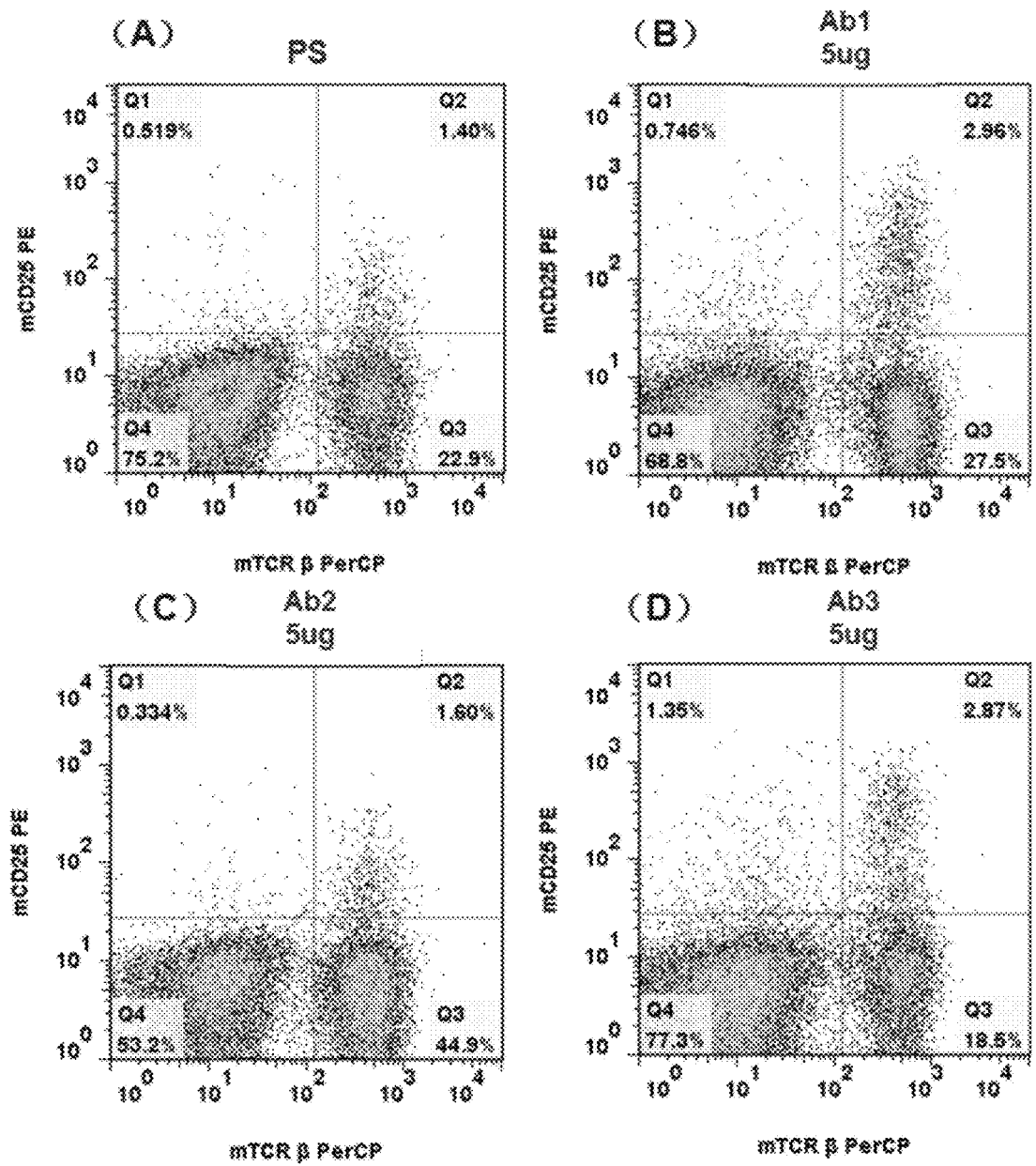
FIGS. 26A-26D are flow cytometry results for spleen cells of humanized CD3e heterozygous mouse (hCD3-part version) stimulated by anti-hCD3e antibody (Ab1, Ab2, or Ab3). The spleen cells were stained by mCD25 PE and mTcRβ PerCP.

Experiments were performed to demonstrate how to use the humanized mouse described herein to perform antibody screening. Humanized CD3e heterozygous mice (hCD3-part version) (partial sequence replacement) were randomly divided into a control group or treatment groups. Three anti-human CD3e antibodies (Ab1, Ab2 or Ab3) were administered to the mice in the treatment groups through intraperitoneal injection at a dose of 5 ug. The control group was injected with an equal volume of physiological saline. Spleen lymphocytes were collected after 24 hours of injection and were analyzed by flow cytometry. The results are shown in FIGS. 25-26. The results showed that antibody Ab3 activated T cells more effectively than Ab1 and Ab2 under the same condition, as demonstrated by the fact that the percentage of CD25+ T cells and the percentage of CD69+ T cells among T cells were higher than the other groups. Different anti-hCD3e antibodies showed different degrees of activation of T cells in humanized CD3e mice, indicating that humanized CD3e mice can be used to screen anti-hCD3e antibodies.

Inhibiting Immune Response

Humanized CD3e homozygous mice (hCD3-part version) (7 weeks) were subcutaneously injected with mouse colon cancer cell MC38 ($5 \times 10^5$), and when the tumor volume grew to about 150±50 mm$^3$, the mice were divided to a control group and treatment groups based on tumor size (n=6/group). The treatment groups were randomly selected for being treated by InVivoMAb anti-mouse PD-1 (CD279) (mPD-1) antibody (10 mg/kg), anti-hCD3 antibody Teplizumab (2 mg/kg), or anti-mCD3e antibody (2 mg/kg); the control group was injected with hIgG (2 mg/kg). The frequency of administration was twice a week (6 times of administrations in total). The tumor volume and the body weight were measured twice a week. Euthanasia was performed when the tumor reached 3000 mm$^3$.

Table 14 shows results for this experiment, including the tumor volumes at the day of grouping (day 0), 14 days after the grouping (day 14), and at the end of the experiment (day 21), the survival rate of the mice, the number of tumor-free mice (non-existence of tumor), the Tumor Growth Inhibition value ($TGI_{TV}$ %), and the statistical differences (P value) in mouse body weights and tumor volume between the treatment and control groups.

TABLE 14

|  |  | Tumor volume (mm$^3$) | | | Survival | Non-existence of tumor | $TGI_{TV}$ % | P value | |
|---|---|---|---|---|---|---|---|---|---|
|  |  | Day 0 | Day 14 | Day 21 | | | | Body weight | Tumor Volume |
| Control | G1: hIgG | 121 ± 6 | 784 ± 119 | 1982 ± 350 | 6/6 | 0/6 | N/A | N/A | N/A |
| Treatment | G2: anti-mPD-1 | 121 ± 6 | 475 ± 78 | 785 ± 164 | 6/6 | 0/6 | 64.3 | 0.332 | 0.011 |
|  | G3: anti-hCD3e | 120 ± 7 | 1571 ± 174 | 3235 ± 351 | 6/6 | 0/6 | −67.4 | 0.886 | 0.030 |
|  | G4: anti-mCD3e | 121 ± 6 | 929 ± 185 | 2257 ± 545 | 6/6 | 0/6 | −14.8 | 0.826 | 0.680 |

Figure 27:
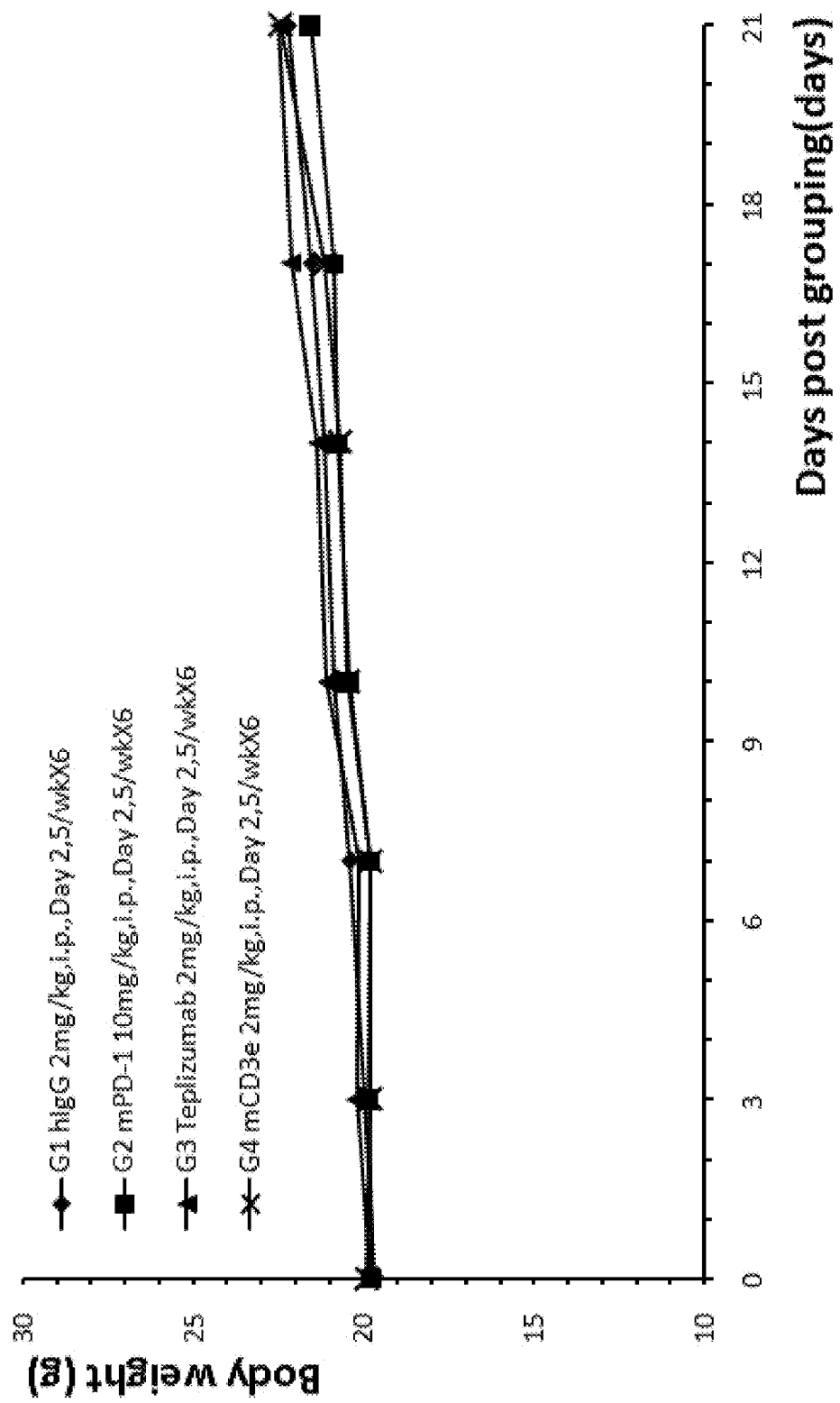
FIG. 27. The average weight of the different groups of humanized CD3e homozygous mice that were injected with mouse colon cancer cells MC38, and were treated with anti-mPD-1 antibody, anti-mCD3 antibody, or anti-hCD3 antibody Teplizumab.
Figure 28:
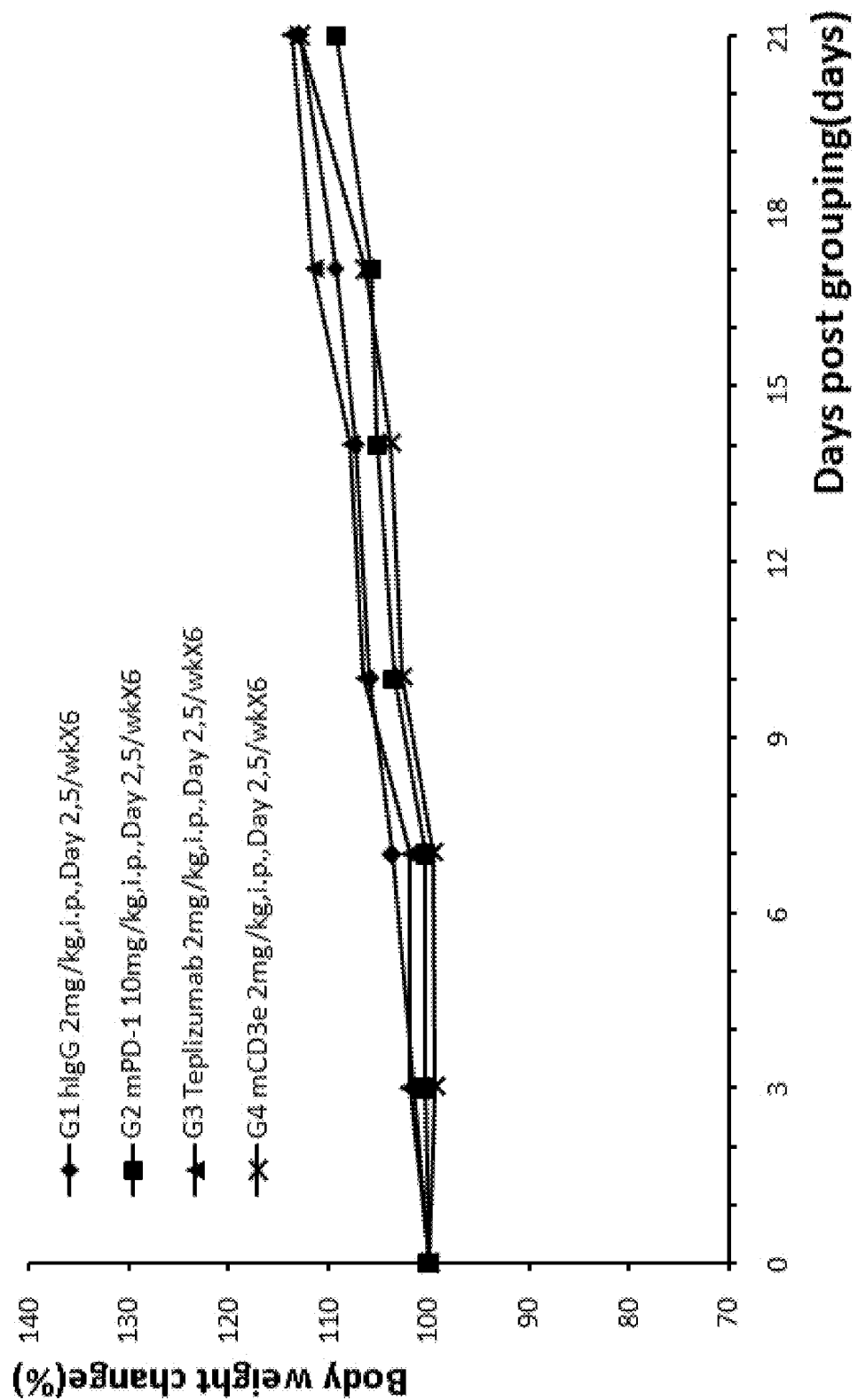
FIG. 28. The percentage change of average weight of the different groups of humanized CD3e homozygous mice that were injected with mouse colon cancer cells MC38, and were treated with anti-mPD-1 antibody, anti-mCD3 antibody, or anti-hCD3 antibody Teplizumab.

Overall, the animals in each group were healthy, and the body weights of all the treatment and control group mice slightly increased, and were not significantly different from each other (FIG. 27 and FIG. 28). The results indicated that the use of antibodies were well tolerated and did not cause obvious toxic effects.

Figure 29:
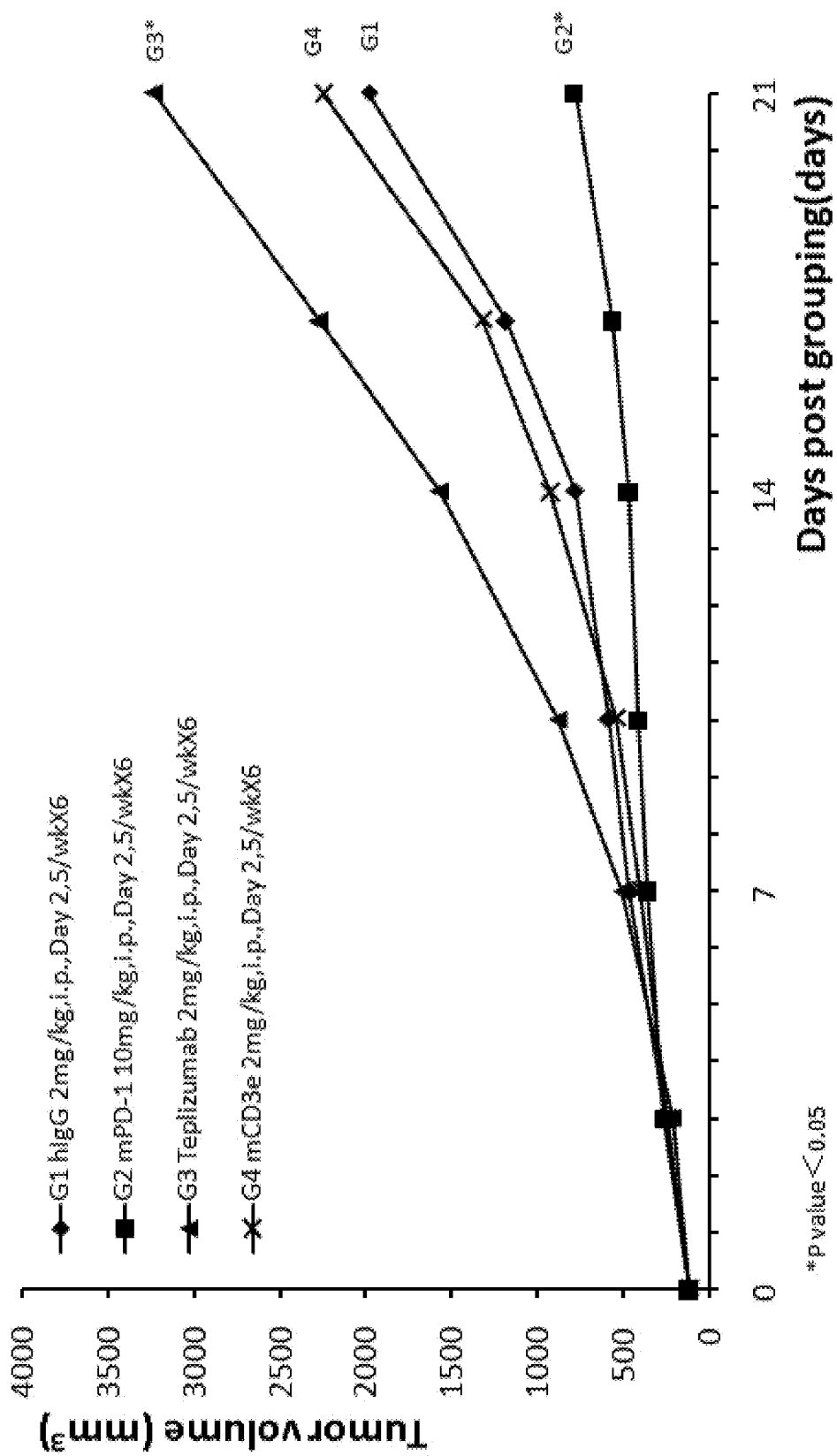
FIG. 29. The average tumor volume in different groups of humanized CD3e homozygous mice that were injected with mouse colon cancer cells MC38, and were treated with anti-mPD-1 antibody, anti-mCD3 antibody, or anti-hCD3 antibody Teplizumab.

The tumor in the control group continued growing during the experimental period. The tumor volumes in G2 were smaller than the control group (FIG. 29). The tumor volume in G3 were larger than the control group, however, the tumor volume in G4 was similar to G1, indicating that in humanized mice, only anti-hCD3e antibody can promote tumor growth.

Further analysis were performed to determine the percentage of T cells (TCRβ/CD45+) in peripheral blood cells and the percentage of B cells (CD19+/CD45+) in peripheral blood cells. The results show that the TCRβ % (the percentage of T cells) in the G3 group was significantly lower than the that in other groups (data not shown). It may be because the anti-hCD3e antibody can cause activation induced cell death (AICD), which cause the proportion of T cells decreased significantly.

In a related experiment, wild type C57BL/6 mice were used. The mice were divided to a control group and treatment groups based on tumor size. The treatment groups were randomly selected for being treated by anti-mPD-1 antibody (10 mg/kg), anti-hCD3e antibody (2 mg/kg), or anti-mCD3e antibody (2 mg/kg). The control group was injected with hIgG (2 mg/kg).

The results showed that the tumor volume in the anti-mPD-1 administration group were smaller than the tumor volume in the control group. And the tumor volume in the anti-mCD3e antibody significantly increased. The tumor volume in the anti-hCD3e group was similar to the control group, indicating that only anti-mCD3 antibody can support tumor cell growth in wild type mice. Further analysis showed that the TCDβ % in the anti-mCD3 antibody group was significantly lower than the other groups.

Example 10: Mice with Two or More Humanized Genes

Mice with the human or chimeric CD3e gene (e.g., animal model with human or chimeric CD3e prepared using the methods as described in the present disclosure) can also be used to prepare an animal model with double-humanized or multi-humanized genes. For example, in Example 5 and Example 7, the embryonic stem cell used in the microinjection and embryo transfer process can be selected from the embryos of other genetically modified mice, so as to obtain double- or multiple-gene modified mouse models. The fertilized eggs of mice with human or chimeric CD3e gene can also be further genetically engineered to produce mouse lines with one or more humanized or otherwise genetically modified mouse models. In addition, the genetically engineered CD3e animal model homozygote or heterozygote can be mated with other genetically modified homozygous or heterozygous animal models (or through IVF), and the progeny can be screened. According to the Mendelian law, there is a chance to obtain the double-gene or multiple-gene modified heterozygous animals, and then the heterozygous animals can be further mated with each other to finally obtain the double-gene or multiple-gene modified homozygotes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified, non-human mammal whose genome comprises a replacement of a nucleic acid sequence encoding a portion of the extracellular region of an endogenous CD3e with a nucleic acid sequence encoding the corresponding portion of the extracellular region of a human CD3e, wherein the replacement results in a sequence encoding a chimeric CD3e comprising an amino acid sequence that is at least 95% identical to amino acids 1-126 of SEQ ID NO: 7, at an endogenous CD3e gene locus, wherein the chimeric CD3e associates with endogenous CD3γ and endogenous CD3δ, forming a functional CD3 complex in the mammal, wherein the non-human mammal detectably expresses the chimeric CD3e on the surface of one or more activated T cells.

2. The mammal of claim 1, wherein the sequence encoding the chimeric CD3e is operably linked to an endogenous regulatory element at the endogenous CD3e gene locus in the at least one chromosome.

3. The mammal of claim 1, wherein the chimeric CD3e comprises the amino acid sequence of SEQ ID NO: 10.

4. The mammal of claim 1, wherein the mammal is a rodent.

5. The mammal of claim 1, wherein the mammal is a mouse.

6. The mammal of claim 1, wherein the mammal does not express endogenous CD3e.

7. The mammal of claim 1, wherein the mammal further comprises a sequence encoding an additional human or chimeric protein.

8. The mammal of claim 7, wherein the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), TNF Receptor Superfamily Member 4 (OX40), CD3δ, CD3γ, CD40, or CD278.

9. The mammal of claim 1, wherein the chimeric CD3e comprises a human signal peptide.

10. The mammal of claim 1, wherein the expressed chimeric CD3e can be recognized by an anti-human CD3e antibody or antigen-binding fragment thereof.

11. The mammal of claim 1, wherein the mammal is homozygous with respect to the sequence encoding the chimeric CD3e at the endogenous CD3e locus.

12. The mammal of claim 1, wherein the chimeric CD3e consists of the amino acid sequence of SEQ ID NO: 10.

13. The mammal of claim 1, wherein the chimeric CD3e comprises an amino acid sequence that is at least 95% identical to SEQ ID NO: 10.

14. A genetically-modified, non-human mammal whose genome comprises a replacement of a nucleic acid sequence encoding the extracellular region of an endogenous CD3e with a nucleic acid sequence encoding the corresponding extracellular region of a human CD3e, wherein the replacement results in a sequence encoding a chimeric CD3e comprising an amino acid sequence that is at least 95% identical to amino acids 1-126 of SEQ ID NO: 7, at an endogenous CD3e gene locus, wherein the chimeric CD3e associates with endogenous CD3γ and endogenous CD3δ, forming a functional CD3 complex in the mammal, wherein the non-human mammal detectably expresses the chimeric CD3e on the surface of one or more activated T cells.

15. The mammal of claim 14, wherein the sequence encoding the chimeric CD3e is operably linked to an endogenous regulatory element at the endogenous CD3e gene locus in the at least one chromosome.

16. A genetically-modified, non-human mammal whose genome comprises a replacement of a nucleic acid sequence encoding an endogenous CD3e with a corresponding nucleic acid sequence encoding a human CD3e, wherein the replacement results in a sequence encoding a chimeric CD3e comprising an amino acid sequence that is at least 95% identical to amino acids 1-126 of SEQ ID NO: 7, at an endogenous CD3e gene locus, wherein the human CD3e associates with endogenous CD3γ and endogenous CD3 δ, forming a functional CD3 complex in the mammal, wherein the non-human mammal detectably expresses the human CD3e on the surface of one or more activated T cells.

17. The mammal of claim 16, wherein the sequence encoding the human CD3e is operably linked to an endogenous regulatory element at the endogenous CD3e gene locus in the at least one chromosome.

18. The mammal of claim 14, wherein the mammal is a mouse.

* * * * *

SEQUENCE LISTING

<160> NUMBER OF SEQ ID NOS: 40

<210> SEQ ID NO 1
<211> LENGTH: 5246
<212> TYPE: DNA
<213> ORGANISM: Artificial Sequence
<220> FEATURE:
<223> OTHER INFORMATION: Mus musculus

<400> SEQUENCE: 1

```
ctcagatgtt cctgcaatca tgcctttgct ctgccaccat ggactctggc tctaaaactg      60
tgatccccag gttaagggct ttcttttata aattgccttc actgtggtgt tatcacagtg     120
ataggaaagt gactgaaaca gacagtaaat gctgagatag gacagttgtt tatgccagag     180
ctgggccata gtaagaaaaa cctggacccc tgaaactgat gggatgacat gggatgggat     240
ggcatgagac aggataacat gggatggggt agaagggatg agaggagaaa gggtaggatg     300
agagaggaag ggagaggagg ggaagaatgg gaagggaggg gatggaatag gatgagagag     360
gagaaagagg aggagagggg aggggaggga ttgaatgaga agggatggga tgcgagtctt     420
gattttccag atcgtccttg aaccattagg cctacagaat tggaccacac atttaaaggc     480
ctcacatgat gtgtcctata aggcaccact aaccccattc ccctcctggc catcaaacct     540
gttactagag ccaattctca aggtgactca actggttaag tactagagag gttaatgtgc     600
caagtatcgc aggctcaggc tcgtgctttg aaagctcagt ccccagttaa tgataatgct     660
```

```
ttaggtggct gtggaattgt taggggggtgt ggctaagctg tcagatccag gaagtcacaa    720
ggttggaggg gtgcagcaat aatccactgt gagatagaat gaatgaactc tatgtgggag    780
atgaatgcca ctgctactgg agttcatacc caagactctt aagctgtggt ggtttgtata    840
tgctcagccc agggactggc actattagaa ggtgtgaccc tgttgagtag gtgtgtcact    900
gtgggtacgg gctttaagac cctcatccta gctgcctgga agccagtctt ccactagcag    960
ccttcagatg aagaggtagg actctcagct cctttggcac catgcctgcc tggatactga   1020
catgcccttg tcttaatgat aatggactaa acctctgaac ctgtaagtca gccccaatta   1080
aatgttgtcc ttataagagt tgccttggag ctggaaaga tggctcagtg gttaagagta    1140
ttgactgctc ttccaaaggt cctgagttca attcccagca accacatgat ggctcacaat   1200
catctgtaat ggggtctgat gccctcttct ggtgtgtctg aagacaccta cagtgtactc   1260
atataaataa aataaatctt aaaaaaaaac aaaaacaaaa acaaaaaagt tgccttggtc   1320
atggtatctg ttcacagcag taaaacccta actaagacag aagtcatcta tcacttcttc   1380
accctcagat cagactgtgg ctggctacat agcaagctac tccctaagca acggctggaa   1440
gaggagggtg aagctgagct tgttgtcaa atctcacctg agcatgtgag tgaaagtcaa    1500
atatgaaaag ctgcaactgt gcagctccac tcatggctga agacagccat aagaggagac   1560
cctcccactg gcagggacct ggcattgtac ctgatcatct actttatatg ggaagggaaa   1620
tggcctaacg tcctcagaca caccagaaga gggcatcgga tcccattaca gaggttgtga   1680
gccaccatgt ggttcctggg aattgaactc aggacctctg gaagagcagc cagtgctttt   1740
aaccactgag ccatctctcc aggcccccac ccccaccacg agacctcact cctaactaag   1800
gagctattga cagttagtga ccactaagag aggaagaaca cttttctttg ggggtgcctg   1860
cttgtaggtt ggccttgccc cagtggatga ccttacactc actcacttcc acactcatgc   1920 accccctgatt aggatttact ggactcagag gactagtaat aataattggg gaagacaatt   1980
taggtggata aaatctaaat acattatatt catgttcaaa attttcaaag acaaaataaa   2040
aagtttaaaa gaaaacttct ggagggctgg agagatggct gactgctctt ccagaggtcc   2100
tgagttcaat tcccagcaat cacaaccacc tgtaatggga tctgatgccc tcttctgttg   2160
tgtctgaaga cagcgacggt gtactcatat acataaaata aataactaaa tcttttaaaca   2220 aagaaaagga aaggaaagtt ctggttagag agatgcctca gaggttaaga gcactcgatg   2280
ctcatataga agccccgagt tcagatccta gcacccacct ggcagctaac agcagtctgt   2340
aactccatct tccaggacct gatgccctgt tctggcttcc tcaggtactg cacacacatg   2400
atatacatac aatgcatgct ggcaaagcac tcgtgcgtat aaaacatctt ttttataaaa   2460 agggggtccat caatatcctg aagggactgt ttgaggatga gggaagcagg tgacggggca   2520
ctgtcacctg aactggatct gcgtgacact gcctaggacc cccagctgat agggttgctg   2580
ccccctgaga gtggcaaaca gccagaccat aggtatcacc ctcgggagag cctactgcct   2640
cacccaagtc cacaccacct ccggggacca gcttccatcc aactactggg taacgtgccc   2700
cttgccatgc cataactcaa gaaatcagag acagcgcttt actgctctcc tccctcctgg   2760
cggctctcat gctcttcctg acctctcttc ctcaatgtct ttaaggtttt tagaaggaaa   2820
aagtttaatt atggaagtga tacatcattg cttctcagac gtttggctaa catcaagtgt   2880
ggaagtaaga ccgtgcatgt attaaaacca atgaagagca taggagaggt gtataataac   2940
accacgcccc actcatccca ccactatgcc ttttctcagg ggcacaacca cctcaacgga   3000
```

```
cccccttcctc tgggcttatc ttcacatccc acaaagtgca cagacatcct ttgagttccc    3060
tgggaaacaa accttgaggt ggagatttgt gtgcaggtgg ctcgtgggaa tgcaggacac    3120
ctgcaaagga gagagggaag ccacaaggca gacagagaaa gtcaacttca gggagcgact    3180
tcagggagcg gcagctcaga ggcctctgct tgggcctctg tgctcatgag ctcactgcag    3240
ctctggttac catgcagcat ttcagcaggc agcaggtaac tgcactcaga gggtgggggg    3300
cgggtgaggg gggttgggga ggggagagat gtacggggga tgtctgaggg cagtgaaagg    3360
gagaaatcaa ggtggatatg atcaagatac attacataca tgtatggaat tgtcggagaa    3420
taaataaatc ttttttgaaa aaggggaga gagcgccaga gagtgagaca gcaaggcaga    3480
aagcaaaccc caactcaaaa acaaggcgga aaggggactc agactccaaa ctaaggtaga    3540
aaggggatc gagaaagagc gcttagtatc catctctggc ctccacaagc acctcacacg    3600
tctgcacact caaactccat acatacatga aaagattttg taatttccat taattaattt    3660
atttactcat tttacatccc aatctcagcc cccctcctcc aagccccccc tccaagtccc    3720
cgcccctcag atagccgctc ccccaccccc tccttcccct tcccatctga aagagggag    3780
gtccctctgg gcactgagtc tgatactatc ccttatctgg agatgtgggt gggcaaaaag    3840
aatgtaagag tagaaactag ggagaagggc tgtgaagcac tgccttctag tagctgtggc    3900
agccagcagt ggatccacat gcaactgggc ttatcaacag tcaatcatgc attggggcgg    3960
gacttctggg gctctaagcc tttctactga actataggtt atagatggat tcagaaagaa    4020
aggcagccgt tttcttcagt cctgtaccca ctgaggagct cttcaggctc cttcagtagt    4080
tagttccaaa tccactgtca cacagctaac tctcgttaaa cccagtagat atatcaagaa    4140
gcggagccag agagatacct caacagataa agttgtttgt ggttaaaaac ctaaagacct    4200
gaattgaaac ctgggactca catgttagag agaatccctc aagctaccct cgacttccac    4260
acatgctgtg gcaagtctat gcccacacat atacacatat aataaatagg taaataaata    4320
acgtaaaact ttttttcgt aaaacttttt aataaaagac ttgtcgagaa agggagatta    4380
atcatcagaa agtgtgttac aattgtatga aattatcaaa gagctaagtc aataagcgtt    4440
ttttacaaag aaaaagattg ttgcttataa ctcaggaagt acttatgcta gattttaaat    4500
aataatgcta aaagctaccc tagtgggtgc atgagtaaag cccctagcat agtgtcagta    4560
caaagacagg agctatgtga ctctctcatt gtccagcaac tgcccagcat gtgcaatcaa    4620
aggccaggac ggctacatgc taaaaatcct gtctcaaaga aagaaagaaa agaaaagcaa    4680
gccccctcgaa gattattaat gagacggctc cactccatcc tgctgctcag acccaagggc    4740
accataacag aaggcagata ctgagtgctt caacgtcttc ctgcctccgc tggaggggtt    4800
atgcataagg aaggctccct cagtgtggag gtgctttgca cagggcacaa gtaggtgttt    4860
ttcacagcac tctcggggc ttgctagagc cccccttgtt catccttatg ggaaggctgt    4920
gaggcgcgga tttcctcagt taaccaaggc ggaggcttct gcctcaaaca tttccaagtg    4980
acgtggagca ggcgggccct gagtcccctc tacacttcct gtgtggggtt cagacacctg    5040
cctcccctgt ctgcgtctgg tgccttcttc agaaatggta agtctctcct tgtgaagtgc    5100
cccccactct ccttcatcct actatggcaa ccaatgatcc agggtctttg catgcagcca    5160
ctgtgttgaa aacctcatct gtttcttttt cagaagtaat gagctggctg cgtccgccat    5220
cttggtagag agagcattct gagagg                                        5246

<210> SEQ ID NO 2
<211> LENGTH: 3547
```

```
<212> TYPE: DNA
<213> ORGANISM: Artificial Sequence
<220> FEATURE:
<223> OTHER INFORMATION: Mus musculus

<400> SEQUENCE: 2
```

| | | | | |
|---|---|---|---|---|
| aagtgctgct | gaacagagcc | agggaagacg | agaaaagccg | tgcgtgcgtg cgtgcgtgca | 60 |
| tgcatgcggt | tccctcctgc | cctggaggca | gctgtctgaa | gccccaagca gtagtggtta | 120 |
| tacagcagga | tgtgggctgt | gctgggagtg | aggatgagag | aggtgtggtg gtagccacgg | 180 |
| accagacact | ggaggctatc | gatgagagaa | tgtggtcctt | ggtctcccac atactctgct | 240 |
| tgcaggagag | aggaacccag | agcccaagca | agctatccta | ggccagctca agccatcgga | 300 |
| ctctcttctc | cacctttctg | ccctcagaca | catccctgct | gacttaaggg ctatttgtta | 360 |
| tgtgacttta | gcttctgtgc | ctagcagcgg | tccacacact | gtccatactc tgccttggat | 420 |
| ttgtaactac | agttcctgct | agttggtctc | cactaaactg | tcaccttttc ctctctaggc | 480 |
| atcgatgctt | atgttaaaat | gagtcttgat | gattttgcct | atcaccaaac actaataagc | 540 |
| aggtggcaga | ttttgtcctg | catatatttg | atgtgtccag | tcaaggacat tcgtagctca | 600 |
| acatgataaa | aagcattaac | atttggtgtt | tactgagaat | ttaccatgct ccagaagttg | 660 |
| ttatagccct | atatgtgctg | tctcatttaa | tccttataga | gacgccacaa atatatgttg | 720 |
| tcatcttcta | tatgtgggc | tcagagaggt | agcatcattt | atccatgtga agtgaaatgc | 780 |
| agggctacaa | ttagcagcta | gagatgtcta | attctggggc | actttttttt tttttttgg | 840 |
| atacagagtc | tcactatgta | gctctggctg | tcctagaact | atgtatgtat gaactaagca | 900 |
| tgtagactag | aaactatgta | gaccagactg | tcctcaaact | cacagagatc ctcctgcctg | 960 |
| tgcctctgct | tcccgagtgc | caggattaaa | agtgtgcact | agtaatgctc tgcttctaac | 1020 |
| tccagcactc | tggcacctac | ccactatgac | cgagaccatg | gcaatgttct tcttcctacc | 1080 |
| atatgccttct | ggaaaaaatg | gaggagttgg | agatggagca | gaaacctaga gtctgttttc | 1140 |
| tatatgggtc | ggaggcagga | tacaatagga | tgaaggcaga | tgccgtgtca aggaaagtga | 1200 |
| gggtcatgca | aaacacagct | cttactccaa | atagaatagc | agttagttta ttctggagcc | 1260 |
| agcaagatgg | cttagcaggt | gacagtgctt | accaccaagc | ctgaagaccc gagtttgatt | 1320 |
| cccagaacct | acctggtaga | agaaaaccaa | cttttcataaa | ttatcctctg actgctaacc | 1380 |
| ccaccaggct | agaagagcac | taccacaatt | tatgagccaa | atttgaagca gcttttttac | 1440 |
| tggccaagtc | tatggatact | ggccagatcc | atacgcacta | tctatcccca gagctccagc | 1500 |
| cctttataag | gcaggggcta | taaaggcaaa | gcccataaga | ctaccgactt cttcccacct | 1560 |
| tcatctagtc | agggacaagc | atacaccctg | ccacactttc | tgcctgtgaa cctgctggca | 1620 |
| atgggtaagc | aagcacatcc | tgtgcagctg | gggcaaccca | gcttctttat agaagcaaaa | 1680 |
| actcccggct | tgttatcttc | catgatcaac | agcccccagc | atcccaggaa gttggctgtt | 1740 |
| cttgagcaag | tggggcttac | aggttagagg | cattttgttt | aatagttaga tctcttaagc | 1800 |
| acagtaactt | atacttagac | ataatgttag | cctcttgcgc | gcgccggact ggccagcagt | 1860 |
| aacaacgctg | caacaggatc | cttctgcaca | tgtttattgg | gagagcttga ttgtagaggc | 1920 |
| gaagagaccc | cgagcccaga | actggtgctg | cttatatagg | cctaggagat gcgtgtctca | 1980 |
| cacccggatt | ggctatgcac | tacgcctcat | ttgcatgttc | ctcatctgat tggctactct | 2040 |
| ctctctctct | gtacctcaca | gagcctcatt | atcatacctc | atttgcatgt ctcacatctg | 2100 |
| attggttata | ttctcaaagc | ttcattatca | tgcccgggcc | aggcagtgtc tttgcaaaaa | 2160 |

```
actttactgc atatgtacac attggttgtt tgtccaaact tatgcgtggt ggccagcagt    2220
agtcagcgcc actctgcaac ggcacatgtg gcttcccaca ttagccatca tatttctttc    2280
ttgagctgtg tatcctgagt caaatccttg actctaaagt gggtagcggc tcaaattaag    2340
atctaataac catcagctta atggcaccca gacagcaatt tacatatata gttaagatat    2400
taatgatgca aggttattag taactagcag aaacagaagg gcaaaggcct tgtgatggct    2460
gacagcagaa ctactaccta agtggagccc aaaaatgaga atgggagcca gtcatttgtc    2520
tcatcttggg gcctgttttt ctgtaggttt gggtttgctt tgttttgttt tgttttgttt    2580
tggaggggtt gtttgttttt ttagtacatt cagactatct cttatgattt cctgagtggt    2640
ttgcaaagaa gcaacaattt ttttaaacca tacaataacc tcatttttaca tagagcaggt    2700 cgagtgtcct atcatgttct atcatatttc agctaataaa tctacttgtt aatagatctg    2760
ggtctatttg gctttagcag gtacctatcc tcatatgtca ataggctcta taggtgccta    2820
tttgtcctat ataccgtgga gtttcctttt aatctaacct tccagccttt tgtagagggt    2880
aaagggtaat gtactctctt ctttaactac ttcctgtgga aattaggaca tcactgacag    2940
ggctcaggaa ggctggaatg ctagtcaaag gccaggaggg gattcagcag aagcattggg    3000
ttagctggcc cagctgaaga gacagggagc aactatatct gctggactgt tttgtccaca    3060
tcagcattca gcaagtccag ggcttttagt cacttggagc aggttgtgta gtccacagct    3120
gattcctgga tggtgtttgt cagccaagtg gaaattcagc tgggacaggt atagaccacg    3180
gacagaagtt taccagtgtt tgtaatttgt gcttaaaatc cacgttgtag aaagggcagc    3240
tggcaggtgt ctgcaaaaca tctggagtgg actcatgcct ttgagtcata gagaaagctt    3300
tcacttaaaa agcttgaaca ttctttttct gtccagtggt ctaggtatag tgatgcgaaa    3360 taccttttaaa tctacactta gaagacaacc aaaggaattt aaaaccttga gctcatggct    3420
gataatggca gtcagcgctt tgcagcttta tcagaactcc actgatgaag gttaaaactc    3480
tgaacgtttg gaaccttagc atgatgacaa catagcaaga aggaaaggca tctgaaacat    3540
ttcttgt                                                             3547
```

<210> SEQ ID NO 3
<211> LENGTH: 8780
<212> TYPE: DNA
<213> ORGANISM: Artificial Sequence
<220> FEATURE:
<223> OTHER INFORMATION: Homo sapiens

<400> SEQUENCE: 3

```
atgcagtcgg gcactcactg gagagttctg ggcctctgcc tcttatcagg tgagtaggat      60
ggagtggaaa gggtggtgtg tctccagacc gctggaaggc ttacagcctt acctggcact     120
gcctagtggc accaaggagc ctcatttacc agatgtaagg aactgtttgt gctatgttag     180
ggtgagggat tagagctggg gactaaagaa aaagataggc cacgggtgcc tgggagagcg     240
ttcggggagc aggcaaagaa gagcagttgg ggtgatcata gctattgtga gcagagaggt     300
ctcgctacct ctaagtacga gctcattcca acttacccag ccctccagaa ctaacccaaa     360
agagactgga agagcgaagc tccactcctt gttttgaaga gccagatac  ttgcgtccaa     420 actctgcaca gggcatatat agcaattcac tatctttgag accataaaac gcctcgtaat     480
ttttagtcct tttcaagtga ccaacaactt tcagtttatt tcattttttt gaagcaagat     540
ggattatgaa ttgataaata accaagagca tttctgtatc tcatatgaga taaataatac     600
caaaaaaagt tgccatttat tgtcagatac tgtgtaaaga aaaaattatt tagacgtgtt     660
```

```
aactggttta atcctacttc tgcctaggaa ggaaggtgtt atatcctctt tttaaaattc    720
tttttaattt tgactatata aactgataag tcctctctac ttcacagatt aagaaattga    780
tactcaaaaa agttaaataa cttgttttaa accacatagt aagtgccgaa gccaatctgt    840
gagaccagga ctgtttgtac tctaaatggc tgcaccacat gaggcaaaat ggctcgtgat    900
ggttttattt caaagaccta gaaaacacta tcacagctgg tgctcccgtc tcagacccac    960
agcaacgatg tctccacttc ctgcttcatc ttgggtttct cacgtcttga atgtgcacac   1020
aaatcacctg gggatcttgt taaaaatgca gcttctgttt caaaagaccc agactggaaa   1080
tggagattcc gcatgtctag tacgctctca agtttattaa tctgctgctg gtcctaggaa   1140
catattgagt agcgaggggc aggatgtgac tcctgtaagg agtggccagg cattttctta   1200
gagacctgtg ttataaagta tgcttttcct taaaaaaaag aagaaggagg aggaggagaa   1260
gggccaggtg cagtggctta cgcctgtaag cccagcattt tgggggacca aagtgggaag   1320
atcacttgag ctcaggagtt caagaccagc ctgggcaaag tagtgaaacc ccatttctac   1380
aaaaaattaa aaattagcca ggcaaggtgg cacacaccta tagttccagc tacttgggag   1440
gctgaggtgg aaggatcact tgagcccagg aggtcgaggc tgcagtaagc catgatcaag   1500
ccactgcact ccagcctgga gtgtctcaaa atagataaat aaataaataa ataaataaat   1560
aaataaataa ataaaagaga cagtatcaaa gacccaatca cctctagaca tctggcatca   1620
taggaatgtg cccagtctgc tctggggata ggaaagtggg gatcctgtct cccctgtgt   1680 agaggtttca gtaaagaaa ggcctaggtg tgcagaaagc tttcaggcaa tgccagggaa   1740
actgatcatt gtaatgaatc cagggtattg ctgagtgagg gcatcctgga gggccggtg   1800 gaaatgtggt caggctcttc aatgcacagg ccctagttga tgagtaatca gggtttcaaa   1860
tatttccatc tctgtctcaa gcagaaaaca aatggaaaaa ctgaaccacc agaaaagcag   1920
agccagagat ggaacaagaa tcccagtgtt tgtacccaac caagagcgtg ttttcttcc   1980 acagacacca atgttcaaaa tggaggcttg ggggcaaaat tcttttgcta tgtctctagt   2040
cgtccaaaaa atggtcctaa cttttctga ctcctgcttg tcaaaaattg tgggctcata   2100
gttaatgcta gatgcttcct tcctctattt ccccccaaat ttcctgggaa ccctggtca   2160 ataccagcag taagttccac tgttctaggg tgtagaaatg gctgtgaccc agcagcaaga   2220
gggaaggaca tcagatgtca tcagtggtca tactgcaaca cagcccttt tctgtttagg   2280 aatgcaggta cccacaacat ttactaacac tttttttttc ttatttattt tctagttggc   2340 gtttggggc aagatggtga gatatgcttt ctttctttct tttttatgaa atcaccccat    2400
cattctttgt agttatgaat ggagctttct cttaggcctc ccacagaact tccacagagg   2460
tcaggaaaag gagtttctgc catctacccc tttgactttc ctcacaagtc tggagatatt   2520
tctagcccag aagagggaag caacagaggc aggaaataat gagtcttaac catacaaaag   2580
aaaaattgag acttaaatga agttgaaagc actaacagtt ttcatttgtt tgcatttcat   2640
atttgatgtg agattctgca gaggagacgt agccagaatg catgcacagg gttactctgg   2700
ataagctgct ggggcaacat ttggatgtgt gttcagaatc acatgtctga atactctgaa   2760
tatatgtgtg tacatgtgta tttatgcaag tgcacatgca tatgagtgtg cccggcctga   2820
acttactctc tcaaccacag cggtagagtc aggagtgttc caacattgga agcccctcta   2880
ttcaatcagc tcttccaaac tgagtgaacc aatgttgtat ttaatggcaa ccatggctgg   2940
acaccatggc tcacacctgt aatcccagca ctttgggagg ccgaggtggg cagatcactt   3000
```

```
gaggccagga gttcgagacc agcctggcca acatggcgaa accccgtctc tactaaaaat   3060
accaaaatca gccagacatg gtggtgtacg cctgtagtcc tagctactcg agaagctgag   3120
gcaggagaat cgcttgaacc tgggaggcag aggttgtagt gagccgagat cacaccactg   3180
cactctagcc tgggtgacac atcgagactg tctcaaaaat aaaataaaga caaccattat   3240
gccagcctag attccgccat gctgcctaat ttgtagtgtc cttaggagcc attttttgtaa  3300 atagtcatca gataagatgt aaggcccata acagcttttt ctatgcagct gagggaattg   3360
gaagatccat tgtttcctaa gagttgaggg aagagtccca acccacggga gcagggtctg   3420
atcttcattg ccgatagaaa cattactaat ggcttcttac tgtttccttt tcaggtaatg   3480
aagaaatggg taagaagatt tccactctat ctagcaaaag ttttcaaata tggaatgaaa   3540
tgctcataga gtacaatcac agtaacaaac cctgagaact aaaactatta aagggaaaat   3600
acaagtatct ttcaatggga tccgtatgaa acttgcctgt atttgttgct agctgtcatg   3660
tcagattata gctgtgcata tatgtatctc tgatcataca catatggatg tgggttggag   3720
ctaccatgtg tttttgtata agccatgaaa tctttgaagg cagacagaga cagtgtctca   3780
tttacctagc ccagtgtctg gcacatagta ggtgctcaat gaatattttt tgaatgaata   3840
aatgaacaaa catatgaaca cattgctaat tacctcccct caagaagctg atggtcttgt   3900
gtgagagaca ataattgaa atatagtga gttgcatgtt ataatatggg tagatacaga    3960
gtaaaatgaa gtataaagag gggagtggtc aactctactg agtgtcgttg ggaaaggttc   4020
cctgggggag gtggtccttg agctgaattt taaaggataa gcttatgttt tagggaagaa   4080
aaatatttta tgcagaagag ataaagctgt atagtatgag gataagagtc taactgagct   4140
agatcagaat gtttgaatct tggctcaact ctctacttgc tgggtgtgtt tgagtaattt   4200
acctaacttt tctgtgccac agcatcatca tggtacaatg gaaataatag tgctacctaa   4260
cttgtagggt tattatgagg accaaatgag taattcattt aaggcactta gaacattatc   4320
tgacataaaa ggcagtagga gggccgggca tggtggctca cacctgtaat cccagcactt   4380
tgagaagccg aggtgggagg atcacctgag gtcaggagtt cgagaccggc ctggccaaca   4440
tggtgaaact ccatctctgc taaaaataca aaaattagcc aggcatggtg gcaggtgcct   4500
gtaatctcag ctactcagga ggctgaggta ggagaattgc ttgaacctgg gaggcggagg   4560
ttggagtgag ctgagattgt gccattgcac tccagcctgg gcgacagagc aagactctgt   4620
ctcaaaacaa acaaacaaac aaacagacag taggtgaatt ttagctatta atacatggaa   4680
agcatgctga ctatagatga taagcattaa agtttactga gcatgtatgt tttaggcatt   4740
gctctaaata ttttacttga atttcctcat ttaattcttc caacacccct actgtacagt   4800
taaggaaaca aagcctcaaa taaatacaga aataaacaaa ataagtaaa caatccagtc    4860 ctggggatat aaatgcagat ttaggccaag tgccatggtt catgcctata atcccaacac   4920
tttgggaggc caaggcagga ggctcgcttg agctcagaag gttgaggctg cattgagcaa   4980
agattgtgcc actgtactcg agcctctgtg gcagagaaag accctgtctc tgaaaaaatt   5040 aataaaataga aatttaaaaa taaaaaaatt ttaatgcaga tttatatgat accgaagttc   5100 atttttctcaa ccattatgaa atactgtttc tggatatgta taaatctttt gtgagcacac   5160
atatcttttt ttaacttaac tttcatttta aattcagggg tacatgtgca ggtttgttat   5220
ataggtaaac ttgtgccatg ggggtttgtt gtatagatta tttcatcacc caggcattaa   5280
gcctggtacc tgttagttat ttttcctgat cctctccctc ctcccaccct ccaccttctg   5340
agaggtccca gtgtgtgtca tttccctctg tgttcatgtg ttctcatcat ttagctccca   5400
```

```
cttctaaatg agaacatgtg gtatttggtt ttctgtcact gtgttagttt gctaaagata    5460
atggcctcca gtcccatcca tgttcctgca aaggacgtga tctcattctt ttttatggct    5520
gcgtagtatt ccatggtgta tatgcagcac attttttat ccagtctacc actgacaggc    5580
atttaggttg attccatgtc tttgctattg tgaatagtgc acaatgaaca tacgtggagc    5640
acatttctgt ctaagcacag acatctagac ccttgtgtga gcatgagtta agtctaagct    5700
ctgctactga atttgtgcca ataaaagttg tgagcaattt tctttacatt ttttttcaaac   5760 aaacacaccc agcagagtat aatgtctatg tactttattt atgatttcta gttcatttaa    5820
catgtctaag aaacatccgt gttgaaaaat tatttataaa ttaaataat ataaactatc     5880 tactgtcctt atactcaact cccaattata agcaggtgga aaaacctgga gaatgttttg    5940
tttacattct gtgcagtctt tgtcagaggg ctgcctgagc aactgggtca gagtttagtt    6000
ctgctctggg agtagcagga cctcaagaag gaaaggagga aaggaagtaa cttttttcttg   6060 agcacctgct atgtgtcatt cactttcacc ttcataatcc atttaatttt cgcaaaaact    6120
ttgtgaggtt ggtgttttat ctccatttcc ctgataaaga agttgaggtt cagcaaagtt    6180
aaatgacttg ccctcagtca cacagactag ggcagatcca ggattcaaac tcagggcttc    6240
tgactcttga gtccagagct ctgtccctga cagcagcagc actgcctctc ctctcttcca    6300
gctgttatgt ccagactgta gcagaaccca gtgttccagc cacaagtttt ccaggaaata    6360
ataaaggact cctagctcca cctcccaggg caaaaatggc tgctgtggga aacacaggct    6420
ggacctacga atggcattag tggtttatta gttgatttca gttgtccaca ctaataggcc    6480
tccctctaac aaaaataatt gagagctgat tatgctcaga tataatgtaa agtgaagcca    6540 cttttttattg gaagaagcat tccctcaaaa cgtgtagagt atttcacatt atttaaaggc    6600
aaatagagag aaaattatat ggaataagaa caaagatgtt tcttctctat tatgagggac    6660
tcagttctga gaaggatttt taaattgtaa gaaataggta agtccacgaa tcagtgattc    6720
agtggtgtgg agagctttat ttctgagaag gccagtagcg ctcccttctg acaagcaaat    6780
ctaagacctg gatgacagat gacttcctgc atttggttgg ttcttttgtc attcatatct    6840
atctgtaata cagttctggc taatttaaga ggataagctt gaagacctct ggaattttttc    6900 ggctttagga cttttaaggct ttctgagctt cagtagatct agatctagga gctcatgctg    6960
gtatattctg aatccgatgt atctgagtta catctatgag ctacttaata aatatatcta    7020
tgagctaaat tcataggct aagcatgaac ctcacctcca agactcgggg ttcctaaatg     7080
gatgagaccc tctttgggaa gtcttgtggg cagtgtctaa ttccactaga aaagttttac    7140
ctacaattta aacttaaacc atgatatttt cttactgctg tttccttttt tcatttttcag   7200 gtggtattac acagacacgt gagtttattg gtcttttatt tatgccctgt ctgaggatgc    7260
agattggtgg gtagatgaga aggaactgat tgagagagat taaccccaag aactgatatc    7320
ttcccagcat tgcattctca actccatttt agaaaggttc caaatagga cttctgtggg     7380 ttttcttta catccatctt acccttccca agtccccatg tccctgcgta aaccctaaag     7440
ccacctctca aaaggttctc tagttccctt caaggttctc tagttccctt cattccacat    7500
atctcctctt ccacaccctc tagccagtag agctcccttc tgacaagcaa gtctaagatc    7560
tagatgacag atgacttcct gcatttgggt ggttcttttg tcactaattt gccttttcta    7620
aaattgtcct ggtttcttct gccaattccc cttcttctc cccagcatat aaagtctcca    7680
tctctggaac cacagtaata ttgacatgcc ctcagtatcc tggatctgaa atactatggc    7740
```

| | |
|---|---|
| aacacaatga taaaaacata ggcggtgatg aggatgataa aaacataggc agtgatgagg | 7800 |
| atcacctgtc actgaaggaa ttttcagaat tggagcaaag tggttattat gtctgctacc | 7860 |
| ccagaggaag caaaccagaa gatgcgaact tttatctcta cctgagggca agaggtaatc | 7920 |
| caggtctcca gaacaggtac caccggctct ttagggagga ccattcaaaa gggcattctc | 7980 |
| agtgattttc cctaacccag ctcacagtgc ccaggcgtct ttgcgcttcc tcccacactc | 8040 |
| aatcctggga ctctctggta ccacacggca tcagtgtttt ctggaatata gattaaacac | 8100 |
| caatatgagg cttctgggta accccagtct gtgcgagatc taaaatagca actccctaag | 8160 |
| agacaggact gggtcatttg caccgcatca cacccaggtt catagcacac caacatgagt | 8220 |
| ttatctaatg cttcctccag agataaattt ttcagaaagg tttgcaaaaa acactcaagg | 8280 |
| ccactatagt aaaatggcat aagctaaggt ataataataa aataataaca atacttaaca | 8340 |
| tttattgagt gcttattaag tctcaagcac tgtctgtacc caacacttat caaggattct | 8400 |
| ttttcatgta atcctctcaa caactatatg ggttaagtat cattttattc ccatgagtaa | 8460 |
| agggatgagg aaacagaggg tttgtgagtt gaaaacacat ttcacgcttc tcacagctag | 8520 |
| tgagtaataa agctgggact caaacccagg gctgtttgac tccagtgcct ctacccacgg | 8580 |
| ccaccactct ttgcttgtca atgttgttct aaacatattg aaggggggc tctgaccgtg | 8640 |
| gcaagcgtgt gagtagtaag gggagaatgg ccttcatgca ctccctcctc acctccagcg | 8700 |
| ccttgtgttt tccttgctta gtgatttccc ctctccccac cccacccccc acagtgtgtg | 8760 |
| agaactgcat ggagatggat | 8780 |

<210> SEQ ID NO 4
<211> LENGTH: 1436
<212> TYPE: DNA
<213> ORGANISM: Mus musculus

<400> SEQUENCE: 4

| | |
|---|---|
| gcgtctggtg ccttcttcag aaatgaagta atgagctggc tgcgtccgcc atcttggtag | 60 |
| agagagcatt ctgagaggat gcggtggaac actttctggg gcatcctgtg cctcagcctc | 120 |
| ctagctgttg gcacttgcca ggacgatgcc gagaacattg aatacaaagt ctccatctca | 180 |
| ggaaccagtg tagagttgac gtgccctcta gacagtgacg agaacttaaa atgggaaaaa | 240 |
| aatggccaag agctgcctca gaagcatgat aagcacctgg tgctccagga tttctcggaa | 300 |
| gtcgaggaca gtggctacta cgtctgctac acaccagcct caaataaaaa cacgtacttg | 360 |
| tacctgaaag ctcgagtgtg tgagtactgt gtggaggtgg acctgacagc agtagccata | 420 |
| atcatcattg ttgacatctg tatcactctg ggcttgctga tggtcattta ttactggagc | 480 |
| aagaatagga aggccaaggc caagcctgtg acccgaggaa ccggtgctgg tagcaggccc | 540 |
| agagggcaaa acaaggagcg gccaccacct gttcccaacc cagactatga gcccatccgc | 600 |
| aaaggccagc gggacctgta ttctggcctg aatcagagag cagtctgaca gataggagag | 660 |
| acatcgcctt ctgtggaccc agatccagcc ctccgagcac cctgctactc cttgttctct | 720 |
| ggacagactg cagactccac agcttgctct tcagcctcct ggtgaacacg tgtcctagaa | 780 |
| ccttgctctc ctgcctcctc tgctagtagc cagtgctggg acattgctga ctcaacagcc | 840 |
| tttgaaagaa tcaggctgct cagattgtct gccagccacc ttgtggggat acttttttca | 900 |
| gccgccctgc tgccagctcc ccgctgcctc accagtgtcc tctctgcctc agttcctttc | 960 |
| ctctcctaat tggccctcat agctaagccc tttcctacag cttctgtttt ttcttttttc | 1020 |
| tttcttttta ggttttcttt cttttctttt ttattccttt ttatttaatc tttttttttt | 1080 |

```
aaacactcca gattttattc ccttcccggc ccatcctccg actgttacac accccatacc    1140
tcctccctgc cccettgtct ctacgagaat gtccccccacc cccatccccc acctgctttc    1200 tggttttgg tttttggttt gttttttttt tttaaactct gtgttttaca ctcttctctg     1260
ggatggattc tgtaatcatt ggcacaggtc ctgccccatt tatagatcct ggcccagccc    1320
ctgccacagg tgcctctcca gatttcccct tagatcctcg gatggtcatc tccatctcca    1380
tgaatacacc agcccctct ctgctaatgc aaaggcaat aaagtgtatt ggctgg          1436
```

<210> SEQ ID NO 5
<211> LENGTH: 189
<212> TYPE: PRT
<213> ORGANISM: Mus musculus

<400> SEQUENCE: 5

```
Met Arg Trp Asn Thr Phe Trp Gly Ile Leu Cys Leu Ser Leu Leu Ala
1               5                   10                  15

Val Gly Thr Cys Gln Asp Asp Ala Glu Asn Ile Glu Tyr Lys Val Ser
            20                  25                  30

Ile Ser Gly Thr Ser Val Glu Leu Thr Cys Pro Leu Asp Ser Asp Glu
        35                  40                  45

Asn Leu Lys Trp Glu Lys Asn Gly Gln Glu Leu Pro Gln Lys His Asp
    50                  55                  60

Lys His Leu Val Leu Gln Asp Phe Ser Glu Val Asp Ser Gly Tyr
65                  70                  75                  80

Tyr Val Cys Tyr Thr Pro Ala Ser Asn Lys Asn Thr Tyr Leu Tyr Leu
                85                  90                  95

Lys Ala Arg Val Cys Glu Tyr Cys Val Glu Val Asp Leu Thr Ala Val
            100                 105                 110

Ala Ile Ile Ile Ile Val Asp Ile Cys Ile Thr Leu Gly Leu Leu Met
        115                 120                 125

Val Ile Tyr Tyr Trp Ser Lys Asn Arg Lys Ala Lys Ala Lys Pro Val
    130                 135                 140

Thr Arg Gly Thr Gly Ala Gly Ser Arg Pro Arg Gly Gln Asn Lys Glu
145                 150                 155                 160

Arg Pro Pro Pro Val Pro Asn Pro Asp Tyr Glu Pro Ile Arg Lys Gly
                165                 170                 175

Gln Arg Asp Leu Tyr Ser Gly Leu Asn Gln Arg Ala Val
            180                 185
```

<210> SEQ ID NO 6
<211> LENGTH: 1534
<212> TYPE: DNA
<213> ORGANISM: Homo sapiens

<400> SEQUENCE: 6

```
tattgtcaga gtcctcttgt ttggccttct aggaaggctg tgggaccccag ctttcttcaa    60 ccagtccagg tggaggcctc tgccttgaac gtttccaagt gaggtaaaac ccgcaggccc    120
agaggcctct ctacttcctg tgtggggttc agaaaccctc ctcccctccc agcctcaggt    180
gcctgcttca gaaaatgaag tagtaagtct gctggcctcc gccatcttag taaagtaaca    240
gtcccatgaa acaaagatgc agtcgggcac tcactggaga gttctgggcc tctgcctctt    300
atcagttggc gtttgggggc aagatggtaa tgaagaaatg ggtggtatta cacagacacc    360
atataaagtc tccatctctg gaaccacagt aatattgaca tgccctcagt atcctggatc    420
```

```
tgaaatacta tggcaacaca atgataaaaa cataggcggt gatgaggatg ataaaaacat    480
aggcagtgat gaggatcacc tgtcactgaa ggaattttca gaattggagc aaagtggtta    540
ttatgtctgc taccccagag gaagcaaacc agaagatgcg aacttttatc tctacctgag    600
ggcaagagtg tgtgagaact gcatggagat ggatgtgatg tcggtggcca caattgtcat    660
agtggacatc tgcatcactg ggggcttgct gctgctggtt tactactgga gcaagaatag    720
aaaggccaag gccaagcctg tgacacgagg agcgggtgct ggcggcaggc aaagggggaca   780
aaacaaggag aggccaccac ctgttcccaa cccagactat gagcccatcc ggaaaggcca    840
gcgggacctg tattctggcc tgaatcagag acgcatctga ccctctggag aacactgcct    900
cccgctggcc caggtctcct ctccagtccc cctgcgactc cctgtttcct gggctagtct    960
tggaccccac gagagagaat cgttcctcag cctcatggtg aactcgcgcc ctccagcctg   1020
atcccccgct ccctcctccc tgccttctct gctggtaccc agtcctaaaa tattgctgct   1080
tcctcttcct tgaagcatc atcagtagtc acaccctcac agctggcctg ccctcttgcc    1140
aggatattta tttgtgctat tcactccctt cccttttggat gtaacttctc cgttcagttc   1200
cctcctttc ttgcatgtaa gttgtccccc atcccaaagt attccatcta cttttctatc    1260
gccgtccct tttgcagccc tctctgggga tggactgggg aaatgttgac agaggccctg    1320
ccccgttcac agatcctggc cctgagccag ccctgtgctc ctccctcccc caacactccc   1380
taccaacccc ctaatcccct actccctcca ccccccctcc actgtaggcc actggatggt   1440
catttgcatc tccgtaaatg tgctctgctc ctcagctgag agagaaaaaa ataaactgta   1500
tttggctgca agaaaaaaaa aaaaaaaaaa aaaa                                1534

<210> SEQ ID NO 7
<211> LENGTH: 207
<212> TYPE: PRT
<213> ORGANISM: Homo sapiens

<400> SEQUENCE: 7

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175
```

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 8
<211> LENGTH: 624
<212> TYPE: DNA
<213> ORGANISM: Artificial Sequence
<220> FEATURE:
<223> OTHER INFORMATION: Homo sapiens and Mus musculus

<400> SEQUENCE: 8

| | | | | | |
|---|---|---|---|---|---|
| atgcagtcgg | gcactcactg | agagttctg | ggcctctgcc | tcttatcagt | tggcgtttgg | 60 |
| gggcaagatg | gtaatgaaga | aatgggtggt | attacacaga | caccatataa | agtctccatc | 120 |
| tctggaacca | cagtaatatt | gacatgccct | cagtatcctg | gatctgaaat | actatggcaa | 180 |
| cacaatgata | aaaacatagg | cggtgatgag | gatgataaaa | acataggcag | tgatgaggat | 240 |
| cacctgtcac | tgaaggaatt | ttcagaattg | agcaaagtg | gttattatgt | ctgctacccc | 300 |
| agaggaagca | aaccagaaga | tgcgaacttt | tatctctacc | tgagggcaag | agtgtgtgag | 360 |
| aactgcatgg | agatggatct | gacagcagta | gccataatca | tcattgttga | catctgtatc | 420 |
| actctgggct | tgctgatggt | catttattac | tggagcaaga | ataggaaggc | caaggccaag | 480 |
| cctgtgaccc | gaggaaccgg | tgctggtagc | aggcccagag | gcaaaacaa | ggagcggcca | 540 |
| ccacctgttc | ccaacccaga | ctatgagccc | atccgcaaag | ccagcggga | cctgtattct | 600 |
| ggcctgaatc | agagagcagt | ctga | | | | 624 |

<210> SEQ ID NO 9
<211> LENGTH: 1490
<212> TYPE: DNA
<213> ORGANISM: Artificial Sequence
<220> FEATURE:
<223> OTHER INFORMATION: Homo sapiens and Mus musculus

<400> SEQUENCE: 9

| | | | | | |
|---|---|---|---|---|---|
| gcgtctggtg | ccttcttcag | aaatgaagta | atgagctggc | tgcgtccgcc | atcttggtag | 60 |
| agagagcatt | ctgagaggat | gcagtcgggc | actcactgga | gagttctggg | cctctgcctc | 120 |
| ttatcagttg | gcgtttgggg | gcaagatggt | aatgaagaaa | tgggtggtat | tacacagaca | 180 |
| ccatataaag | tctccatctc | tggaaccaca | gtaatattga | catgccctca | gtatcctgga | 240 |
| tctgaaatac | tatggcaaca | caatgataaa | aacataggcg | gtgatgagga | tgataaaaac | 300 |
| ataggcagtg | atgaggatca | cctgtcactg | aaggaatttt | cagaattgga | gcaaagtggt | 360 |
| tattatgtct | gctaccccag | aggaagcaaa | ccagaagatg | cgaacttta | tctctacctg | 420 |
| agggcaagag | tgtgtgagaa | ctgcatggag | atggatctga | cagcagtagc | cataatcatc | 480 |
| attgttgaca | tctgtatcac | tctgggcttg | ctgatggtca | tttattactg | gagcaagaat | 540 |
| aggaaggcca | aggccaagcc | tgtgacccga | ggaaccggtg | ctggtagcag | gcccagaggg | 600 |
| caaaacaagg | agcggccacc | acctgttccc | aacccagact | atgagcccat | ccgcaaaggc | 660 |
| cagcgggacc | tgtattctgg | cctgaatcag | agagcagtct | gacagatagg | agagacatcg | 720 |
| ccttctgtgg | acccagatcc | agccctccga | gcaccctgct | actccttgtt | ctctggacag | 780 |
| actgcagact | ccacagcttg | ctcttcagcc | tcctggtgaa | cacgtgtcct | agaaccttgc | 840 |
| tctcctgcct | cctctgctag | tagccagtgc | tgggacattg | ctgactcaac | agcctttgaa | 900 |
| agaatcaggc | tgctcagatt | gtctgccagc | caccttgtgg | ggatactttt | ttcagccgcc | 960 |

-continued

```
ctgctgccag ctccccgctg cctcaccagt gtcctctctg cctcagttcc tttcctctcc    1020
taattggccc tcatagctaa gcccttcct acagctttct gttttttctt tttctttctt     1080
tttaggtttt ctttctttc tttttattc cttttatt aatctttttt ttttaaacac       1140
tccagatttt attcccttcc cggcccatcc tccgactgtt acacacccca tacctcctcc    1200
ctgccccctt gtctctacga gaatgtcccc caccccatc ccccacctgc tttctggttt    1260 ttggttttg gtttgttttt ttttttaaa ctctgtgttt tacactcttc tctgggatgg     1320
attctgtaat cattggcaca ggtcctgccc catttataga tcctggccca gccctgcca    1380 caggtgcctc tccagatttc ccttagatc ctcggatggt catctccatc tccatgaata    1440
caccagcccc ctctctgcta atgcaaaagg caataaagtg tattggctgg              1490
```

<210> SEQ ID NO 10
<211> LENGTH: 207
<212> TYPE: PRT
<213> ORGANISM: Artificial Sequence
<220> FEATURE:
<223> OTHER INFORMATION: Homo sapiens and Mus musculus

<400> SEQUENCE: 10

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Leu Thr
        115                 120                 125

Ala Val Ala Ile Ile Ile Val Asp Ile Cys Ile Thr Leu Gly Leu
    130                 135                 140

Leu Met Val Ile Tyr Tyr Trp Ser Lys Asn Arg Lys Ala Lys Ala Lys
145                 150                 155                 160

Pro Val Thr Arg Gly Thr Gly Ala Gly Ser Arg Pro Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Ala Val
        195                 200                 205
```

<210> SEQ ID NO 11
<211> LENGTH: 34
<212> TYPE: DNA
<213> ORGANISM: Artificial Sequence
<220> FEATURE:
<223> OTHER INFORMATION: PCR primer

<400> SEQUENCE: 11

```
cgatctcgag agtactgagt gcttcaacgt cttc                               34
```

<210> SEQ ID NO 12
<211> LENGTH: 37
<212> TYPE: DNA
<213> ORGANISM: Artificial Sequence
<220> FEATURE:
<223> OTHER INFORMATION: PCR primer

<400> SEQUENCE: 12
gtgcccgact gcatcctctc agaatgctct ctctacc                              37

<210> SEQ ID NO 13
<211> LENGTH: 33
<212> TYPE: DNA
<213> ORGANISM: Artificial Sequence
<220> FEATURE:
<223> OTHER INFORMATION: PCR primer

<400> SEQUENCE: 13
gcattctgag aggatgcagt cgggcactca ctg                                  33

<210> SEQ ID NO 14
<211> LENGTH: 39
<212> TYPE: DNA
<213> ORGANISM: Artificial Sequence
<220> FEATURE:
<223> OTHER INFORMATION: PCR primer

<400> SEQUENCE: 14
gcttatgcca tttaaattac gaggcgtttt atggtctca                            39

<210> SEQ ID NO 15
<211> LENGTH: 39
<212> TYPE: DNA
<213> ORGANISM: Artificial Sequence
<220> FEATURE:
<223> OTHER INFORMATION: PCR primer

<400> SEQUENCE: 15
gcctcgtaat ttaaatggca taagctaagg tataataat                            39

<210> SEQ ID NO 16
<211> LENGTH: 34
<212> TYPE: DNA
<213> ORGANISM: Artificial Sequence
<220> FEATURE:
<223> OTHER INFORMATION: PCR primer

<400> SEQUENCE: 16
ctactgctgt cagatccatc tccatgcagt tctc                                 34

<210> SEQ ID NO 17
<211> LENGTH: 35
<212> TYPE: DNA
<213> ORGANISM: Artificial Sequence
<220> FEATURE:
<223> OTHER INFORMATION: PCR primer

<400> SEQUENCE: 17
tggagatgga tctgacagca gtagccataa tcatc                                35

<210> SEQ ID NO 18
<211> LENGTH: 32
<212> TYPE: DNA
<213> ORGANISM: Artificial Sequence
<220> FEATURE:

```
<223> OTHER INFORMATION: PCR primer

<400> SEQUENCE: 18
cgataagctt cctggcagct gatggaaacc ag                                    32

<210> SEQ ID NO 19
<211> LENGTH: 39
<212> TYPE: DNA
<213> ORGANISM: Artificial Sequence
<220> FEATURE:
<223> OTHER INFORMATION: PCR primer

<400> SEQUENCE: 19
cgatggatcc agaattcaag tgctgctgaa cagagccag                             39

<210> SEQ ID NO 20
<211> LENGTH: 42
<212> TYPE: DNA
<213> ORGANISM: Artificial Sequence
<220> FEATURE:
<223> OTHER INFORMATION: PCR primer

<400> SEQUENCE: 20
cgatgcggcc gcagtactca ttttaacata agcatcgatg cc                         42

<210> SEQ ID NO 21
<211> LENGTH: 44
<212> TYPE: DNA
<213> ORGANISM: Artificial Sequence
<220> FEATURE:
<223> OTHER INFORMATION: PCR primer

<400> SEQUENCE: 21
gctggtaccg gcgcgcctcg agctcagatg ttcctgcaat catg                       44

<210> SEQ ID NO 22
<211> LENGTH: 36
<212> TYPE: DNA
<213> ORGANISM: Artificial Sequence
<220> FEATURE:
<223> OTHER INFORMATION: PCR primer

<400> SEQUENCE: 22
gctgaatgct gatatcatgt gaggccttta aatgtg                                36

<210> SEQ ID NO 23
<211> LENGTH: 35
<212> TYPE: DNA
<213> ORGANISM: Artificial Sequence
<220> FEATURE:
<223> OTHER INFORMATION: PCR primer

<400> SEQUENCE: 23
aggcctcaca tgatatcagc attcagcaag tccag                                 35

<210> SEQ ID NO 24
<211> LENGTH: 48
<212> TYPE: DNA
<213> ORGANISM: Artificial Sequence
<220> FEATURE:
<223> OTHER INFORMATION: PCR primer

<400> SEQUENCE: 24
tcctcttcag acctggcggc cgcacaagaa atgtttcaga tgcctttc                   48
```

<210> SEQ ID NO 25
<211> LENGTH: 1862
<212> TYPE: DNA
<213> ORGANISM: Artificial Sequence
<220> FEATURE:
<223> OTHER INFORMATION: Synthesized sequence

<400> SEQUENCE: 25

```
gaattccgaa gttcctattc tctagaaagt ataggaactt caggtctgaa gaggagttta      60
cgtccagcca agctagcttg gctgcaggtc gtcgaaattc taccgggtag gggaggcgct     120
tttcccaagg cagtctggag catgcgcttt agcagccccg ctgggcactt ggcgctacac     180
aagtggcctc tggcctcgca cacattccac atccaccggt aggcgccaac cggctccgtt     240
ctttggtggc cccttcgcgc caccttctac tcctcccta gtcaggaagt tccccccgc      300
cccgcagctc gcgtcgtgca ggacgtgaca aatggaagta gcacgtctca ctagtctcgt     360
gcagatggac agcaccgctg agcaatggaa gcgggtaggc ctttgggca gcggccaata     420
gcagctttgc tccttcgctt tctgggctca gaggctggga aggggtgggt ccggggcgg      480
gctcagggc gggctcaggg gcggggcggg cgcccgaagg tcctccggag gcccggcatt     540
ctgcacgctt caaaagcgca cgtctgccgc gctgttctcc tcttcctcat ctccgggcct     600
ttcgacctgc agcctgttga caattaatca tcggcatagt atatcggcat agtataatac     660
gacaaggtga ggaactaaac catgggatcg ccattgaac aagatggatt gcacgcaggt     720
tctccggccg cttgggtgga gaggctattc ggctatgact gggcacaaca gacaatcggc     780
tgctctgatg ccgccgtgtt ccggctgtca gcgcagggc gcccggttct ttttgtcaag     840
accgacctgt ccggtgccct gaatgaactg caggacgagg cagcgcggct atcgtggctg     900
gccacgacgg gcgttccttg cgcagctgtg ctcgacgttg tcactgaagc gggaagggac     960
tggctgctat tgggcgaagt gccggggcag gatctcctgt catctcacct tgctcctgcc    1020
gagaaagtat ccatcatggc tgatgcaatg cggcggctgc atacgcttga tccggctacc    1080
tgcccattcg accaccaagc gaaacatcgc atcgagcgag cacgtactcg gatggaagcc    1140
ggtcttgtcg atcaggatga tctggacgaa gagcatcagg ggctcgcgcc agccgaactg    1200
ttcgccaggc tcaaggcgcg catgcccgac ggcgatgatc tcgtcgtgac ccatggcgat    1260
gcctgcttgc cgaatatcat ggtgaaaat ggccgctttt ctggattcat cgactgtggc    1320
cggctgggtg tggcggaccg ctatcaggac atagcgttgg ctacccgtga tattgctgaa    1380
gagcttggcg gcgaatgggc tgaccgcttc ctcgtgcttt acggtatcgc cgctcccgat    1440
tcgcagcgca tcgccttcta tcgccttctt gacgagttct tctgagggga tcaattctct    1500
agagctcgct gatcagcctc gactgtgcct tctagttgcc agccatctgt tgtttgcccc    1560
tcccccgtgc cttccttgac cctggaaggt gccactccca ctgtcctttc ctaataaaat    1620
gaggaaattg catcgcattg tctgagtagg tgtcattcta ttctgggggg tggggtgggg    1680
caggacagca aggggagga ttgggaagac aatagcaggc atgctgggga tgcggtgggc    1740
tctatggctt ctgaggcgga aagaaccagc tggggctcga ctagagcttg cggaacccttt    1800
cgaagttcct attctctaga aagtatagga acttcatcag tcaggtacat aatggtggat    1860
cc                                                                    1862
```

<210> SEQ ID NO 26
<211> LENGTH: 22
<212> TYPE: DNA
<213> ORGANISM: Artificial Sequence
<220> FEATURE:

<223> OTHER INFORMATION: PCR primer

<400> SEQUENCE: 26
atggcaacca atgatccagg gt                                              22

<210> SEQ ID NO 27
<211> LENGTH: 20
<212> TYPE: DNA
<213> ORGANISM: Artificial Sequence
<220> FEATURE:
<223> OTHER INFORMATION: PCR primer

<400> SEQUENCE: 27
ctgagtcccc agcccttgtc                                                 20

<210> SEQ ID NO 28
<211> LENGTH: 21
<212> TYPE: DNA
<213> ORGANISM: Artificial Sequence
<220> FEATURE:
<223> OTHER INFORMATION: PCR primer

<400> SEQUENCE: 28
atgaggctcc ttggtgccac t                                               21

<210> SEQ ID NO 29
<211> LENGTH: 26
<212> TYPE: DNA
<213> ORGANISM: Artificial Sequence
<220> FEATURE:
<223> OTHER INFORMATION: PCR primer

<400> SEQUENCE: 29
catgtatcgc aacatcaaag gtgcag                                          26

<210> SEQ ID NO 30
<211> LENGTH: 25
<212> TYPE: DNA
<213> ORGANISM: Artificial Sequence
<220> FEATURE:
<223> OTHER INFORMATION: PCR primer

<400> SEQUENCE: 30
catcctgctg tataaccact actgc                                           25

<210> SEQ ID NO 31
<211> LENGTH: 25
<212> TYPE: DNA
<213> ORGANISM: Artificial Sequence
<220> FEATURE:
<223> OTHER INFORMATION: PCR primer

<400> SEQUENCE: 31
gacaagcgtt agtaggcaca tatac                                           25

<210> SEQ ID NO 32
<211> LENGTH: 24
<212> TYPE: DNA
<213> ORGANISM: Artificial Sequence
<220> FEATURE:
<223> OTHER INFORMATION: PCR primer

<400> SEQUENCE: 32
gctccaattt cccacaacat tagt                                            24

<210> SEQ ID NO 33
<211> LENGTH: 39
<212> TYPE: DNA
<213> ORGANISM: Artificial Sequence
<220> FEATURE:
<223> OTHER INFORMATION: PCR primer

<400> SEQUENCE: 33
gtttggggct atttaaatta cgaggcgttt tatggtctc                    39

<210> SEQ ID NO 34
<211> LENGTH: 36
<212> TYPE: DNA
<213> ORGANISM: Artificial Sequence
<220> FEATURE:
<223> OTHER INFORMATION: PCR primer

<400> SEQUENCE: 34
cgcctcgtaa tttaaatagc cccaaacttt gctcac                       36

<210> SEQ ID NO 35
<211> LENGTH: 35
<212> TYPE: DNA
<213> ORGANISM: Artificial Sequence
<220> FEATURE:
<223> OTHER INFORMATION: PCR primer

<400> SEQUENCE: 35
ctctcctatc tgtcagatgc gtctctgatt caggc                        35

<210> SEQ ID NO 36
<211> LENGTH: 32
<212> TYPE: DNA
<213> ORGANISM: Artificial Sequence
<220> FEATURE:
<223> OTHER INFORMATION: PCR primer

<400> SEQUENCE: 36
cgcatctgac agataggaga gacatcgcct tc                           32

<210> SEQ ID NO 37
<211> LENGTH: 5246
<212> TYPE: DNA
<213> ORGANISM: Artificial Sequence
<220> FEATURE:
<223> OTHER INFORMATION: Mus musculus

<400> SEQUENCE: 37
ctcagatgtt cctgcaatca tgcctttgct ctgccaccat ggactctggc tctaaaactg      60
tgatccccag gttaagggct ttcttttata aattgccttc actgtggtgt tatcacagtg     120
ataggaaagt gactgaaaca gacagtaaat gctgagatag gacagttgtt tatgccagag     180
ctgggccata gtaagaaaaa cctggacccc tgaaactgat gggatgacat gggatgggat     240
ggcatgagac aggataacat gggatggggt agaagggatg agaggagaaa gggtaggatg     300
agagaggaag ggagaggagg ggaagaatgg gaagggaggg gatggaatag gatgagagag     360
gagaaagagg aggagagggg aggggaggga ttgaatgaga agggatggga tgcgagtctt     420
gattttccag atcgtccttg aaccattagg cctacagaat tggaccacac atttaaaggc     480
ctcacatgat gtgtcctata aggcaccact aaccccattc ccctcctggc catcaaacct     540
gttactagag ccaattctca aggtgactca actggttaag tactagagag gttaatgtgc     600
caagtatcgc aggctcaggc tcgtgctttg aaagctcagt ccccagttaa tgataatgct     660

```
ttaggtggct gtggaattgt taggggggtgt ggctaagctg tcagatccag gaagtcacaa    720
ggttggaggg gtgcagcaat aatccactgt gagatagaat gaatgaactc tatgtgggag    780
atgaatgcca ctgctactgg agttcatacc caagactctt aagctgtggt ggtttgtata    840
tgctcagccc agggactggc actattagaa ggtgtgaccc tgttgagtag gtgtgtcact    900
gtgggtacgg gctttaagac cctcatccta gctgcctgga agccagtctt ccactagcag    960
ccttcagatg aagaggtagg actctcagct cctttggcac catgcctgcc tggatactga   1020
catgcccttg tcttaatgat aatggactaa acctctgaac ctgtaagtca gccccaatta   1080
aatgttgtcc ttataagagt tgccttggag gctggaaaga tggctcagtg gttaagagta   1140
ttgactgctc ttccaaaggt cctgagttca attcccagca accacatgat ggctcacaat   1200
catctgtaat gggtctgat gccctcttct ggtgtgtctg aagacaccta cagtgtactc   1260
atataaataa aataaatctt aaaaaaaac aaaacaaaa acaaaaaagt tgccttggtc   1320
atggtatctg ttcacagcag taaaacccta actaagacag aagtcatcta tcacttcttc   1380
accctcagat cagactgtgg ctggctacat agcaagctac tccctaagca acggctggaa   1440
gaggagggtg aagctgagct tgttgtcaa atctcacctg agcatgtgag tgaaagtcaa   1500
atatgaaaag ctgcaactgt gcagctccac tcatggctga agacagccat aagaggagac   1560
cctcccactg gcagggacct ggcattgtac ctgatcatct actttatatg ggaagggaaa   1620
tggcctaacg tcctcagaca caccagaaga gggcatcgga tcccattaca gaggttgtga   1680
gccaccatgt ggttcctggg aattgaactc aggacctctg gaagagcagc cagtgctttt   1740
aaccactgag ccatctctcc aggcccccac ccccaccacg agacctcact cctaactaag   1800
gagctattga cagttagtga ccactaagag aggaagaaca cttttctttg ggggtgcctg   1860
cttgtaggtt ggccttgccc cagtggatga ccttacactc actcacttcc acactcatgc   1920
accctgatt aggatttact ggactcagag gactagtaat aataattggg gaagacaatt   1980
taggtggata aaatctaaat acattatatt catgttcaaa atttcaaag acaaataaa   2040
aagtttaaaa gaaaacttct ggagggctgg agagatggct gactgctctt ccagaggtcc   2100
tgagttcaat tccagcaat cacaaccacc tgtaatggga tctgatgccc tcttctgttg   2160
tgtctgaaga cagcgacggt gtactcatat acataaaata aataactaaa tctttaaaca   2220
aagaaaagga aaggaaagtt ctggttagag agatgcctca gaggttaaga gcactcgatg   2280
ctcatataga agccccgagt tcagatccta gcacccacct ggcagctaac agcagtctgt   2340
aactccatct tccaggacct gatgccctgt tctggcttcc tcaggtactg cacacacatg   2400
atatacatac aatgcatgct ggcaaagcac tcgtgcgtat aaaacatctt ttttataaaa   2460
aggggtccat caatatcctg aagggactgt ttgaggatga gggaagcagg tgacggggca   2520
ctgtcacctg aactggatct gcgtgacact gcctaggacc cccagctgat agggttgctg   2580
cccccctgaga gtggcaaaca gccagaccat aggtatcacc ctcgggagag cctactgcct   2640
cacccaagtc cacaccacct ccggggacca gcttccatcc aactactggg taacgtgccc   2700
cttgccatgc cataactcaa gaaatcagag acagcgcttt actgctctcc tccctcctgg   2760
cggctctcat gctcttcctg acctctcttc ctcaatgtct ttaaggtttt tagaaggaaa   2820
aagtttaatt atggaagtga tacatcattg cttctcagac gtttggctaa catcaagtgt   2880
ggaagtaaga ccgtgcatgt attaaaacca atgaagagca taggagaggt gtataataac   2940
accacgcccc actcatccca ccactatgcc ttttctcagg ggcacaacca cctcaacgga   3000
cccccttcctc tgggcttatc ttcacatccc acaaagtgca cagacatcct tgagttccc   3060
```

```
tgggaaacaa accttgaggt ggagatttgt gtgcaggtgg ctcgtgggaa tgcaggacac    3120
ctgcaaagga gagagggaag ccacaaggca gacagagaaa gtcaacttca gggagcgact    3180
tcagggagcg gcagctcaga ggcctctgct tgggcctctg tgctcatgag ctcactgcag    3240
ctctggttac catgcagcat ttcagcaggc agcaggtaac tgcactcaga gggtgggggg    3300
cgggtgaggg gggttgggga ggggagagat gtacggggga tgtctgaggg cagtgaaagg    3360
gagaaatcaa ggtggatatg atcaagatac attacataca tgtatggaat tgtcggagaa    3420
taaataaatc tttttgaaa aaggggaga gagcgccaga gagtgagaca gcaaggcaga    3480
aagcaaaccc caactcaaaa acaaggcgga aaggggactc agactccaaa ctaaggtaga    3540 aaggggatc gagaaagagc gcttagtatc catctctggc ctccacaagc acctcacacg    3600
tctgcacact caaactccat acatacatga aaagattttg taatttccat taattaattt    3660
atttactcat tttacatccc aatctcagcc ccctcctcc aagccccccc tccaagtccc    3720 cgccctcag atagccgctc ccccaccccc tccttccct tcccatctga aagagggag    3780 gtccctctgg gcactgagtc tgatactatc ccttatctgg agatgtgggt gggcaaaaag    3840
aatgtaagag tagaaactag ggagaagggc tgtgaagcac tgccttctag tagctgtggc    3900
agccagcagt ggatccacat gcaactgggc ttatcaacag tcaatcatgc attggggcgg    3960
gacttctggg gctctaagcc tttctactga actataggtt atagatggat tcagaaagaa    4020
aggcagccgt tttcttcagt cctgtaccca ctgaggagct cttcaggctc cttcagtagt    4080
tagttccaaa tccactgtca cacagctaac tctcgttaaa cccagtagat atatcaagaa    4140
gcggagccag agagatacct caacagataa agttgtttgt ggttaaaaac ctaaagacct    4200
gaattgaaac ctgggactca catgttagag agaatccctc aagctaccct cgacttccac    4260
acatgctgtg gcaagtctat gcccacacat atacacatat aataaatagg taaataaata    4320
acgtaaaact ttttttcgt aaaacttttt aataaaagac ttgtcgagaa agggagatta    4380
atcatcagaa agtgtgttac aattgtatga aattatcaaa gagctaagtc aataagcgtt    4440
ttttacaaag aaaaagattg ttgcttataa ctcaggaagt acttatgcta gattttaaat    4500
aataatgcta aaagctaccc tagtgggtgc atgagtaaag cccctagcat agtgtcagta    4560
caaagacagg agctatgtga ctctctcatt gtccagcaac tgcccagcat gtgcaatcaa    4620
aggccaggac ggctacatgc taaaaatcct gtctcaaaga aagaaagaaa agaaaagcaa    4680
gcccctcgaa gattattaat gagacggctc cactccatcc tgctgctcag acccaagggc    4740
accataacag aaggcagata ctgagtgctt caacgtcttc ctgcctccgc tggaggggtt    4800
atgcataagg aaggctccct cagtgtggag gtgctttgca cagggcacaa gtaggtgttt    4860
ttcacagcac tctcggggc ttgctagagc ccccttgtt catccttatg ggaaggctgt    4920
gaggcgcgga tttcctcagt taaccaaggc ggaggcttct gcctcaaaca tttccaagtg    4980
acgtggagca ggcgggccct gagtcccctc tacacttcct gtgtggggtt cagacacctg    5040 cctccctgt ctgcgtctgg tgccttcttc agaaatggta agtctctcct tgtgaagtgc    5100 ccccactct ccttcatcct actatggcaa ccaatgatcc agggtctttg catgcagcca    5160
ctgtgttgaa aacctcatct gtttcttttt cagaagtaat gagctggctg cgtccgccat    5220
cttggtagag agagcattct gagagg                                         5246
```

<210> SEQ ID NO 38
<211> LENGTH: 3547
<212> TYPE: DNA

<213> ORGANISM: Artificial Sequence
<220> FEATURE:
<223> OTHER INFORMATION: Mus musculus

<400> SEQUENCE: 38

```
aagtgctgct gaacagagcc agggaagacg agaaaagccg tgcgtgcgtg cgtgcgtgca      60
tgcatgcggt tccctcctgc cctggaggca gctgtctgaa gccccaagca gtagtggtta     120
tacagcagga tgtgggctgt gctgggagtg aggatgagag aggtgtggtg gtagccacgg     180
accagacact ggaggctatc gatgagagaa tgtggtcctt ggtctcccac atactctgct     240
tgcaggagag aggaacccag agcccaagca agctatccta ggccagctca agccatcgga     300
ctctcttctc cacctttctg ccctcagaca catccctgct gacttaaggg ctatttgtta     360
tgtgacttta gcttctgtgc ctagcagcgg tccacacact gtccatactc tgccttggat     420
ttgtaactac agttcctgct agttggtctc cactaaactg tcacctttc ctctctaggc      480
atcgatgctt atgttaaaat gagtcttgat gattttgcct atcaccaaac actaataagc     540
aggtggcaga ttttgtcctg catatatttg atgtgtccag tcaaggacat tcgtagctca     600
acatgataaa aagcattaac atttggtgtt tactgagaat ttaccatgct ccagaagttg     660
ttatagcccct atatgtgctg tctcatttaa tccttataga gacgccacaa atatatgttg    720
tcatcttcta tatagtgggc tcagagaggt agcatcattt atccatgtga agtgaaatgc     780
agggctacaa ttagcagcta gagatgtcta attctggggc actttttttt ttttttttgg    840
atacagagtc tcactatgta gctctggctg tcctagaact atgtatgtat gaactaagca     900
tgtagactag aaactatgta gaccagactg tcctcaaact cacagagatc ctcctgcctg     960
tgcctctgct tcccgagtgc caggattaaa agtgtgcact agtaatgctc tgcttctaac    1020
tccagcactc tggcacctac ccactatgac cgagaccatg gcaatgttct tcttcctacc    1080
atatgcctct ggaaaaaatg gaggagttgg agatggagca gaaacctaga gtctgttttc    1140
tatatgggtc ggaggcagga tacaatagga tgaaggcaga tgccgtgtca aggaaagtga    1200
gggtcatgca aaacacagct cttactccaa atagaatagc agttagttta ttctggagcc    1260
agcaagatgg cttagcaggt gacagtgctt accaccaagc ctgaagaccc gagtttgatt    1320
cccagaacct acctggtaga agaaaaccaa cttttcataaa ttatcctctg actgctaacc    1380
ccaccaggct agaagagcac taccacaatt tatgagccaa atttgaagca agcttttac     1440
tggccaagtc tatggatact ggccagatcc atacgcacta tctatcccca gagctccagc    1500
cctttataag gcaggggcta taaaggcaaa gcccataaga ctaccgactt cttcccacct    1560
tcatctagtc agggacaagc atacaccctg ccacactttc tgcctgtgaa cctgctggca    1620
atgggtaagc aagcacatcc tgtgcagctg gggcaaccca gcttctttat agaagcaaaa    1680
actcccggct tgttatcttc catgatcaac agccccagc atcccaggaa gttggctgtt     1740
cttgagcaag tggggcttac aggttagagg catttgtttt aatagttaga tctcttaagc    1800
acagtaactt atacttagac ataatgttag cctcttgcgc gcgccggact ggccagcagt    1860
aacaacgctg caacaggatc cttctgcaca tgtttattgg gagagcttga ttgtagaggc    1920
gaagagaccc cgagcccaga actggtgctg cttatatagg cctaggagat gcgtgtctca    1980
caccccggatt ggctatgcac tacgcctcat ttgcatgttc ctcatctgat ggctactct    2040
ctctctctct gtacctcaca gagcctcatt atcatacctc atttgcatgt ctcacatctg    2100
attggttata ttctcaaagc ttcattatca tgcccgggcc aggcagtgtc tttgcaaaaa    2160
actttactgc atatgtacac attggttgtt tgtccaaact tatgcgtggt ggccagcagt    2220
```

```
agtcagcgcc actctgcaac ggcacatgtg gcttcccaca ttagccatca tatttctttc    2280
ttgagctgtg tatcctgagt caaatccttg actctaaagt gggtagcggc tcaaattaag    2340
atctaataac catcagctta atggcaccca gacagcaatt tacatatata gttaagatat    2400
taatgatgca aggttattag taactagcag aaacagaagg gcaaaggcct tgtgatggct    2460
gacagcagaa ctactaccta agtggagccc aaaaatgaga atgggagcca gtcatttgtc    2520
tcatcttggg gcctgttttt ctgtaggttt gggtttgctt tgttttgttt tgttttgttt    2580
tggaggggtt gtttgttttt ttagtacatt cagactatct cttatgattt cctgagtggt    2640
ttgcaaagaa gcaacaattt ttttaaacca tacaataacc tcattttaca tagagcaggt    2700
cgagtgtcct atcatgttct atcatatttc agctaataaa tctacttgtt aatagatctg    2760
ggtctatttg gctttagcag gtacctatcc tcatatgtca ataggctcta taggtgccta    2820
tttgtcctat ataccgtgga gtttcctttt aatctaacct tccagccttt tgtagagggt    2880
aaagggtaat gtactctctt ctttaactac ttcctgtgga aattaggaca tcactgacag    2940
ggctcaggaa ggctggaatg ctagtcaaag gccaggaggg gattcagcag aagcattggg    3000
ttagctggcc cagctgaaga gacagggagc aactatatct gctggactgt tttgtccaca    3060
tcagcattca gcaagtccag ggcttttagt cacttggagc aggttgtgta gtccacagct    3120
gattcctgga tggtgtttgt cagccaagtg gaaattcagc tgggacaggt atagaccacg    3180
gacagaagtt taccagtgtt tgtaatttgt gcttaaaatc cacgttgtag aaagggcagc    3240
tggcaggtgt ctgcaaaaca tctggagtgg actcatgcct ttgagtcata gagaaagctt    3300
tcacttaaaa agcttgaaca ttcttttcct gtccagtggt ctaggtatag tgatgcgaaa    3360
tacctttaaa tctacactta gaagacaacc aaaggaattt aaaaccttga gctcatggct    3420
gataatggca gtcagcgctt tgcagctta tcagaactcc actgatgaag gttaaaactc    3480
tgaacgtttg gaaccttagc atgatgacaa catagcaaga aggaaaggca tctgaaacat    3540
ttcttgt                                                             3547

<210> SEQ ID NO 39
<211> LENGTH: 10590
<212> TYPE: DNA
<213> ORGANISM: Artificial Sequence
<220> FEATURE:
<223> OTHER INFORMATION: Homo sapiens

<400> SEQUENCE: 39
atgcagtcgg gcactcactg gagagttctg ggcctctgcc tcttatcagg tgagtaggat      60
ggagtggaaa gggtggtgtg tctccagacc gctggaaggc ttacagcctt acctggcact     120
gcctagtggc accaaggagc ctcatttacc agatgtaagg aactgtttgt gctatgttag     180
ggtgagggat tagagctggg gactaaagaa aaagataggc cacgggtgcc tgggagagcg     240
ttcggggagc aggcaaagaa gagcagttgg ggtgatcata gctattgtga gcagagaggt     300
ctcgctacct ctaagtacga gctcattcca acttacccag ccctccagaa ctaacccaaa     360
agagactgga agagcgaagc tccactcctt gttttgaaga gaccagatac ttgcgtccaa     420
actctgcaca gggcatatat agcaattcac tatctttgag accataaaac gcctcgtaat     480
ttttagtcct tttcaagtga ccaacaactt tcagtttatt tcattttttt gaagcaagat     540
ggattatgaa ttgataaata accaagagca tttctgtatc tcatatgaga taaataatac     600
caaaaaaagt tgccatttat tgtcagatac tgtgtaaaga aaaaattatt tagacgtgtt     660
```

```
aactggttta atcctacttc tgcctaggaa ggaaggtgtt atatcctctt tttaaaattc      720 ttttaattt tgactatata aactgataag tcctctctac ttcacagatt aagaaattga      780
tactcaaaaa agttaaataa cttgttttaa accacatagt aagtgccgaa gccaatctgt      840
gagaccagga ctgtttgtac tctaaatggc tgcaccacat gaggcaaaat ggctcgtgat      900
ggttttattt caaagaccta gaaaacacta tcacagctgg tgctcccgtc tcagacccac      960
agcaacgatg tctccacttc ctgcttcatc ttgggtttct cacgtcttga atgtgcacac     1020
aaatcacctg gggatcttgt taaaaatgca gcttctgttt caaaagaccc agactggaaa     1080
tggagattcc gcatgtctag tacgctctca agtttattaa tctgctgctg gtcctaggaa     1140
catattgagt agcgaggggc aggatgtgac tcctgtaagg agtggccagg cattttctta     1200
gagacctgtg ttataaagta tgcttttcct taaaaaaaag aagaaggagg aggaggagaa     1260
gggccaggtg cagtggctta cgcctgtaag cccagcattt tggggaccaa agtgggaag     1320 atcacttgag ctcaggagtt caagaccagc ctgggcaaag tagtgaaacc ccatttctac     1380
aaaaaattaa aaattagcca ggcaaggtgg cacacaccta tagttccagc tacttgggag     1440
gctgaggtgg aaggatcact tgagcccagg aggtcgaggc tgcagtaagc catgatcaag     1500
ccactgcact ccagcctgga gtgtctcaaa atagataaat aaataaataa ataaataaat     1560
aaataaataa ataaaagaga cagtatcaaa gacccaatca cctctagaca tctggcatca     1620
taggaatgtg cccagtctgc tctgggata ggaaagtggg gatcctgtct cccctgtgt      1680 agaggtttca gtaaaagaaa ggcctaggtg tgcagaaagc tttcaggcaa tgccagggaa     1740
actgatcatt gtaatgaatc cagggtattg ctgagtgagg gcatcctgga gggcccggtg     1800
gaaatgtggt caggctcttc aatgcacagg ccctagttga tgagtaatca gggtttcaaa     1860
tatttccatc tctgtctcaa gcagaaaaca aatggaaaaa ctgaaccacc agaaaagcag     1920
agccagagat ggaacaagaa tcccagtgtt tgtacccaac caagagcgtg ttttttcttcc    1980 acagacacca atgttcaaaa tggaggcttg ggggcaaaat tcttttgcta tgtctctagt     2040
cgtccaaaaa atggtcctaa cttttttctga ctcctgcttg tcaaaaattg tgggctcata    2100
gttaatgcta gatgcttcct tcctctattt ccccccaaat ttcctgggaa ccctggtca     2160 ataccagcag taagttccac tgttctaggg tgtagaaatg gctgtgaccc agcagcaaga    2220
gggaaggaca tcagatgtca tcagtggtca tactgcaaca cagcccttt tctgtttagg     2280 aatgcaggta cccacaacat ttactaacac ttttttttttc ttatttattt tctagttggc    2340
gtttgggggc aagatggtga gatatgcttt cttttctttct tttttatgaa atcaccccat    2400
cattctttgt agttatgaat ggagctttct cttaggcctc ccacagaact tccacagagg    2460
tcaggaaaag gagtttctgc catctacccc tttgactttc ctcacaagtc tggagatatt    2520
tctagcccag aagagggaag caacagaggc aggaaataat gagtcttaac catacaaaag    2580
aaaaattgag acttaaatga agttgaaagc actaacagtt ttcatttgtt tgcatttcat    2640
atttgatgtg agattctgca gaggagacgt agccagaatg catgcacagg ttactctgg    2700 ataagctgct ggggcaacat ttggatgtgt gttcagaatc acatgtctga atactctgaa    2760
tatatgtgtg tacatgtgta tttatgcaag tgcacatgca tatgagtgtg cccggcctga    2820
acttactctc tcaaccacag cggtagagtc aggagtgttc caacattgga agcccctcta    2880
ttcaatcagc tcttccaaac tgagtgaacc aatgttgtat ttaatggcaa ccatggctgg    2940
acaccatggc tcacacctgt aatcccagca ctttgggagg ccgaggtggg cagatcactt    3000
gaggccagga gttcgagacc agcctggcca acatggcgaa accccgtctc tactaaaaat    3060
```

```
accaaaatca gccagacatg gtggtgtacg cctgtagtcc tagctactcg agaagctgag   3120
gcaggagaat cgcttgaacc tgggaggcag aggttgtagt gagccgagat cacaccactg   3180
cactctagcc tgggtgacac atcgagactg tctcaaaaat aaaataaaga caaccattat   3240
gccagcctag attccgccat gctgcctaat ttgtagtgtc cttaggagcc atttttgtaa   3300
atagtcatca gataagatgt aaggcccata acagcttttt ctatgcagct gagggaattg   3360
gaagatccat tgtttcctaa gagttgaggg aagagtccca acccacggga gcagggtctg   3420
atcttcattg ccgatagaaa cattactaat ggcttcttac tgtttccttt tcaggtaatg   3480
aagaaatggg taagaagatt tccactctat ctagcaaaag ttttcaaata tggaatgaaa   3540
tgctcataga gtacaatcac agtaacaaac cctgagaact aaaactatta agggaaaat    3600 acaagtatct ttcaatggga tccgtatgaa acttgcctgt atttgttgct agctgtcatg   3660
tcagattata gctgtgcata tatgtatctc tgatcataca catatggatg tgggttggag   3720
ctaccatgtg tttttgtata agccatgaaa tctttgaagg cagacagaga cagtgtctca   3780
tttacctagc ccagtgtctg gcacatagta ggtgctcaat gaatattttt tgaatgaata   3840
aatgaacaaa catatgaaca cattgctaat tacctcccct caagaagctg atggtcttgt   3900
gtgagagaca ataattgaa atatagtga gttgcatgtt ataatatggg tagatacaga    3960
gtaaaatgaa gtaaagag gggagtggtc aactctactg agtgtcgttg ggaaaggttc      4020 cctggggag gtggtccttg agctgaattt taaaggataa gcttatgttt tagggaagaa     4080
aaatatttta tgcagaagag ataaagctgt atagtatgag gataagagtc taactgagct    4140
agatcagaat gtttgaatct tggctcaact ctctacttgc tgggtgtgtt tgagtaattt    4200
acctaacttt tctgtgccac agcatcatca tggtacaatg gaataatag tgctacctaa    4260 cttgtagggt tattatgagg accaaatgag taattcattt aaggcactta gaacattatc   4320
tgacataaaa ggcagtagga gggccgggca tggtggctca cacctgtaat cccagcactt   4380
tgagaagccg aggtgggagg atcacctgag gtcaggagtt cgagaccggc ctggccaaca   4440
tggtgaaact ccatctctgc taaaaataca aaaattagcc aggcatggtg gcaggtgcct   4500
gtaatctcag ctactcagga ggctgaggta ggagaattgc ttgaacctgg gaggcggagg   4560
ttggagtgag ctgagattgt gccattgcac tccagcctgg gcgacagagc aagactctgt   4620
ctcaaaacaa acaaacaaac aaacagacag taggtgaatt ttagctatta atacatggaa   4680
agcatgctga ctatagatga taagcattaa agtttactga gcatgtatgt tttaggcatt   4740
gctctaaata ttttacttga atttcctcat ttaattcttc caacacccct actgtacagt   4800
taaggaaaca aagcctcaaa taaatacaga aataaacaaa aataagtaaa caatccagtc   4860
ctggggatat aaatgcagat ttaggccaag tgccatggtt catgcctata atcccaacac   4920
tttgggaggc caaggcagga ggctcgcttg agctcagaag gttgaggctg cattgagcaa   4980
agattgtgcc actgtactcg agcctctgtg cagagaaag accctgtctc tgaaaaaatt   5040
aataaataga aatttaaaaa taaaaaaatt ttaatgcaga tttatatgat accgaagttc   5100 atttttctcaa ccattatgaa atactgtttc tggatatgta taaatctttt gtgagcacac  5160 atatctttt ttaacttaac tttcattta aattcagggg tacatgtgca ggtttgttat     5220
ataggtaaac ttgtgccatg ggggtttgtt gtatagatta tttcatcacc caggcattaa   5280
gcctggtacc tgttagttat ttttcctgat cctctccctc ctcccaccct ccaccttctg   5340
agaggtccca gtgtgtgtca tttccctctg tgttcatgtg ttctcatcat ttagctccca   5400
```

```
cttctaaatg agaacatgtg gtatttggtt ttctgtcact gtgttagttt gctaaagata    5460
atggcctcca gtcccatcca tgttcctgca aaggacgtga tctcattctt ttttatggct    5520
gcgtagtatt ccatggtgta tatgcagcac atttttttat ccagtctacc actgacaggc    5580
atttaggttg attccatgtc tttgctattg tgaatagtgc acaatgaaca tacgtggagc    5640
acatttctgt ctaagcacag acatctagac ccttgtgtga gcatgagtta agtctaagct    5700
ctgctactga atttgtgcca ataaaagttg tgagcaattt tctttacatt ttttttcaaac   5760 aaacacaccc agcagagtat aatgtctatg tactttattt atgatttcta gttcatttaa    5820
catgtctaag aaacatccgt gttgaaaaat tatttataaa ttaaaataat ataaactatc    5880
tactgtcctt atactcaact cccaattata agcaggtgga aaaacctgga gaatgttttg    5940
tttacattct gtgcagtctt tgtcagaggg ctgcctgagc aactgggtca gagtttagtt    6000
ctgctctggg agtagcagga cctcaagaag gaaaggagga aaggaagtaa cttttttcttg   6060 agcacctgct atgtgtcatt cactttcacc ttcataatcc atttaatttt cgcaaaaact    6120
ttgtgaggtt ggtgttttat ctccatttcc ctgataaaga agttgaggtt cagcaaagtt    6180
aaatgacttg ccctcagtca cacagactag ggcagatcca ggattcaaac tcagggcttc    6240
tgactcttga gtccagagct ctgtccctga cagcagcagc actgcctctc ctctcttcca    6300
gctgttatgt ccagactgta gcagaaccca gtgttccagc cacaagtttt ccaggaaata    6360 ataaggact cctagctcca cctcccaggg caaaaatggc tgctgtggga aacacaggct     6420
ggacctacga atggcattag tggtttatta gttgatttca gttgtccaca ctaataggcc    6480
tccctctaac aaaaataatt gagagctgat tatgctcaga tataatgtaa agtgaagcca    6540 cttttttattg gaagaagcat tccctcaaaa cgtgtagagt atttcacatt atttaaaggc   6600
aaatagagag aaaattatat ggaataagaa caaagatgtt tcttctctat tatgagggac    6660
tcagttctga gaaggatttt taaattgtaa gaaataggta agtccacgaa tcagtgattc    6720
agtggtgtgg agagctttat ttctgagaag gccagtagcg ctcccttctg acaagcaaat    6780
ctaagacctg gatgacagat gacttcctgc atttggttgg ttcttttgtc attcatatct    6840
atctgtaata cagttctggc taatttaaga ggataagctt gaagacctct ggaatttttc    6900
ggctttagga cttaaggct ttctgagctt cagtagatct agatctagga gctcatgctg     6960
gtatattctg aatccgatgt atctgagtta catctatgag ctacttaata aatatatcta    7020
tgagctaaat tcataggct aagcatgaac ctcacctcca agactcgggg ttcctaaatg     7080
gatgagaccc tctttgggaa gtcttgtggg cagtgtctaa ttccactaga aaagttttac    7140
ctacaattta aacttaaacc atgatatttt cttactgctg tttccttttt tcattttcag    7200
gtggtattac acagacacgt gagtttattg gtcttttatt tatgccctgt ctgaggatgc    7260
agattggtgg gtagatgaga aggaactgat tgagagagat taaccccaag aactgatatc    7320
ttcccagcat tgcattctca actccatttt agaaaggttc caaatagggac cttctgtggg   7380 ttttctttta catccatctt acccttccca agtccccatg tccctgcgta aaccctaaag    7440
ccacctctca aaaggttctc tagttcccctt caaggttctc tagttcccctt cattccacat  7500 atctcctctt ccacaccctc tagccagtag agctcccttc tgacaagcaa gtctaagatc    7560
tagatgacag atgacttcct gcatttgggt ggttcttttg tcactaattt gccttttcta    7620
aaattgtcct ggtttcttct gccaattccc cttctttctc cccagcatat aaagtctcca    7680
tctctggaac cacagtaata ttgacatgcc ctcagtatcc tggatctgaa atactatggc    7740
aacacaatga taaaaacata ggcggtgatg aggatgataa aaacataggc agtgatgagg    7800
```

```
atcacctgtc actgaaggaa ttttcagaat tggagcaaag tggttattat gtctgctacc    7860
ccagaggaag caaaccagaa gatgcgaact tttatctcta cctgagggca agaggtaatc    7920
caggtctcca gaacaggtac caccggctct ttagggagga ccattcaaaa gggcattctc    7980
agtgattttc cctaacccag ctcacagtgc ccaggcgtct ttgcgcttcc tcccacactc    8040
aatcctggga ctctctggta ccacacggca tcagtgtttt ctggaatata gattaaacac    8100
caatatgagg cttctgggta accccagtct gtgcgagatc taaaatagca actccctaag    8160
agacaggact gggtcatttg caccgcatca cacccaggtt catagcacac caacatgagt    8220
ttatctaatg cttcctccag agataaattt ttcagaaagg tttgcaaaaa acactcaagg    8280
ccactatagt aaaatggcat aagctaaggt ataataataa aataataaca atacttaaca    8340
tttattgagt gctattaag tctcaagcac tgtctgtacc caacacttat caaggattct     8400
ttttcatgta atcctctcaa caactatatg ggttaagtat cattttattc ccatgagtaa    8460
agggatgagg aaacagaggg tttgtgagtt gaaaacacat ttcacgcttc tcacagctag    8520
tgagtaataa agctgggact caaacccagg gctgtttgac tccagtgcct ctacccacgg    8580
ccaccactct ttgcttgtca atgttgttct aaacatattg aaggggggc tctgaccgtg     8640 gcaagcgtgt gagtagtaag gggagaatgg ccttcatgca ctccctcctc acctccagcg    8700
ccttgtgttt tccttgctta gtgatttccc ctctccccac cccaccccc acagtgtgtg     8760 agaactgcat ggagatggat gtgatgtcgg tggccacaat tgtcatagtg gacatctgca    8820
tcactggggg cttgctgctg ctggtttact actggagcaa gaatagaaag gccaaggcca    8880
agcctgtgac acgaggagcg ggtgctggcg gcaggcaaag gggtaaggct gtggagtcca    8940
gtcagaggag attcctgcca aggggacga ccagcctggg ccagggtggg tggcaagtcc      9000
acagctaggt cagaacagct tctctagagc ttctatgcac agcttctatt actgtgatga    9060
caagatctca acagacggtt tcaaatctca catcactccc ctccttccca tcctagaaaa    9120
gtgcaaaaaa gtttatgaaa gtgatgggct tcctcacata cctgtcaatg cctgcagtca    9180
tccgattccg cccctaagct gtgggaagag agactttgat atattagctc ctgccttttc    9240
cttccccttc ccctatggag agaaacaatg ggaggatctt gagctgagga aagtcacaaa    9300
atgatgagaa gagtgtaggg tccttagaga tgaatgaaag aaaaaaaaag agaaaggacg    9360
tctgaacaga aaagggagcg gtagaggaga gaacaatggg gtttgccatt ctctatctgg    9420
gtctcactgg cacagacagt gctgcaagat tggttccctc atgggaatga aatgtttccc    9480
ctccttcctc cgcaggacaa aacaaggaga ggccaccacc tgttcccaac ccagactatg    9540
aggtaacgtg ggatagaaat gggccaggac gctggagggg atgtccctcc agggggaag     9600 gaaacagatg ggatggccca tcttgtctgc cagatgcctc aaagcccctc actcagggct    9660
tccattacaa ccctctatgt gccacctctg cgtccttcat ggtaaaacag gactgtctca    9720
aaggctgcat ggcttccaca accatggaga ggtggaagct tgcaggagac atactcctct    9780
ttctctggct tattcattga ctgggataca gccatggaga atattatata tgcaaattct    9840
aacacaataa attctgggct gatattccac cagcatgcac cagtatagcg agttattgaa    9900
atattaaaat tatataaata ttatataaaa gttattgaaa tattaaaata ctcattggga    9960
aatagcccca aactttgctc accccaaccc acccttacac acacacatac acacacacac   10020
acacacacac acacacacac acacacacgt gaccagacat cccagtccct cccctaccgg   10080
gctgcctctt gagttgggt aacaaagagt taatgcctgg catggcagag gatcaccagg     10140
```

| | | | | |
|---|---|---|---|---|
| attgttctag | ttgattggta | tgtgtgcact | cctagttgtt aaatattttc | actatcacac | 10200 |
| ctggatatac | tcaacaaata | tttgttgagc | caaatactca acaccagcca | aacacgtagt | 10260 |
| atttactta | gcttaagcga | attatttagc | cctgacagaa gccctggaat | gtgggtcttt | 10320 |
| aagttcctat | ttttgagatg | ggaaagctga | ggctcacgga aggaggtgac | cagctcaagt | 10380 |
| ctcctaccgt | ccatgccaaa | ttagaattcc | agcctgcctc ctgacttcaa | gtccaaagtt | 10440 |
| cttcccacgc | actaaagcta | gctcttcagt | gtcctttctt aggaggtact | tcctcccgca | 10500 |
| ccactgaccg | cccctctct | atttcacccc | cagcccatcc ggaaaggcca | gcgggacctg | 10560 |
| tattctggcc | tgaatcagag | acgcatctga | | | 10590 |

<210> SEQ ID NO 40
<211> LENGTH: 1490
<212> TYPE: DNA
<213> ORGANISM: Artificial Sequence
<220> FEATURE:
<223> OTHER INFORMATION: Homo sapiens and Mus musculus

<400> SEQUENCE: 40

| | | | | |
|---|---|---|---|---|
| gcgtctggtg | ccttcttcag | aaatgaagta | atgagctggc tgcgtccgcc | atcttggtag | 60 |
| agagagcatt | ctgagaggat | gcagtcgggc | actcactgga gagttctggg | cctctgcctc | 120 |
| ttatcagttg | gcgtttgggg | gcaagatggt | aatgaagaaa tgggtggtat | tacacagaca | 180 |
| ccatataaag | tctccatctc | tggaaccaca | gtaatattga catgccctca | gtatcctgga | 240 |
| tctgaaatac | tatggcaaca | caatgataaa | acataggcg gtgatgagga | tgataaaaac | 300 |
| ataggcagtg | atgaggatca | cctgtcactg | aaggaatttt cagaattgga | gcaaagtggt | 360 |
| tattatgtct | gctaccccag | aggaagcaaa | ccagaagatg cgaacttta | tctctacctg | 420 |
| agggcaagag | tgtgtgagaa | ctgcatggag | atggatgtga tgtcggtggc | cacaattgtc | 480 |
| atagtggaca | tctgcatcac | tgggggcttg | ctgctgctgg tttactactg | gagcaagaat | 540 |
| agaaaggcca | aggccaagcc | tgtgacacga | ggagcgggtg ctggcggcag | gcaaagggga | 600 |
| caaaacaagg | agaggccacc | acctgttccc | aacccagact atgagcccat | ccggaaaggc | 660 |
| cagcgggacc | tgtattctgg | cctgaatcag | agacgcatct gacagatagg | agagacatcg | 720 |
| ccttctgtgg | acccagatcc | agccctccga | gcaccctgct actccttgtt | ctctggacag | 780 |
| actgcagact | ccacagcttg | ctcttcagcc | tcctggtgaa cacgtgtcct | agaaccttgc | 840 |
| tctcctgcct | cctctgctag | tagccagtgc | tgggacattg ctgactcaac | agcctttgaa | 900 |
| agaatcaggc | tgctcagatt | gtctgccagc | caccttgtgg ggatactttt | ttcagccgcc | 960 |
| ctgctgccag | ctccccgctg | cctcaccagt | gtcctctctg cctcagttcc | tttcctctcc | 1020 |
| taattggccc | tcatagctaa | gcccttcct | acagctttct gttttttctt | tttctttctt | 1080 |
| tttaggtttt | cttctttc | ttttttattc | ctttttattt aatcttttt | ttttaaacac | 1140 |
| tccagatttt | attccctcc | cggcccatcc | tccgactgtt acacacccca | tacctcctcc | 1200 |
| ctgccccctt | gtctctacga | gaatgtccc | cacccccatc ccccacctgc | tttctggttt | 1260 |
| ttggttttg | gtttgtttt | ttttttaaa | ctctgtgttt tacactcttc | tctgggatgg | 1320 |
| attctgtaat | cattggcaca | ggtcctgccc | catttataga tcctggccca | gccctgcca | 1380 |
| caggtgcctc | tccagatttc | cccttagatc | ctcggatggt catctccatc | tccatgaata | 1440 |
| caccagcccc | ctctctgcta | atgcaaaagg | caataaagtg tattggctgg | | 1490 |

UNITED STATES PATENT AND TRADEMARK OFFICE
CERTIFICATE OF CORRECTION

PATENT NO. : 10,945,420 B2
APPLICATION NO. : 16/436805
DATED : March 16, 2021
INVENTOR(S) : Yuelei Shen et al.

Page 1 of 1

It is certified that error appears in the above-identified patent and that said Letters Patent is hereby corrected as shown below:

In the Specification

Column 1, Line 1, delete "BiocytogenPharmaceuticals" and insert -- Biocytogen Pharmaceuticals --, therefor;

In the Claims

In Column 101, Line 9 (approx.), in Claim 1, delete "adds" and insert -- acids --, therefor;

In Column 102, Line 35 (approx.), In Claim 16, delete "CD3 δ," and insert -- CD3δ, --, therefor.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*